United States Patent
Partovi et al.

(10) Patent No.: US 7,660,413 B2
(45) Date of Patent: Feb. 9, 2010

(54) SECURE DIGITAL COURIERING SYSTEM AND METHOD

(76) Inventors: Shahram Partovi, 5535 N. Camino Del Contento, Paradise Valley, AZ (US) 85253; C. Roger Bird, 70 Biltmore Estates, Phoenix, AZ (US) 85016

(*) Notice: Subject to any disclaimer, the term of this patent is extended or adjusted under 35 U.S.C. 154(b) by 340 days.

(21) Appl. No.: 11/402,152

(22) Filed: Apr. 10, 2006

(65) Prior Publication Data
US 2006/0230072 A1 Oct. 12, 2006

Related U.S. Application Data

(60) Provisional application No. 60/669,407, filed on Apr. 8, 2005.

(51) Int. Cl.
*G06F 21/00* (2006.01)
(52) U.S. Cl. .................. 380/33; 726/26; 705/3
(58) Field of Classification Search ........... 380/33; 726/26
See application file for complete search history.

(56) References Cited

U.S. PATENT DOCUMENTS

| | | | |
|---|---|---|---|
| 5,613,134 A * | 3/1997 | Lucus et al. ............ 715/210 |
| 5,671,353 A | 9/1997 | Tian et al. | |
| 5,823,948 A | 10/1998 | Ross, Jr. et al. | |
| 5,903,889 A | 5/1999 | de la Huerga et al. | |
| 5,953,419 A | 9/1999 | Lohstroh et al. | |
| 5,956,400 A | 9/1999 | Chaum et al. | |
| 6,148,342 A | 11/2000 | Ho | |
| 6,260,021 B1 * | 7/2001 | Wong et al. ............ 705/2 |
| 6,263,330 B1 | 7/2001 | Bessette | |
| 6,424,996 B1 | 7/2002 | Killcommons et al. | |
| 6,449,621 B1 | 9/2002 | Pettovello | |
| 6,463,417 B1 | 10/2002 | Schoenberg | |
| 6,557,102 B1 | 4/2003 | Wong et al. | |
| 6,574,629 B1 | 6/2003 | Cooke, Jr. et al. | |
| 6,574,742 B1 | 6/2003 | Jamroga et al. | |
| 6,611,846 B1 | 8/2003 | Stoodley | |
| 6,651,060 B1 | 11/2003 | Harper et al. | |
| 6,678,703 B2 | 1/2004 | Rothschild et al. | |
| 6,678,764 B2 | 1/2004 | Parvulescu et al. | |
| 6,691,134 B1 | 2/2004 | Babula et al. | |
| 6,738,798 B1 | 5/2004 | Ploetz et al. | |
| 6,763,344 B1 | 7/2004 | Osentoski et al. | |
| 6,775,670 B2 | 8/2004 | Bessette | |
| 6,915,265 B1 * | 7/2005 | Johnson ............ 705/2 |
| 7,024,563 B2 * | 4/2006 | Shimosato et al. ...... 713/186 |
| 2001/0032100 A1 | 10/2001 | Mahmud et al. | |
| 2001/0041991 A1 | 11/2001 | Segal et al. | |
| 2002/0010679 A1 | 1/2002 | Felsher | |
| 2002/0156650 A1 | 10/2002 | Klein et al. | |

(Continued)

*Primary Examiner*—Gilberto Barron, Jr.
*Assistant Examiner*—Devin Almeida
(74) *Attorney, Agent, or Firm*—Jeffrey D. Moy; Weiss & Moy, P.C.

(57) ABSTRACT

A digital couriering system and method for electronically moving records and images through a central user interface with a centralized security and access mechanism is disclosed. The disclosed system and method is a network that makes it possible for records comprising personal information and other non-personal information to be delivered in seconds via the Internet, instead of days through the use of the current standard couriers, such as messenger services or regular mail. Using the disclosed system and method, vital documents not only reach their destination more quickly but also in a more cost effective manner.

47 Claims, 43 Drawing Sheets

U.S. PATENT DOCUMENTS

| | | |
|---|---|---|
| 2003/0088441 A1 | 5/2003 | McNerney |
| 2003/0140044 A1 | 7/2003 | Mok et al. |
| 2004/0034550 A1 | 2/2004 | Menschik et al. |
| 2004/0069311 A1 | 4/2004 | Sasaki et al. |
| 2004/0133797 A1 | 7/2004 | Arnold |
| 2004/0139222 A1 | 7/2004 | Slik et al. |
| 2004/0199765 A1 | 10/2004 | Kohane et al. |

* cited by examiner

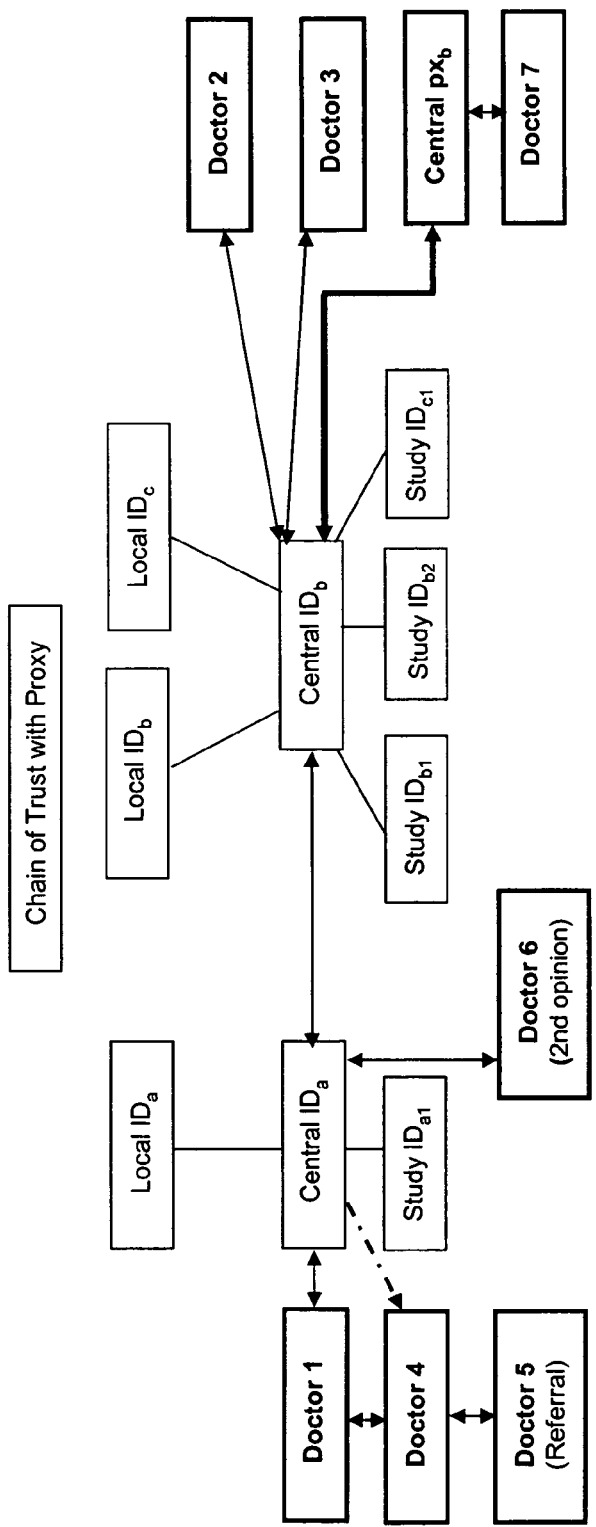
FIG. 28C Chain of Trust with Proxy
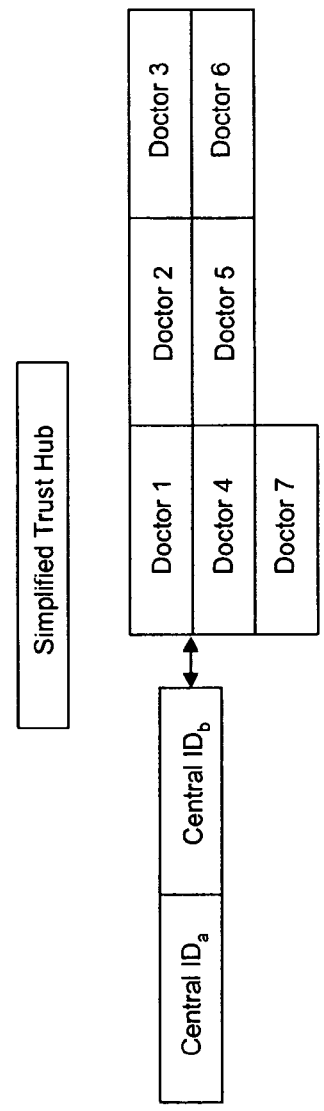
FIG. 28D Simplified Trust Hub

SECURE DIGITAL COURIERING SYSTEM AND METHOD

CLAIM TO DOMESTIC PRIORITY

This Application claims the benefit of priority of U.S. Application Ser. No. 60/669,407 filed Apr. 8, 2005.

FIELD OF THE INVENTION

This invention relates generally to a system and method for electronically moving images and records among unaffiliated sites, and more particularly to a digital couriering system and method for electronically moving records and images through a central user interface with a centralized security and access mechanism.

BACKGROUND OF THE INVENTION

The market for electronic medical records and medical images has grown at a rapid pace over the past decade, and this growth is expected to continue its rapid ascent over the coming decades. The sheer volume of electronic medical records and medical images has mushroomed in the past 10-15 years. However, the movement of medical records and radiological studies from hospitals and imaging centers to physicians' offices, and even among physicians' offices, is a ubiquitous problem. Current solutions include the physical couriering of the records or films or point-to-point electronic connections.

Currently, digital medical images are not routinely transported outside of a secure intranet environment (e.g., over the Internet) for two principal reasons. First, medical images are, in most cases, too large to easily email. Second, under the Health Insurance Portability and Accountability Act of 1996 ("HIPAA"), measures must be taken to provide enhanced security and guarantee privacy of a patient's health information. These requirements cannot be satisfied through routine email or conventional Internet connections.

As a result, if a medical record or imaging study is to be sent from an imaging center or hospital to a referring physician's office, a physical film or compact disc (CD) must be printed and hand delivered. This is expensive, inaccurate, inefficient and slow. There does not exist today a simple electronic means of moving imaging studies, or other medical or similar records, among unaffiliated sites.

Therefore, in light of the present methods available for moving medical records, images and other personal information, a need exists for a system and method for providing a secure central interface for accessing and moving those records among authorized parties.

BRIEF DESCRIPTION OF THE DRAWINGS

FIGS. 15A through 15K illustrate various user interfaces for the disclosed system.

FIGS. 28A through 28D illustrate proxy chain of trust features of the disclosed system.

DETAILED DESCRIPTION OF VARIOUS EMBODIMENTS

Figure 1A:
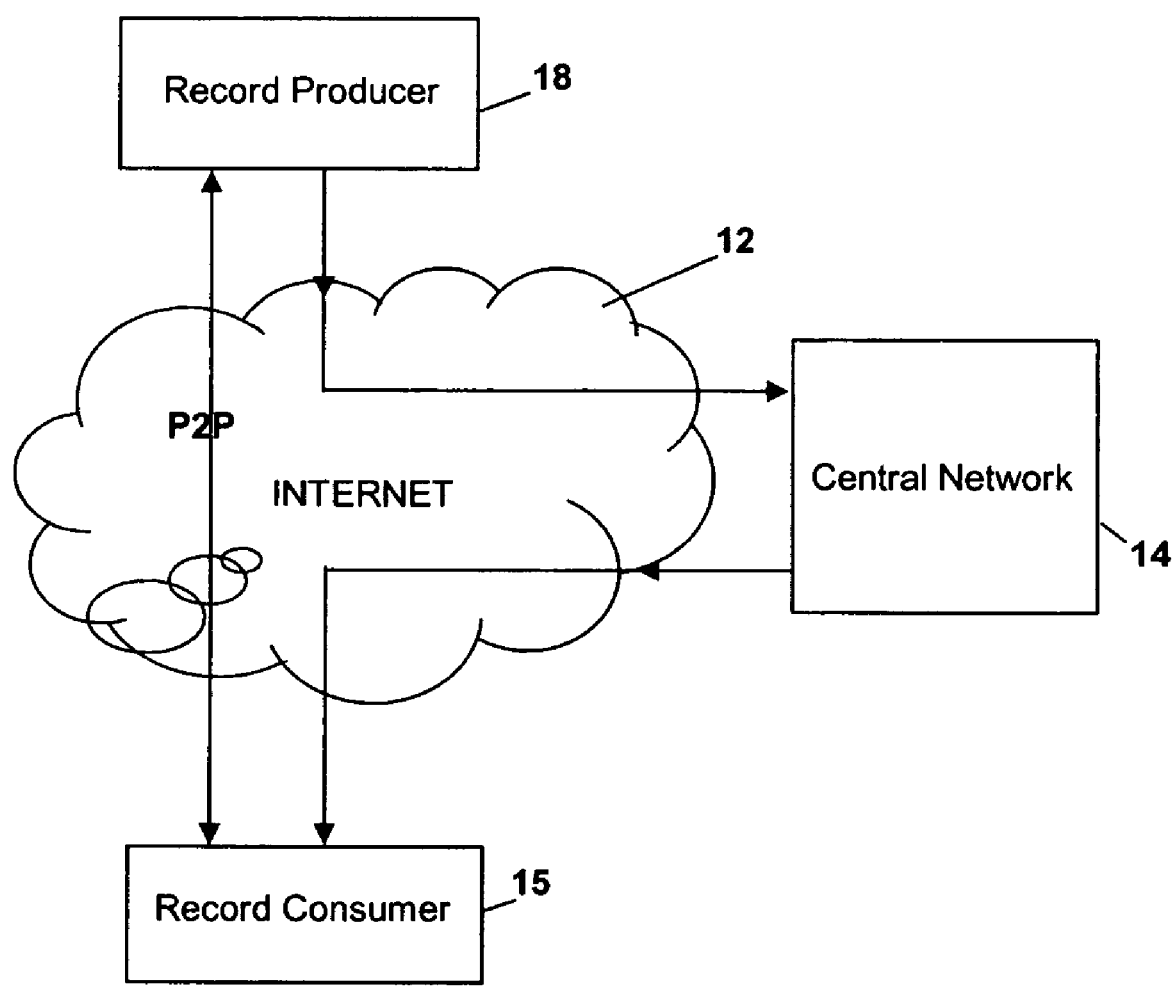
FIGS. 1A and 1B are general overviews of the disclosed digital couriering system.

The present invention is directed to a system and method for the storage and distribution of medical records, images and other personal information, including DICOM format medical images, over a peer-to-peer network. While it is envisioned that the present system and method are applicable to the electronic couriering of any records comprising both personal information and other information which is not personally identifiable (non-personal information), the present disclosure describes the system and method, by way of non-limiting example only, with particular applicability to medical records, and more specifically to medical image records, which are also referred to herein as DICOM files.

The disclosed system and method is a network that makes it possible for records comprising personal information and other non-personal information to be delivered in seconds via the Internet, instead of days through the use of the current standard couriers, such as messenger services or regular mail. Using the disclosed system and method, vital documents not only reach their destination more quickly but also in a more cost-effective manner.

According to the present system and method, a record, for example, a DICOM file, is composed of two major components: 1) the actual body of the record, for example, the image data, and 2) the image header information, which contains the personal or patient-identifying information. According to the present disclosure, the header contains personal identifying information, also known as personal information, Protected Health Information, or PHI. According to the present disclosure, without the PHI header, record data, including image data, is anonymous and does not contain any unique patient identifying information. Therefore, the non-personal or anonymous data portion of a record is referred to herein as the Body. Thus, records according to the present disclosure have at a minimum, two parts: 1) a header and 2) a body. It is recognized that not all personal information will be present in the form of a traditional header, but the term is used in the description of some embodiments for ease of reference to any PHI or personal information in a record. In other embodiments it is referred to as personal information or PHI.

Generally, the disclosed system and method stores the original record, comprised of the PHI and body of the record (for example, the image itself) at the original site (such as the hospital, laboratory or radiology practice group) where the record was created, for example, where the imaging procedure was first performed. Then, a centralized collection of servers helps manage the movement of the records, for example, DICOM files, over a peer-to-peer network.

These servers may include, but are not limited to: (1) a database of user accounts, also called a credential store. This database indicates persons authorized to access the system, which determines who is authorized to access the system; (2) a PHI directory, also called a Central Index, that maintains pointers to the distributed locations of all copies of all PHIs in the system; (3) a Storage Node Gateway Registry, also called a Node Manager that tracks the status and location of all Storage Nodes (or Source Nodes) associated with the system; and (4) a financial database to monitor transactions for billing purposes.

When a patient undergoes a procedure that produces a DICOM medical image file, the storage node at the originator securely forwards a copy of the DICOM PHI to the Central Index. Moreover, the image data devoid of its PHI information but accompanied by an encrypted identification key, is preemptively and securely transmitted from the originator's storage node to an authorized receiver's network node.

A non-preemptive, but rather subsequent, properly-authorized request identifying the patient and images can also cause the same non-PHI image data transmission to occur. At the receiver's network node, a properly-authorized user can view the image data and, using the encrypted identification key, dynamically download and append the respective PHI to the anonymous image data to effectively recompose the original DICOM image file.

The PHI directory, or Central Index, keeps track of the locations of all copies of the original DICOM files. The Node Manager oversees inter-nodal peer-to-peer communication and monitors the status of each node, including whether currently online. Thus, in the case of multiple copies, a request to view a DICOM study will be routed from the closest available Storage Node containing the file. Images move on the network without identifying information and identifiers move without any associated images; only an authorized account holder with the proper encryption key can put the PHI and image data together, and then only on a transitory basis without the ability to save or otherwise store them.

As discussed above, this system also functions with medical records in the known HL7 format, or other records comprised of personal and non-personal information in various other formats known in the art.

A subsidiary feature of the system is a "chain of trust" in which certain classes of authorized viewers (e.g., a treating physician) may pass on electronic authorization to another viewer (e.g., a consulting specialist) who is also in the accounts database. The owner of the information, the patient, may log on and observe all pointers to his or her data and the chain(s) of trust associated with his PHI and may activate or revoke trust authority with respect to any of them.

The following detailed description of the figures graphically illustrates the interrelationship of elements in the system. A technical architecture design of the system is also described in detail.

Before proceeding to a description of the figures, some preliminary connotational matters will be addressed. The term "Central Server" or "Central Network" will be used to designate the servers on which the central functions of the disclosed couriering system and method will be maintained. The Central Server may comprise one or more servers. For example, the Central Server may be comprised of a website server, a storage server, a security server, a system administration server, a node manager and one or more application servers. In another embodiment, the Central Server may be comprised of a set of managers, including but not limited to a header manager, an audit manager, a security manager, a node manager, a database manager, and a website manager.

Also, the Central Server or Central Network comprises at least a database of user accounts, also referred to herein as the credential store and a PHI directory or Central Index that holds all the information on what patients and their records are in the couriering system. Thus, the Central Index is comprised of pointers to the distributed locations of all copies of all PHIs in the system.

The Record Producer, also called the Image Producer, is the entity, such as the imaging center, hospital, doctor or other entity, that creates the record or image and has the original electronic record stored on its server. Image Producers also include PACS machines or Picture Archiving Communication Systems. PACS is an existing technology that allows medical images to be shared digitally within a group or by Internet.

The disclosed courier system and method is substantially different than PACS. PACS depend on a Virtual Private Network (VPN) solution to electronic records access. However, VPN solutions do not solve the problems with electronic couriering of records that the present system and method solve. For example, VPN infrastructure is exponentially more costly than the present system and method. VPN does not have the same user management and point-to-point access control as the present system and method. VPN does not have secure connection in which to transmit user credentials.

Further, unlike PACS, the present system and method does not have to manage multiple user logins for separate facilities. Rather, each Record Consumer has a single user login that works at all facilities, including home, office or mobile units. Finally, according to the present system and method, the authentication of Record Consumers is based on industry-wide standards and credentials that are consistent across the system, rather than the particular requirements of a facility, such as association with a hospital or clinic.

The Record Producer component of the system is set up as a Source Node, also referred to in some embodiments as a Storage Note or Local Storage Node (LSN), on the Peer-to-Peer Network, the primary responsibility of which is to supply records to the system. The record remains on the Record Producer's Storage Node or Local Storage Node until it is requested or the requesting party (usually the Record Consumer) is identified and the study is pushed to the Record Consumer's Target Node, also referred to as a Network Node. As will be discussed in greater detail below, there is a technical distinction between Target or Network Nodes (or P2P Network Nodes) and Source Nodes or Storage Nodes or LSNs, in that Source Nodes hold original records comprising both headers and a Body, while Target Nodes are nodes that do not store any original records. Some entities may have Nodes that function as both Source Nodes and Target Nodes if the entity is both a Record Producer and Record Consumer.

The Record Harvester, also referred to herein as the Harvester or Image Harvester, is defined as the primary method for getting records from the Record Producers into the Central Index. The Record Harvester tags each record, for example a DICOM file, with a Harvester Tag. The Harvester Tag allows each record to be linked back up with the associated header (personal information) once the file has been moved to the Record Consumer's server for viewing.

The Harvester Tag may be complementary unique identifiers, complementary hashes or watermarks. Watermarking is a process whereby irreversible, and often invisible-to-the-human eye, changes are made to an image file. This is essentially a process of embedding a key within an image. These visible or invisible image file alterations can be detected by software applications and used to confirm the authenticity and origin of an image. Such information can be used as a key to bind an image to its original personal information.

The Record Consumers, also called Image Consumers, are the recipients or accessors of the records stored on the Record Producer's Source Node. In one embodiment, Record Consumers include, but are not limited to, doctors, their proxies, hospital staff, patients, insurance companies, and administrators. The Record Consumer's server normally has Client Application software loaded on it. Client Application software is also referred to herein as the User Application or Client Viewer. The Client Application software allows the Record Consumers to view their records or their patients' records. For example, records can be viewed, forwarded and requested by a physician using the Client Application. The viewing of the record, as facilitated by the Client Application, includes the security of managing the PHI as well as security and role authentication.

Therefore, according to one embodiment, records are stored in two locations: (1) the Record Producer's computer; and (2) the Source Node. The body is stored on the Record Consumer's computer but the header is stored only on the Source Node and at the Central Network. The header is never stored on the record consumer's system. The record producer also maintains a record consumer list.

As shown in FIG. 1A, the Peer-to-Peer Network and the Central Network 14 are accessed through the Internet or World Wide Web, in some instances as a web site. Additionally, while it is recognized that there is a technological distinction between Internet and World Wide Web, the terms are seemingly interchangeable and used as such throughout this description. The use of these terms in this fashion is for descriptive convenience only. The skilled artisan will appreciate that the system encompasses the technological context of both the Internet and the World Wide Web.

The Peer-to-Peer Network controls the flow of records across the system and ensures that the records are only transmitted to valid Record Consumers. The endpoints of the Peer-to-Peer Network comprise nodes that can be Record Producer Nodes 18, Record Consumer Nodes 15, or both, and are also referred to herein as Peer-to-Peer Nodes or P2P Nodes.

Finally, the security features of the disclosed system and method may include three separate levels of security to maintain a secure end-to-end system. The first level is User Authentication. Use Authentication employs various techniques known in the art to authenticate various end users of the system, such as Record Consumers.

The second level of security is Nodal Validation. Nodal Validation is the process of identifying unique nodes to the disclosed system. As is disclosed herein, there are different types of nodes that will be available on the system, such as Target or Peer-to-Peer Nodes, Source or Local Storage Nodes (including LSNs that are part of the Edge Server) and Virtual Local Storage Nodes. Each node type will require a unique identification and validation process.

Third, as discussed above, the system will transfer various types of data over its network in different functional scenarios. As noted above, the data typically falls into two categories, PHI or private data that must be encrypted and body data that is not sensitive or private by itself and may be left unencrypted over the wire. However, the present discloseure envisions that even body data may be encrypted if so desired.

One particular application and embodiment of the present system and method links facilities that produce and consume medical images in DICOM format. The disclosed system, including a peer-to-peer network, enables the linking of imaging centers and physicians' offices to reduce the costs of moving medical imaging files from location to location via mail and courier services. As noted above, the system addresses the concerns of HIPAA guidelines to maintain all private patient information during transit and storage, and only allow visibility to this information by the appropriate people who are giving care to the patient.

In the particular application, the system takes images from imagining centers and hospitals as input into the system and makes those available to the appropriate physician or healthcare provider at the time of visit to consult with the patient. This system eliminates the need for the imaging film to be sent to the physician's office or to have the patient carry the film with him once a study has been completed.

The disclosed system and method is based on the peer-to-peer network concept where clients, attached to the network, are able to communicate among themselves and transfer DICOM files without having to store these files at a central location. The movement of files across this network is managed by a central index and node manager which ensure that the files are transported to the proper locations and provides the security for the network.

In order to meet HIPAA regulations while working with PHI, the treatment of the DICOM files and their private information is monitored carefully across the network and always transmitted in a secure fashion using industry standards such as Secure Sockets Layer (SSL) and Public Key Infrastructure (PKI). Security is also paramount when transmitting files to a desktop of a physician so he can view them without waiting for a download to complete. At this point, no private information is stored with the DICOM file. Only with direct privilege of a physician login can the private healthcare information for a patient be viewed together with the medical image or study.

When the patient's information (PHI) is requested, it is always transferred in a secure fashion and promptly and completely deleted when it is no longer needed. Furthermore, this information is never written to a local file or stored in any way outside the secure boundaries of the Central Server.

Finally, the system is able to track and audit the movement and viewing of DICOM files across the network. The tracking mechanism allows patients to see where their files are going as well as who has viewed them. A patient can also control access to his studies to prevent or enable a physician to gain access to them.

Figure 1B:
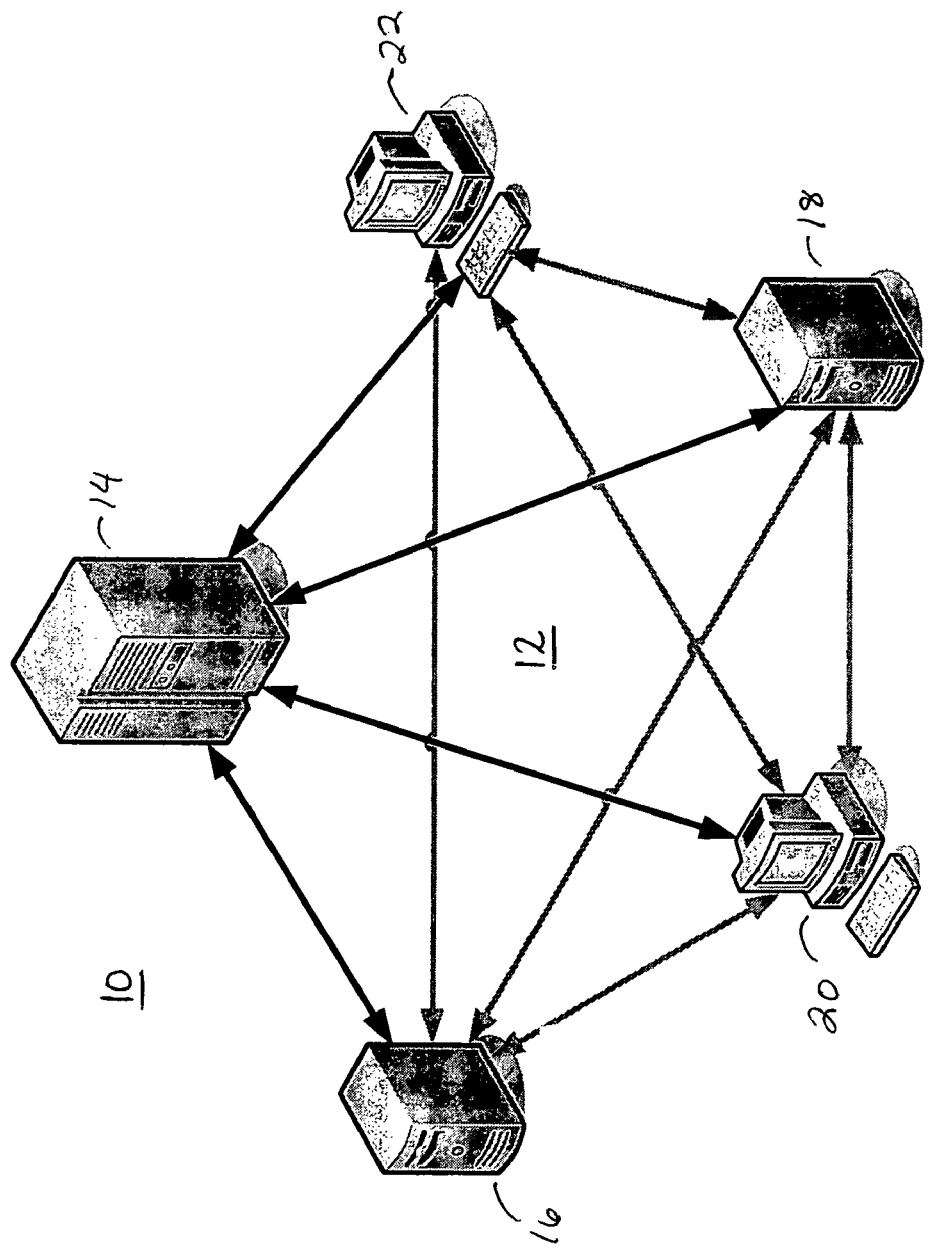

FIG. 1B illustrates one embodiment of a system 10 for couriering according to the present disclosure. System 10 includes a peer-to-peer network connecting a Central Server 14 with several other servers, including a storage server and a network (P2P) server.

The Central Server 14 is any type of computer server capable of supporting a web site and web-based management tool. The operating system used to run Central Server 14 and programming used in implementing the method of one embodiment are stored in unillustrated memory resident with Central Server 14. The operating system and stored programming used in implementing the method of one embodiment can be any operating system or programming language. According to this embodiment of the invention, the other servers may include, but are not limited to, hospital server 16, record producer server 18, doctor's office server 20 and home server 22. It is important to note that according to the present disclosure, hospital server 16, doctor's office server 20 and home server 22 are collectively referred to as record consumers.

As shown in FIG. 1B, servers on the P2P network communicate via electronic communication, for example via the Internet or other secured data transfer mechanism. However, it is envisioned that the preferred method will be Internet communication using standard, generally-known data exchange techniques such as the TCP/IP protocol.

The various hardware and software components of system 10 communicate, in one embodiment, via the Internet 12, to implement the method of the present invention. Although not depicted, Internet 12 access by nodes could be implemented via an Internet Service Provider (ISP), a direct dial-up modem connection, a digital subscriber link (DSL), a dedicated T-1 connection, a wireless local area network connection (WLAN), a cellular signal or satellite relay, or any other communication link.

Figure 2:
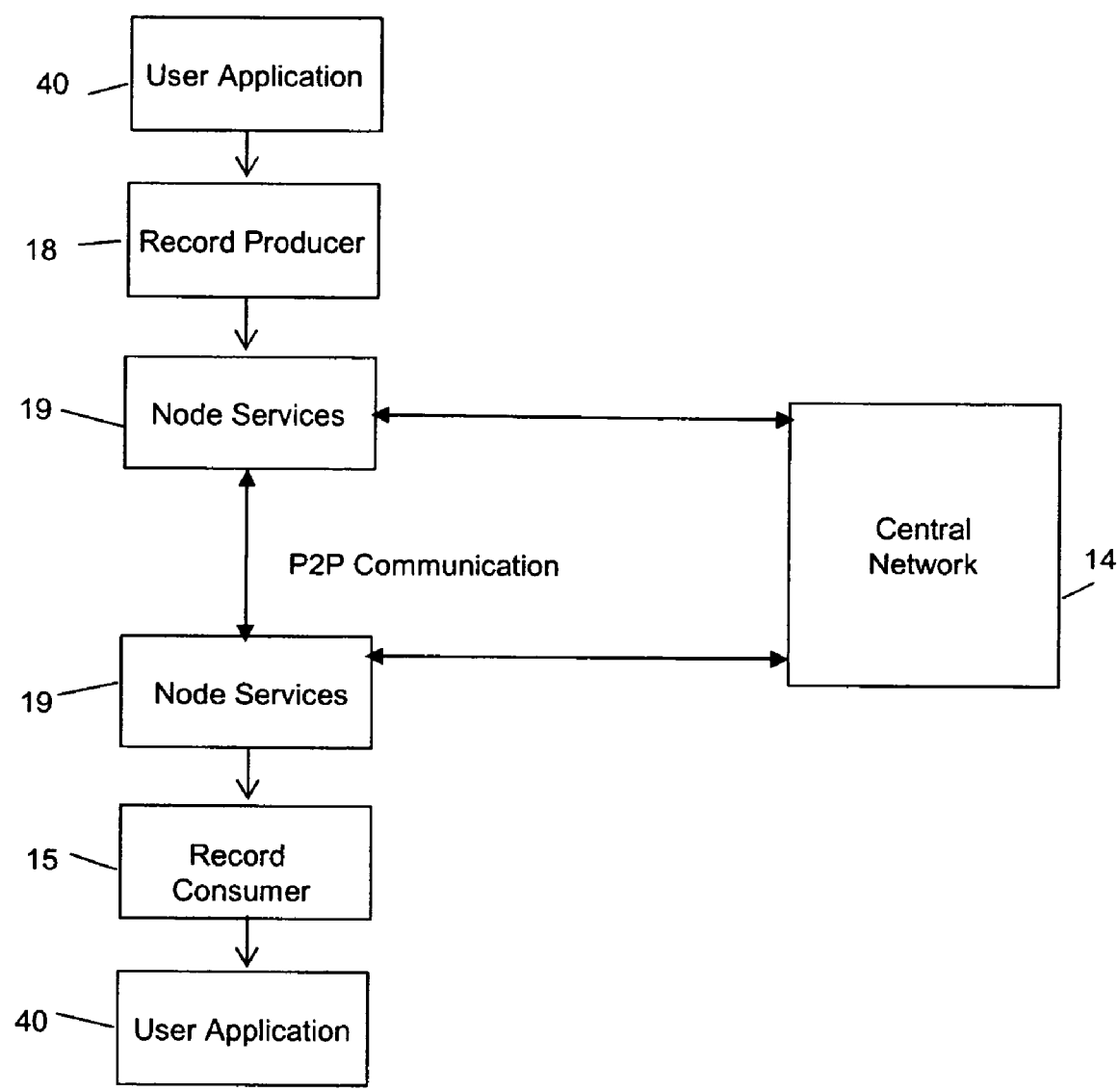
FIG. 2 is a flowchart illustrates the general flow of the disclosed digital couriering system and method.

FIG. 2 illustrates the general flow of information across the disclosed system. User application 40 is installed on Record Producer 18 and Record Consumer 15 computers, which facilitate end user communication and information flow through the node services 19 in each node, e.g., Target and Source, to other nodes via P2P communication, and to and from the Central Network 14.

Figure 3:
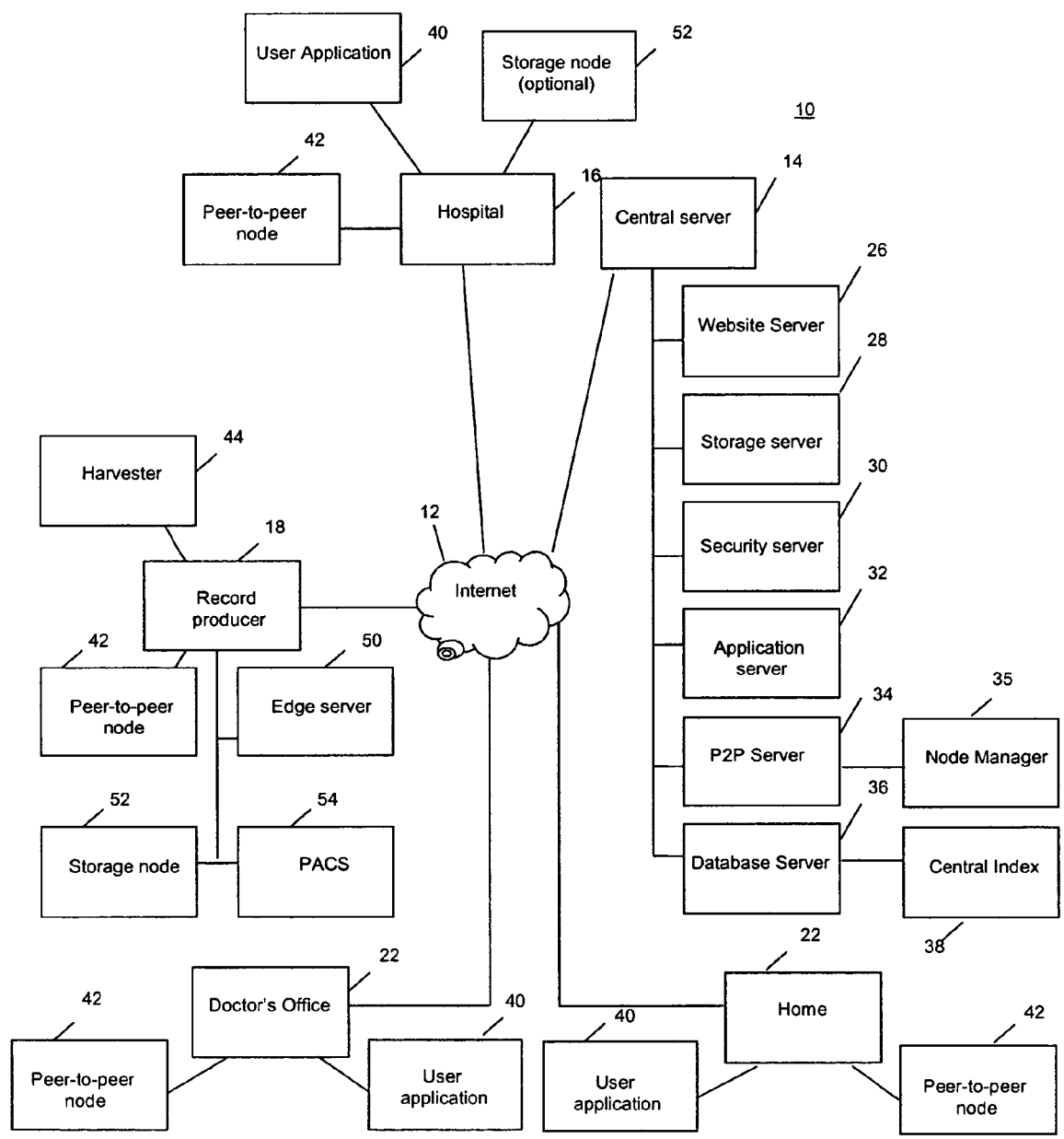
FIG. 3 illustrates one embodiment of the disclosed digital couriering system.

One embodiment of the disclosed system is shown in more detail in FIG. 3. In this embodiment, central network or central server 14 comprises one or more main server types, including website server 26, storage server 28, security server 30, application server 32, P2P server 34, and database server 36. Website server 26 hosts both the main website for patients as well as the web service layer that supports the P2P network for the viewing application, discussed below. These web services are secured both from SSL as well as session ID tokens that change over a given period of time. Website server 26 can be any suitable machine known in the art running any suitable software. For example, website server 26 is a Windows 2003 server running IIS 6.0.

As noted above, website server 26 provides web service via one or more web sites stored in unillustrated memory, with the web site including one or more web pages. More specifically, the web pages are formatted and developed using Hyper Text Markup Language (HTML) code. As known in the art, an HTML web page includes both "content" and "markup" portions. The content portion is information that describes a web page's text or other information for display or playback on a computer or other personal electronic device via a display screen, audio device, DVD device or other multimedia device.

The markup portion is information that describes the web page's behavioral characteristics, including how the content is to be displayed (e.g., the frame set) and how other information can be accessed (e.g., hyperlinks). It is appreciated that other languages, such as SMGL ("Standard Generalized Markup Language"), XML ("Extensible Markup Language") DHMTL ("Dynamic Hyper Text Markup Language"), Java, Flash, Quick Time, or any other language for implementing web pages could be used.

Central Server 14 also includes database server 36. Database server 36 may run any suitable software, for example SQL2000 or SQL2005. Database server 36 comprises the Central Index 38 and thus is the main repository for patient information (PHI) and the location of related records on the system. Because the actual Body of the records is located on the Local Storage Nodes and not sent to the Central Server 14, the size of the database is relatively small.

Because a large amount of information is captured during the auditing of each transfer and record action, it is recommended that the system have some type of archiving of this audit information in order to maintain a high performance transactional system for the movement of records.

Finally, the P2P network server 34 is designated to manage the P2P network and the authorization to transfer files between different nodes on the network. The P2P network server 34 can run any suitable operating system and software; for example, the P2P network server 34 is a Windows 2003 server running 6.0 for web services. The P2P network server 34 also runs the node manager 35.

As noted above, the nodes on the network are comprised of two types: Storage Nodes for Record Producers and Network (P2P) Nodes for Record Consumers. According to the image embodiment of the present disclosure, producers are primarily imaging centers and consumers are mainly doctors' offices. However, hospitals, for example, may be hybrids and have a node that functions both as a source or storage node and as a target or network node, in that a hospital is likely to be both an image producer (performs an MRI) and an image consumer (retrieves an x-ray of a patient).

The computer or device used by the Record Producers 18 and Record Consumers (hospital 16, doctor's office 20, or home 22) in communicating with the Central Server 14 are any type of computing device capable of accessing the Central Server 14 through a host web site via the Internet 12, and capable of displaying the website server 26's stored web pages using well-known web browser software packages, or any other web browser software. Such computing devices or other electronic devices include, but are not limited to, personal computers (PCs), both IBM-compatible and MacIntosh; hand-held computing devices (e.g., PDAs), cellular telephone devices and web-based telephone sets (e.g., "Web-TV"), collectively referred to herein as Nodes.

The Nodes are responsible for all file transfers across the system and are controlled by the Node Manager 35 in the Central Server 14. Each record transfer is initiated by the Node Manager 35 and is validated once complete. This ensures that studies are only transferred to validated nodes and provides accurate detail for purposes of auditing and billing, discussed in detail below.

The Nodes are also the gateway for viewing the Client Application (user application) 40 and the Harvester 44 to communicate with the Central Server 14. By having this one point for communication with all Nodes, the system maintains tighter security and ensures that all communications are monitored and audited correctly.

When a record is transferred from one node to another, the Node Manager 35 is the controller of these records. Even though the traffic of the file does not travel through the Node Manager 35 or Central Server 14, all management and authorization to move files is controlled and logged at this level.

Figure 4:
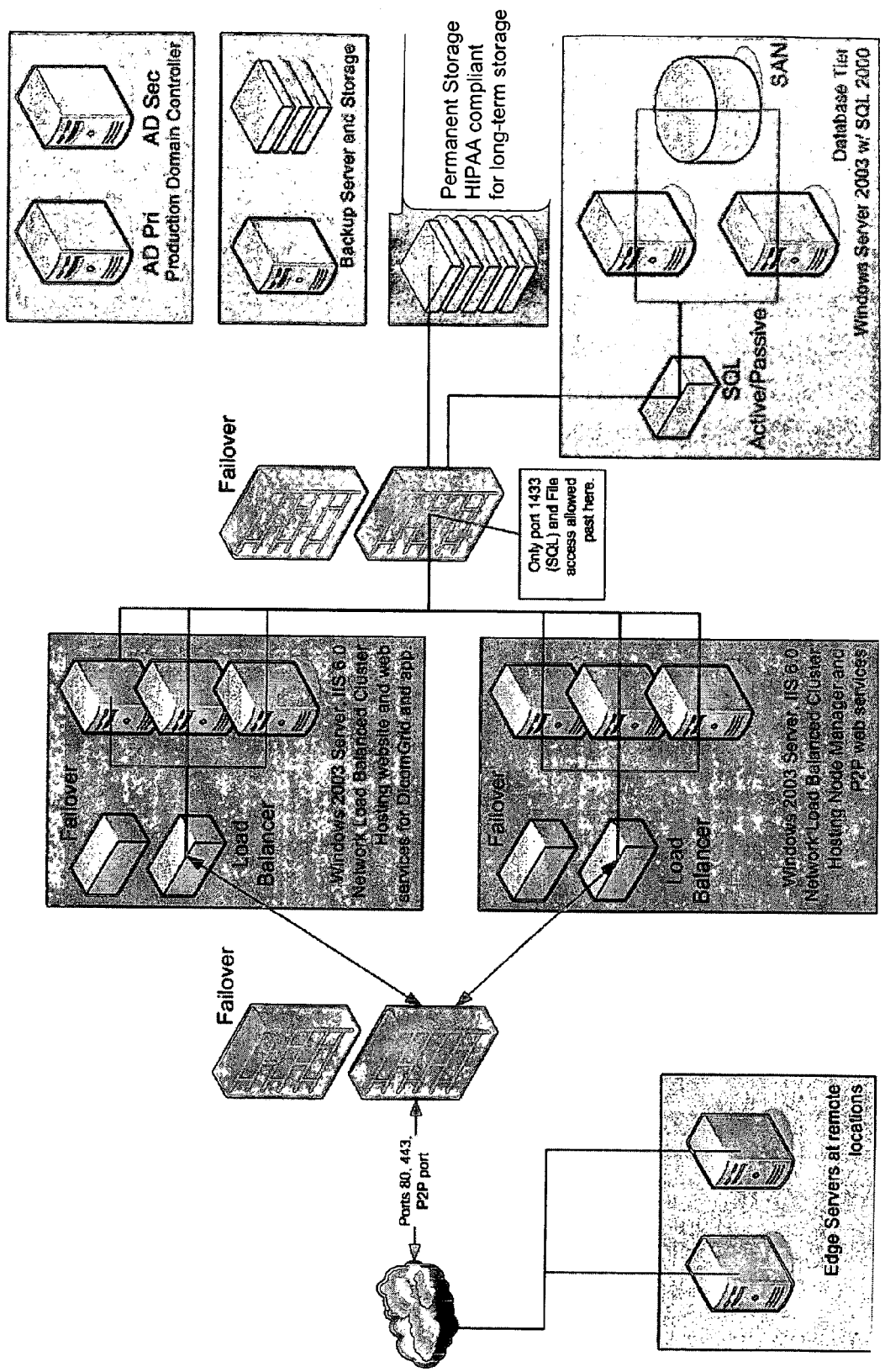
FIG. 4 is a detailed illustration of the production environment of the disclosed system.

FIG. 4 illustrates the production environment of the disclosed system in detail. The production environment shown in FIG. 4 portrays the hardware and setup needed to support the transaction level and user level of the disclosed system and associated applications. The primary advantages of this environment shown in FIG. 3 are reliability, redundancy, scalability and security.

As shown in FIG. 4, each single piece of hardware has a failover device in case of hardware failure. To allow for scalability and performance, clusters of three or more servers are used; however it is recognized that one server is sufficient. Multiple servers allow for significant failover, as all servers would have to go down before the system would become unresponsive.

Also as shown in FIG. 4, all personal information is located behind a dual firewall which provides for the most secure storage. The application, web and node servers all access this data through a secure transaction zone (DMZ). No private data is ever stored in the secure transaction zone, as this is the only method for accessing the data. In the secure data area, the domain controllers will provide the needed security for backups and SQL and possibly control access to the fixed storage.

In order to store records as permanent records for either image producers or patients, there is a HIPAA-compliant storage system that allows for Write Only, Read Many (WORM) disks. These disks ensure that records are not modified once they are stored and provide a method for HIPAA-compliant long-term storage. This storage can also be combined with a Storage Area Network (SAN) solution to provide a central area for all system storage.

Figure 5:
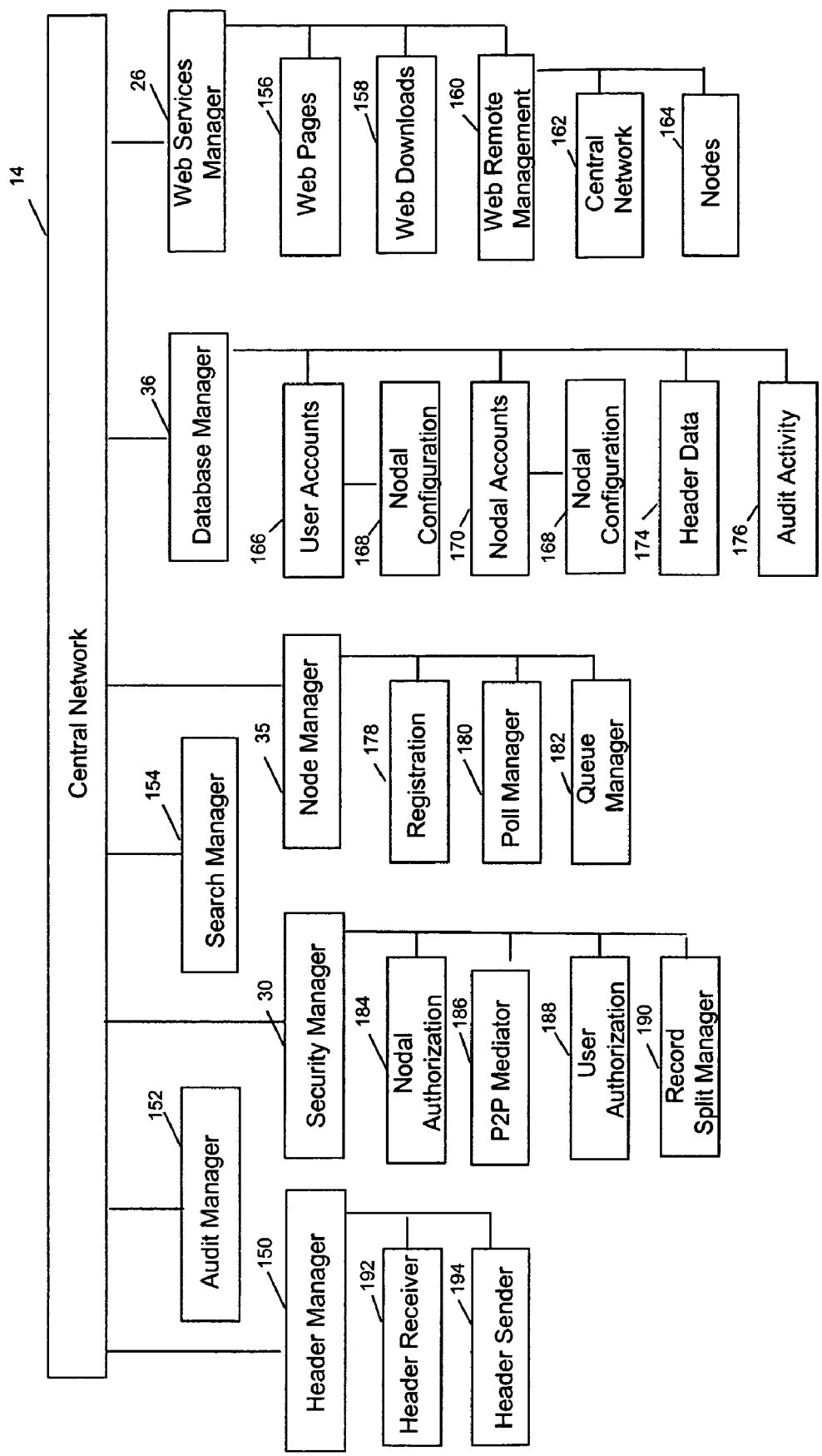
FIG. 5 is an illustration of the central network component of the disclosed digital couriering system.

FIG. 5 illustrates an alternate embodiment of Central Network 14. In FIG. 5, Central Network 14 is comprised of several managers, rather than servers. Central Network 14 may include, but is not limited to, web services manager 26, database manager 36 (similar to FIG. 3 database server 36), node manager 35, security manager 30 (similar to FIG. 3 security server 30), header manager 150, audit manager 152 and search manager 154.

The web services 26 component administers the web pages 156, web downloads 158 and web remote management 160. Web remote management 160 has at least two components: central network web management 162 and node web management 164.

Database manager 36 is comprised of components that manage user accounts 166, nodal accounts 170, header data 174 and audit activity 176. Both the user account component and nodal account provide for nodal configuration 168. Nodal configuration 168 provides and manages the latest configuration values for the node and transmits these to the node manager configuration, which pulls down the latest configuration values for the node and loads these onto the node's local storage of configuration data. Nodal configuration 168 could also include any updates to code in order to push out new versions or bug fixes.

Header manager 150 administers the access and storage of the header or PHI information in the database. The header, PHI or personal information is encrypted in the database to prevent any unauthorized database access from viewing the data. Header manager 150 is comprised of header retriever 192 and header sender 194. Header manager 150, including header retriever 192 and header sender 194, provides for several functions in the disclosed system. The header manager 150 only returns header information to a trusted session.

Header manager 150 encrypts the header information before loading it onto the database, and decrypts it before sending it to a calling function. In one embodiment, the encryption level is 32 bytes. The system encrypts search criteria for patient information and identifies encrypted data in the database using an encryption indicator in the tables. However, header information is never changed or deleted, and all access to the header information in the database is logged. The header sender 194 verifies the account has a trust for the header data before it is transmitted. Finally, header manager 150 manages searches from calling applications.

Header manager 150 interfaces with security manager 30, and in particular with user authorization 188. The interface with user authorization determines if the session identification or user has permission to receive the header data before being sent. This is accomplished in part by record split manager 190. In general, security manager 30 administers and authorizes access to the central network, the P2P network (through P2P mediator 186) and the trusts between record consumer and the record owner (e.g. physician and patient). Security manager 30 functions so that all access to the digital couriering system and the central network must have a valid session identification. Only one active session is allowed per user account. All nodes must be validated nodes to access the system through nodal authorization 184. Users are checked through user authorization 188 for trusts and permissions before information is transmitted. Nodes are authenticated when they access the central network. Security manager 30 logs messages when new trusts and proxies are created. FIGS. 27 and 28 illustrate the new trusts and proxies features in greater detail. All access is logged to the database.

Header manager 150 and security manager 30 also interface with the audit manager 152. Audit manager 152 centralizes the auditing of activity of the nodes and users on the system. Audit manager 152 is the component that logs the session identification or user and when the header identification data was accessed and/or viewed. Each record requires the session ID to record the activity. Audit manager 152 also logs the activity and transactions of the entire system, including saving the search criteria and session information to the database to track record viewing. Audit manager 152 creates a record in the database for each event that occurs on the system. Finally, all issues and errors are logged and assigned to a node or a node administrator.

Additionally, header manager 150 interfaces with search manager 154 to search the headers or personal information. Search manager 154 allows a search to be performed on a patient, physician and/or a facility. The type of search determines if the search requires header information. All header searches are passed to the header manager 150. As noted above, the header search process requires the search criteria to be encrypted before the search is performed on the encrypted information in the database. All searches are logged in the database.

Figure 16A:
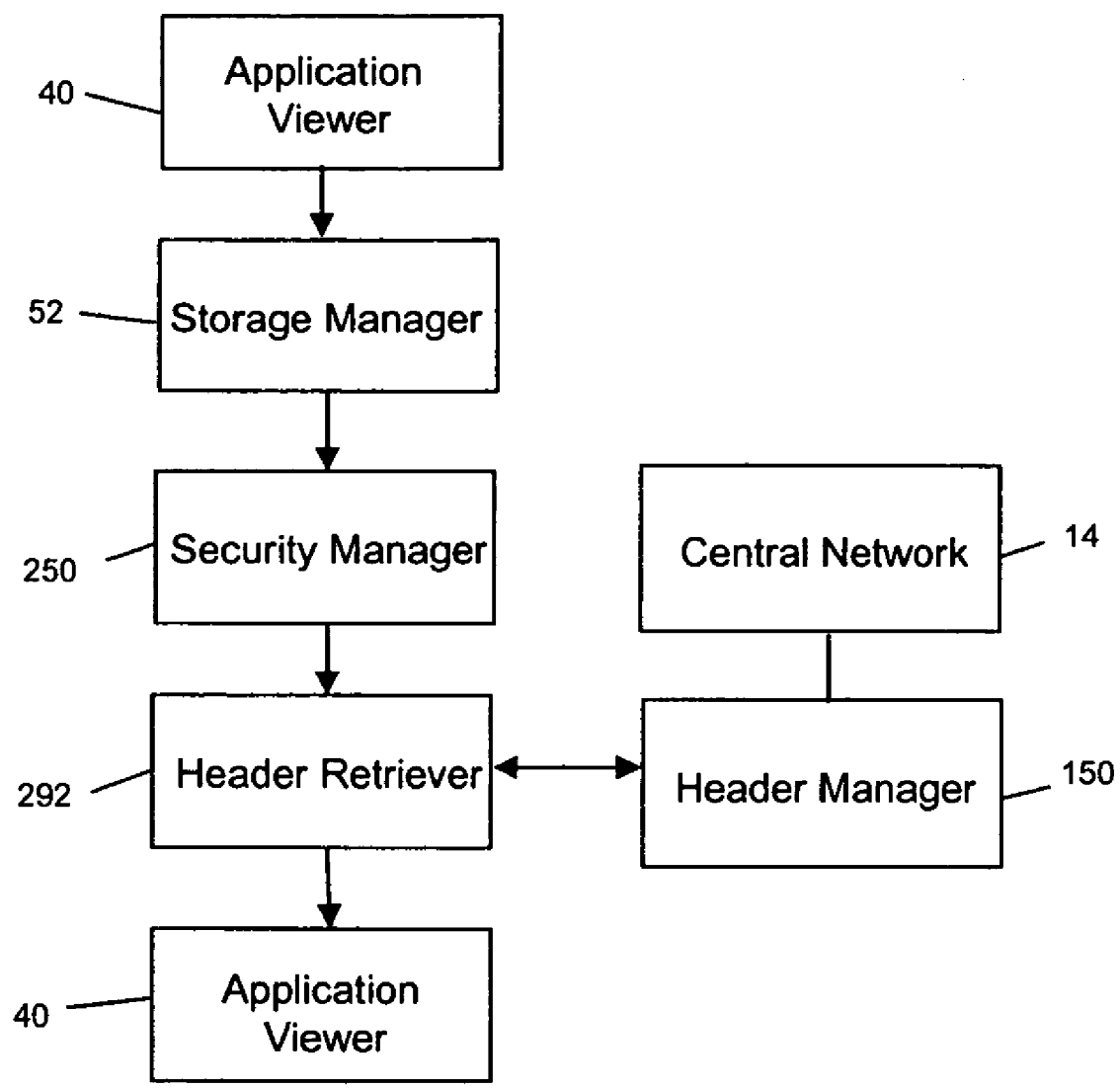
FIGS. 16A through 16C illustrate the search and add features of the system, according to one embodiment.
Figure 16B:
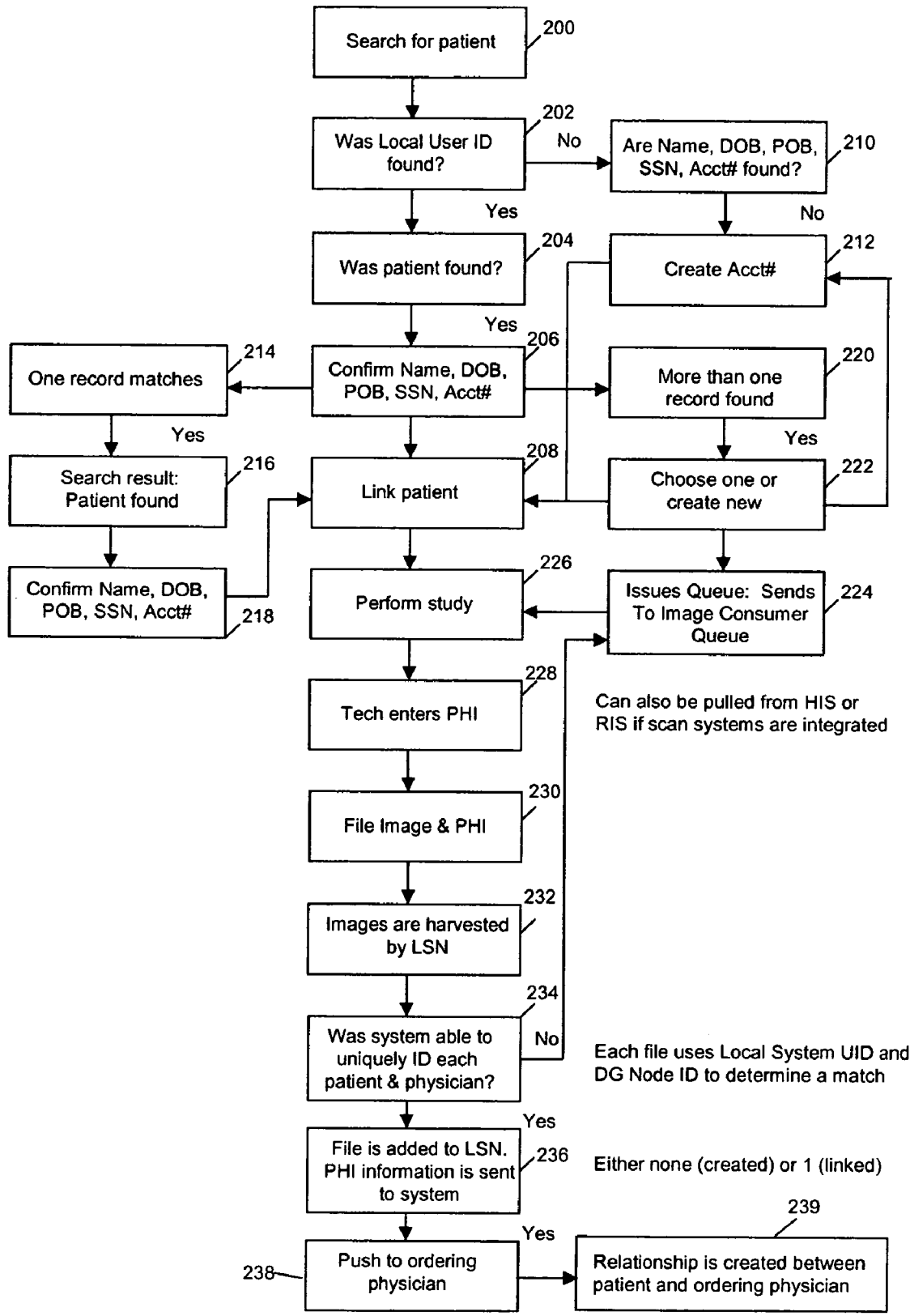
Figure 16C:
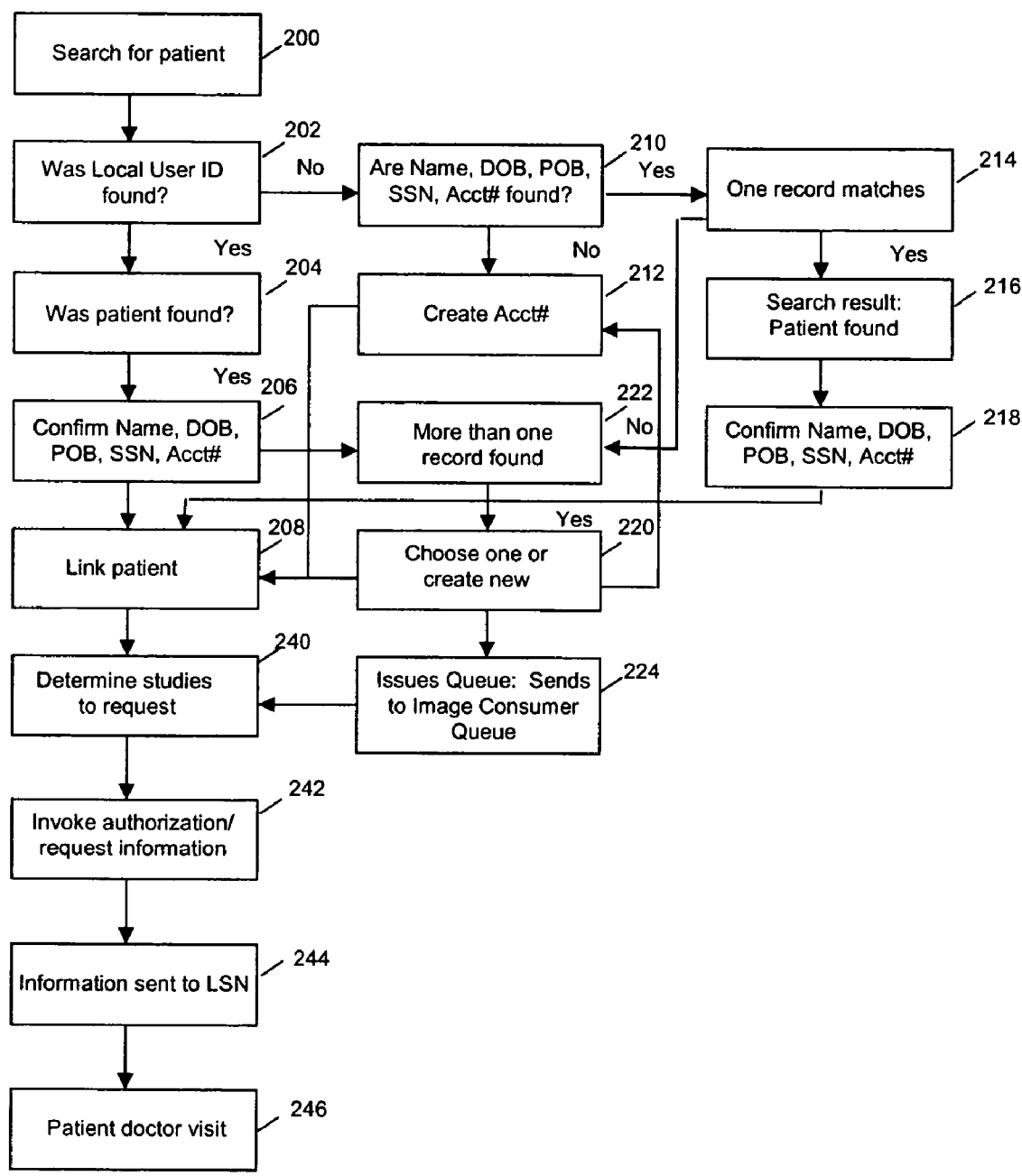

Further, the search manager 150 only searches publicly available patient information. Records that are blacked out are not included in the search. The search does not allow open searches, but rather criteria must be provided. For example, the header search may provide three different fixed criteria: (1) Central or System ID, (2) Local ID, or (3) Last Name, First Name, Date of Birth and Birth City. The patient search function allows record consumers to search for header information with which the record consumer has a trusted relationship. FIGS. 16A through 16C illustrate the search features of the present system in greater detail.

The search function may allow either the node server or the central network to be used to conduct the search for record consumers. Search results are returned in a dataset. Search columns are fixed at the database layer, but additional filters can be applied at the application server level to reduce the number of records returned. This reduces the number of indexes to maintain in the database and improve inserting new records into the tables. Search results with multiple records containing personal information will not be returned.

Node manager 35 manages the access of each node to the central network. Node manager 35 also administers the communication and transfer of records between a node and another node. Both are accomplished through poll manager 180 and this communication and transfer of records is illustrated in greater detail in FIGS. 11 and 12.

Queue manager 182 of node manager 35 allows studies transferred to record consumers not yet signed up or registered on the system to be queued until the record consumers are permitted access. Registration 178 handles nodal registration as described in more detail in FIGS. 11 and 12.

Figure 6:
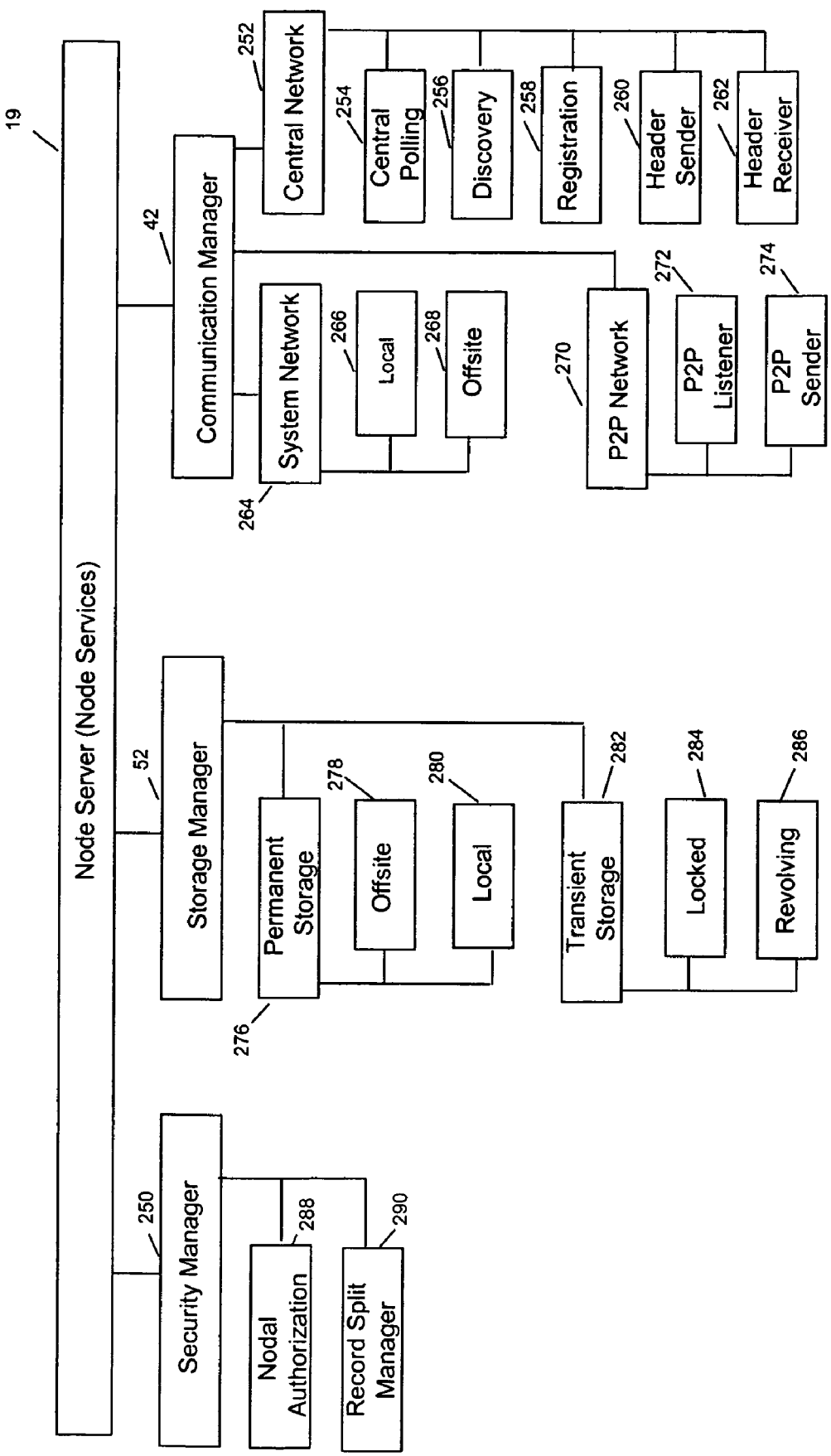
FIG. 6 is an illustration of the node server or node services component of the disclosed digital couriering system.

FIG. 6 illustrates an alternate embodiment of node server or node services 19 of the disclosed digital couriering system, also referred to as source and target nodes or storage and P2P nodes. According to this embodiment, the node server or node services 19 is comprised of basically two different types of nodes: a source node (alternately called a storage node or LSN) and a target node (previously referred to as the P2P node). Node server 19 is comprised of a security manager 250, storage manager 52 and communication manager 42.

Security manager 250 is comprised of nodal authorization 288 and record split manager 290 (also called a file handler or file manager). Record split manager 290 contains the functionality to read and update records that have been received from the network or a local harvester. Record split manager 290 contains the functionality to remove and append the header information from the record and create the unique ID to track the record on the system. Record split manager 290 is described in more detail in FIG. 20.

Storage manager 52 stores and manages the records on the local nodes. Storage manager 52 synchronizes the information between the local node and the central network to keep track of the available records on the node. Storage manager 52, in conjunction with security manager 250, administers the access to the stripped records and the headers based on the current user logged into the user application. Storage manager 52, in conjunction with communication manager 42, receives new studies from the local node manager.

Storage manager 52 is comprised of permanent storage 276 that can access both offsite storage 278 and local storage 280. Storage manager 52 is also comprised of transient storage 282 which could be either locked 284 or revolving 286. Storage manager 52 will not have a defined screen to display information but the component will be able to send its statistics to another component. Storage manager 52 will be able to generate statistics on the number of studies on the node, the storage size of the studies on the node, the study transfer history and storage limits.

Communication manager 42 has three major functions: communication with the central network 252, communication with the P2P network 270 and communication with within the system network 264 in general. Communication with the system network 264 primarily coordinates whether the communication is directed locally 266 or to an offsite location 268. The communication with the central network 252 governs communication with central polling 254, which is described in more detail in FIGS. 11 and 12.

Communication manager central network 252 also includes discovery 256. Discovery 256 is responsible for initiating a node to the network and ensuring that all nodal registration 258 (also see FIG. 13) and nodal authentication 288 is performed. This is the manner with which a node lets the network know about itself and the services that it has. Discovery 256 initiates a communication with the central network. Discovery 256 authenticates the node on the network and login status and reports the connection IP address and port. Discovery 256 communicates current storage allotment and any updates to storage since the last connection, as reported by storage manager 52. Discovery 256 also initiates the header sender 260 and header receiver 262 processes.

P2P network communication manager 270 is comprised of P2P listener 272 and P2P sender 274. P2P sender 274 directly integrates with P2P listener 272 in order to transmit files from one node to another. In order to be able to send and receive multiple files at the same time, P2P sender 274 and P2P listener 272 use thread pools and create worker threads to complete the file transfer.

P2P listener 272 listens for incoming transmission to the node and accepts data into the node for processing. P2P listener 272 must be able to accept a study from any other node on the system, and must be able to process more than one request at a time. P2P listener must check to ensure the transfer is coming from a validated node and that the transfer is authorized by a trust relationship. P2P listener 272 reports and records all failed receive attempts and decompresses a file if it has been compressed.

P2P sender 274 is responsible for sending files out over the P2P network and making sure that delivery is completed and confirmed. P2P sender 274 receives instructions from the node manager to transmit a given file to a separate node. P2P sender 274 has the ability to send multiple files at the same time to different nodes on the system. P2P sender 274 verifies the file exists on storage manager 52, and locks 284 the file in transient storage 282 for transmission. P2P sender 274 is capable of compressing a record to a temporary location. P2P sender also unlocks the record on the local storage node and reports successful completion to the central network. If an error occurs during transmission, the P2P sender 274 retries, in one embodiment, three times, before reporting a transmission failure to the central network. A space of time, in one embodiment, five minutes, occurs before each retransmission attempt.

Figure 7:
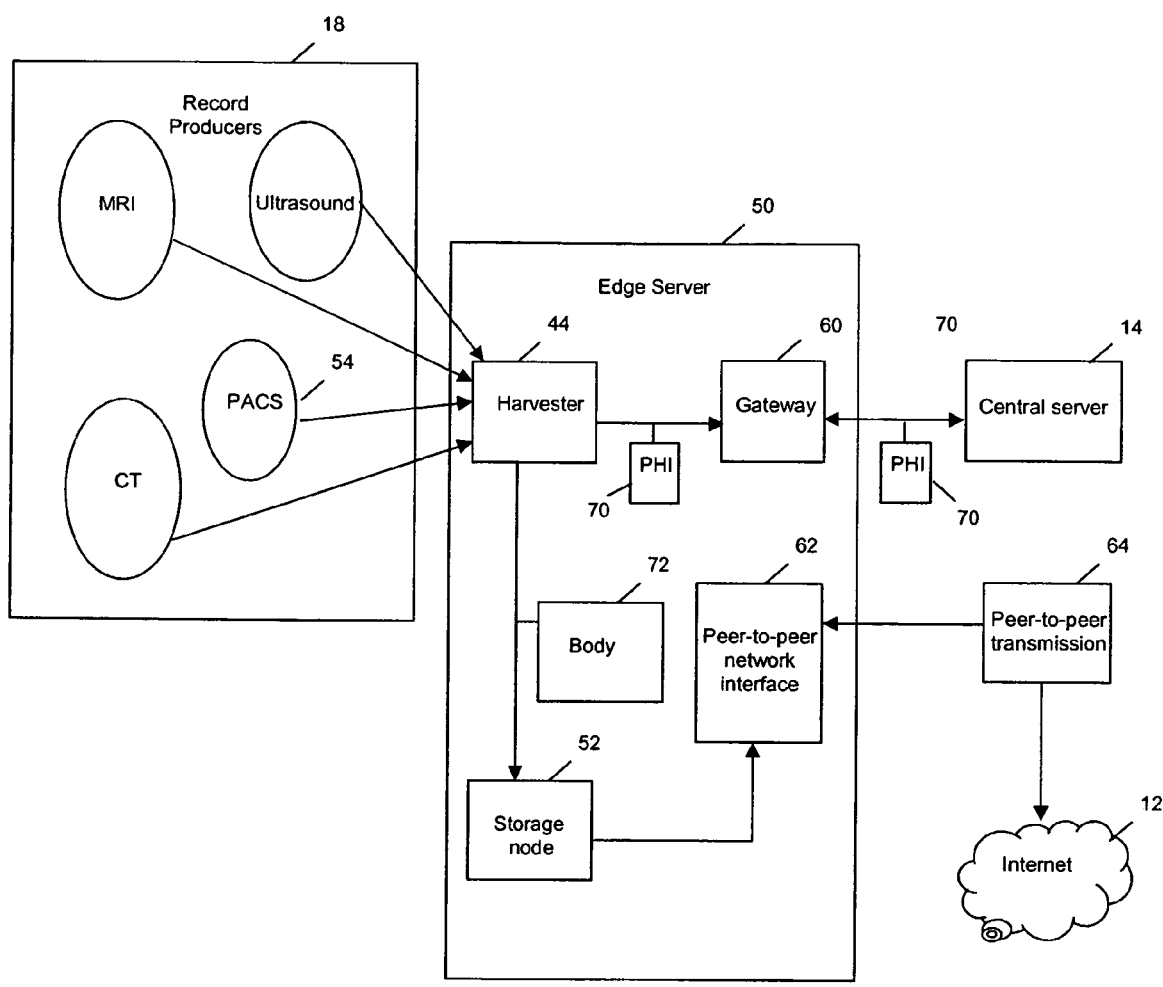
FIG. 7 is an illustration of one embodiment of the record producer component of the disclosed digital couriering system.

FIG. 7 illustrates the Record Producer 18 portion of the system. The Record Producer component is a node on the network whose primary responsibility is to supply records to the system, also referred to as the source node. The Record Producer 18 does not upload the entire record directly to the Central Server 14, but only sends the personal information (PHI) 70. The record remains on the record producer 18's storage node 52 until it is requested, or the requesting record consumer (physician) is identified and the body 72 of the record (the non-personal information) is pushed to the record consumer's (physician's) node. It is noted here that this pushing of the body 72 of the record to an identified record consumer, before the record is requested, is a novel feature of the disclosed system and method. Other features shown in FIG. 7 are described in further detail below.

Figure 8:
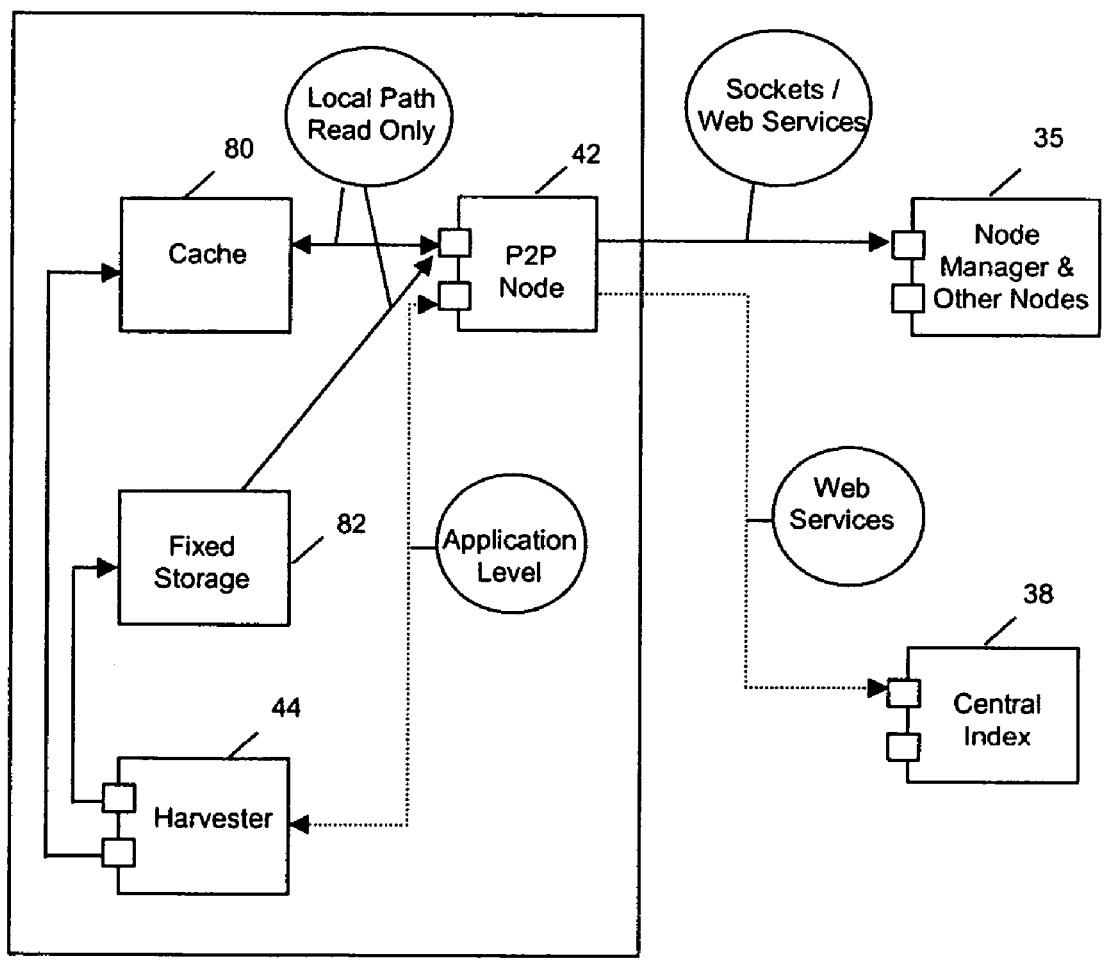
FIG. 8 is a further illustration of one embodiment of the record producer component of the disclosed system.

As shown in FIG. 8, the Record Producer 18 component integrates the harvesting or acquisition of records, registering of records to the Central Index 38 and pushing these records out to other nodes on the network. The Record Producer 18 has both cache storage 80 as well as fixed storage 82. The fixed storage 82 is read-only by the P2P Node 42. This means that all fixes coming in are written to the local cache 80 instead. As shown in FIG. 8, the only way for files to move to the fixed storage 82 is for the harvester 44 to put them there. Also, as shown in FIG. 8, all communication to all other nodes (the outside world) is done through the P2P network node 42. This includes both socket and web service traffic. As shown in FIG. 8, the record harvester, described below, communicates directly with each node and the Central Index through the node component.

Figure 9:
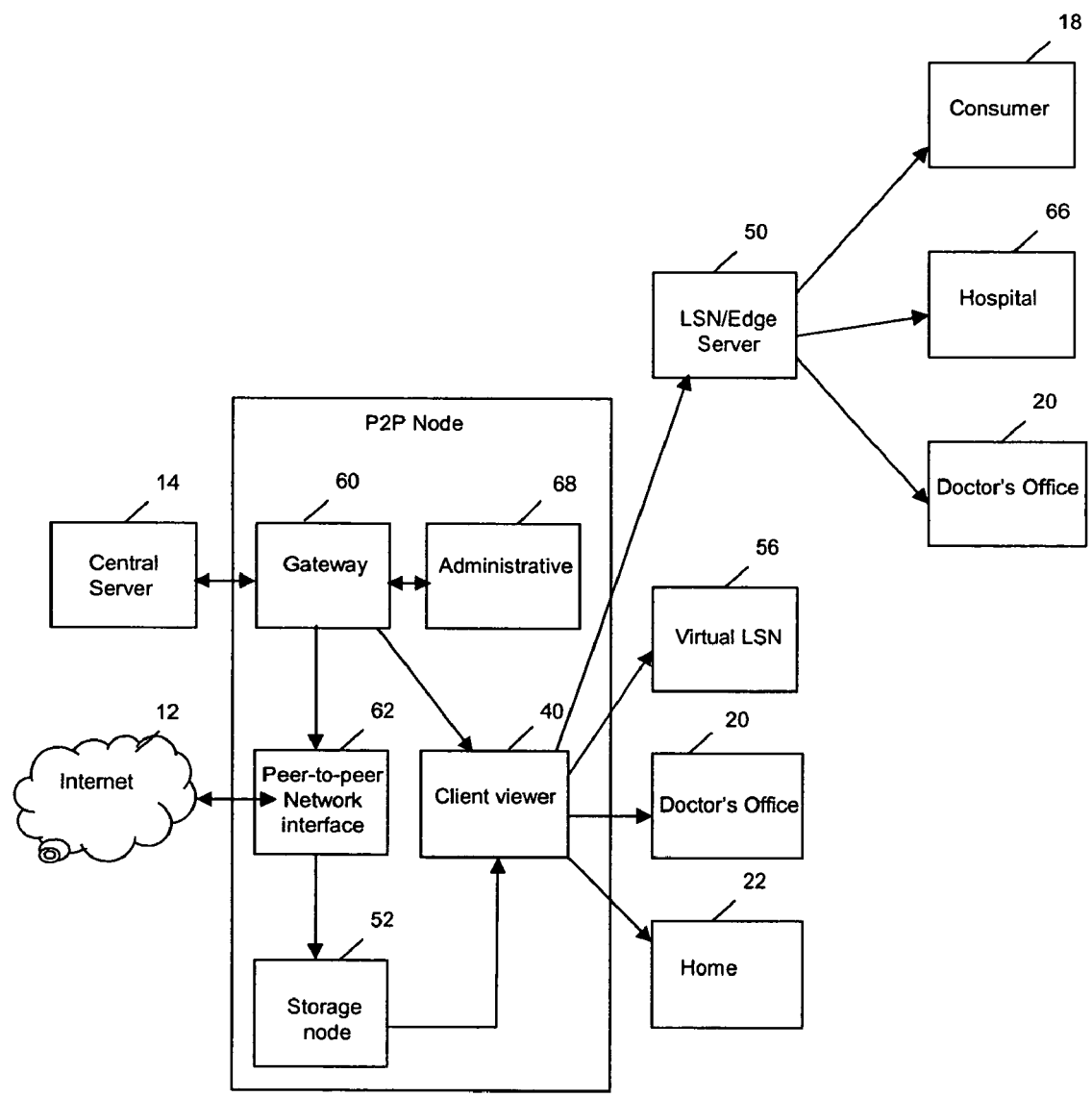
FIG. 9 is an illustration of one embodiment of the record consumer component of the disclosed system.

Record Consumers make up the remaining nodes on the system, which are also referred to as target nodes. As shown in FIG. 9, these nodes (P2P, network or target nodes) 42 are set up to be able to receive and send records, but they also contain the viewing software, shown as client viewer or viewing application 40, for recombining the PHI with the body of the record in order to present a complete record to the record consumer. As described in detail below, the record consumer can also search for patients and allow another record consumer to invoke his authority to request that records be sent to his node.

Figure 10:
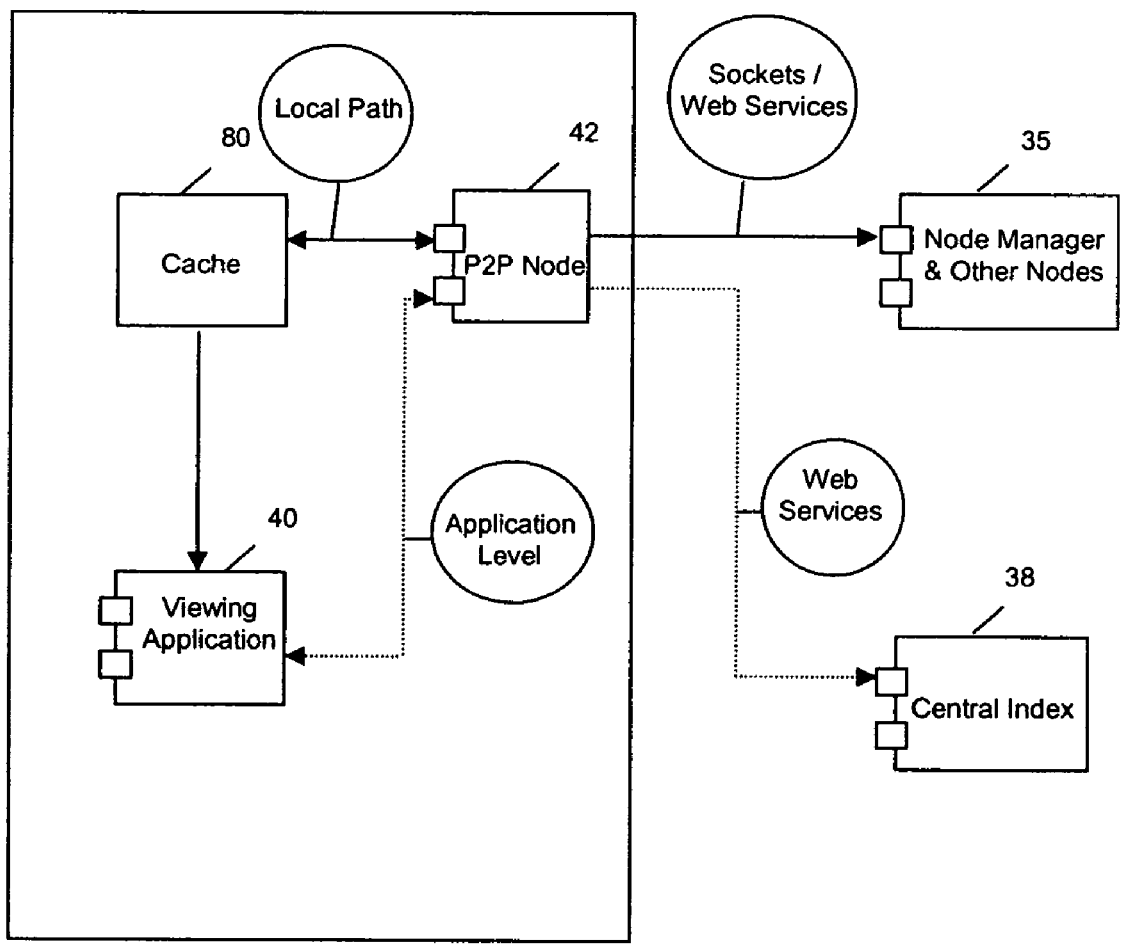
FIG. 10 is a further illustration of one embodiment of the record consumer component of the disclosed system.

FIGS. 9 and 10 illustrate the functionality of the record consumer component of the system and its interaction with other components of the disclosed system. The viewing application or client viewer 40 shown in FIGS. 9 and 10 includes the node component and ensures all communication is tracked and logged.

Each peer or node that joins the network must register with the Central Server 14 before it can communicate with other nodes in the network. The node is then authenticated and the Central Server 14 monitors which nodes are connecting. According to the disclosed system, there are two modes with which nodes can connect, as a Record Consumer (Network Node) 42 or as a Record Producer 18 (with Storage Node 52).

When an organization, whether it be a doctor's office, hospital, or other record producer, becomes a "member" of the system, the facility, its physicians and staff must be added or enrolled in the system. The enrollment process for a record consumer, such as a doctor is fairly simple. In one embodiment, in order to connect as a Record Consumer, a physician ID is required to set up and begin operations. In other embodiments, other criteria would be acceptable, for example, a patient ID or system account number.

Figure 11:
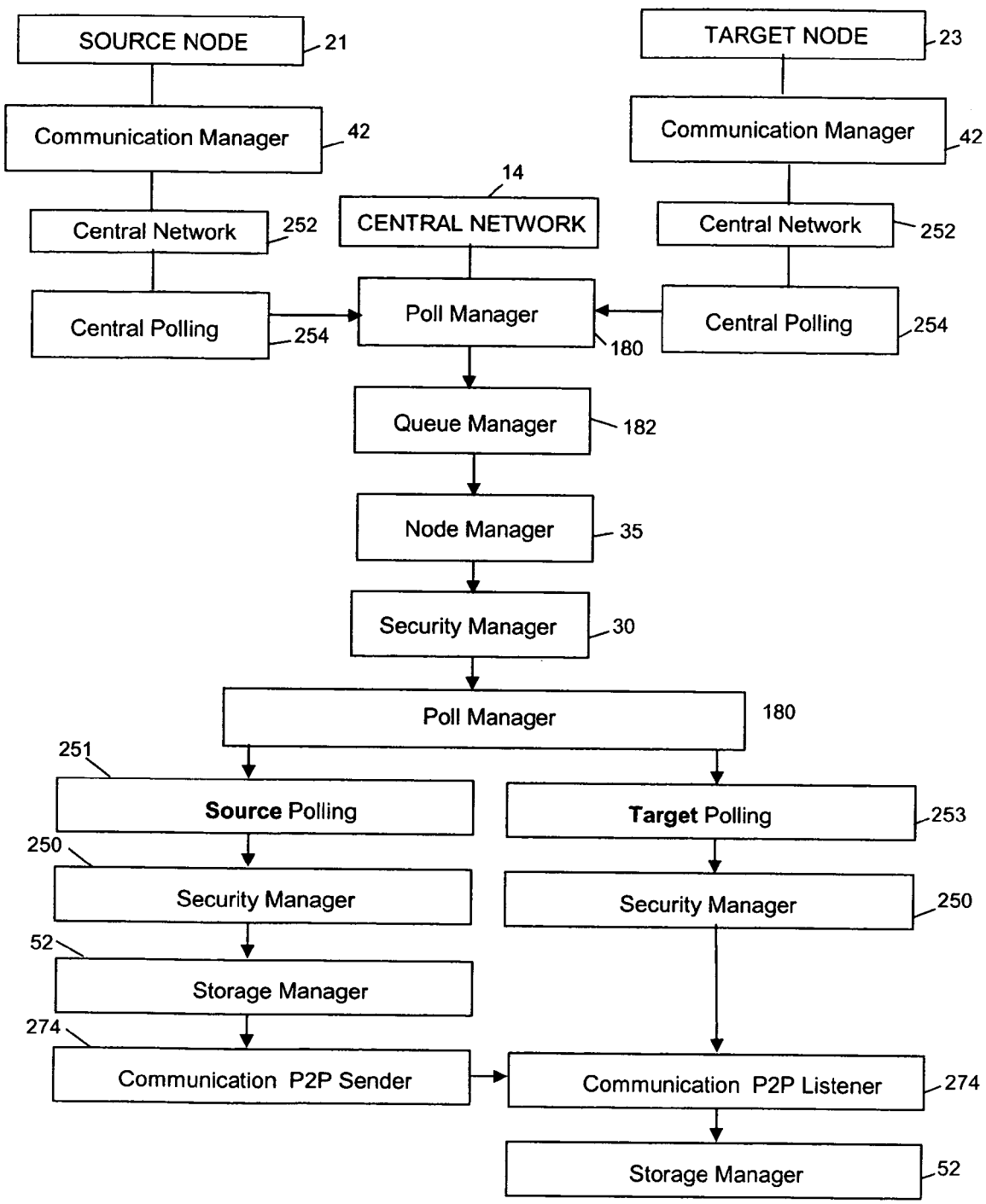
FIG. 11 illustrates one embodiment of the communication pathway between the central network and the nodes of the disclosed system.
Figure 12A:
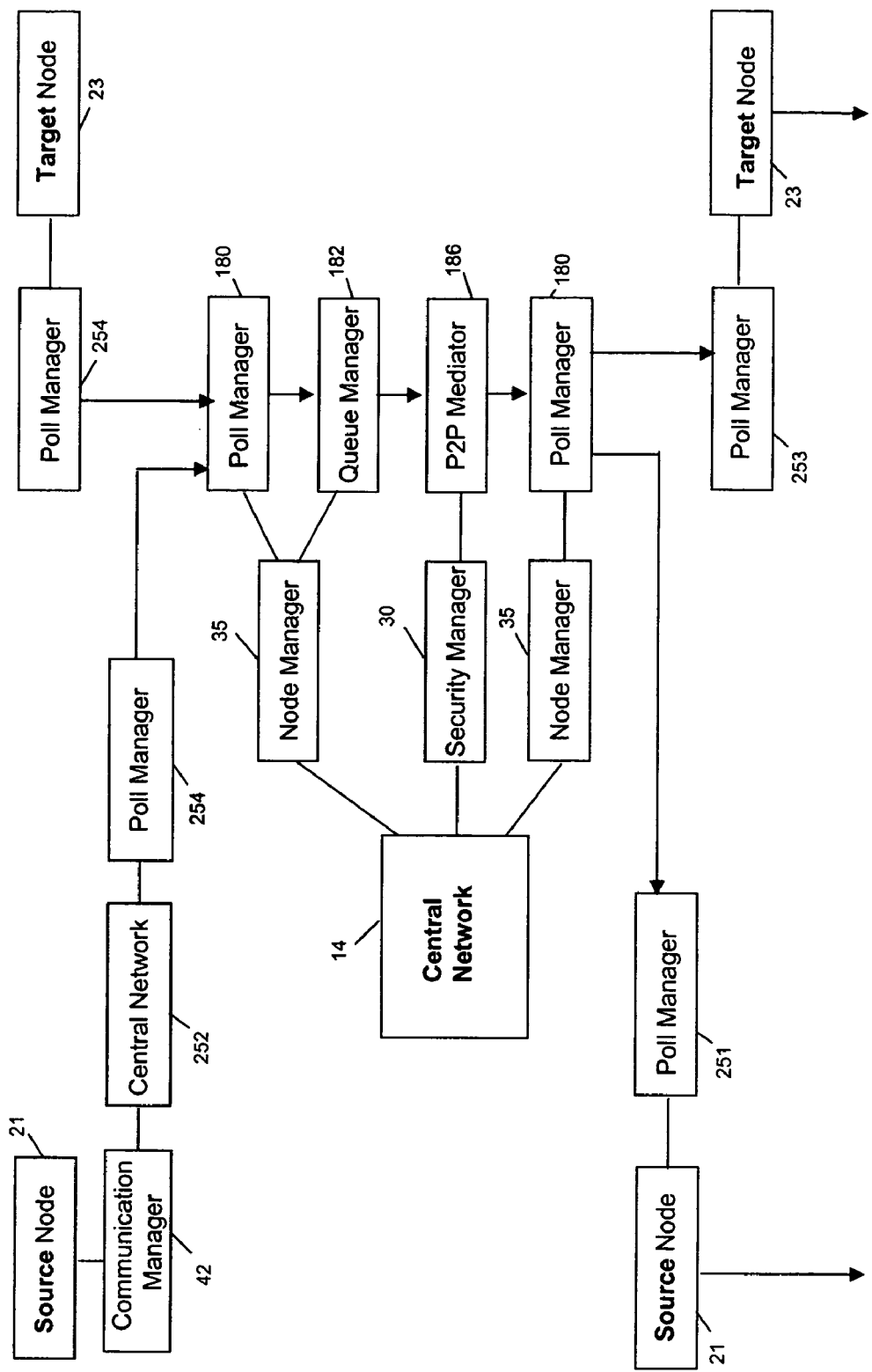
FIGS. 12A and 12B further illustrate one embodiment of the communication pathway between the central network and the nodes and transfer of information between the central network and the nodes and between the nodes.
Figure 12B:
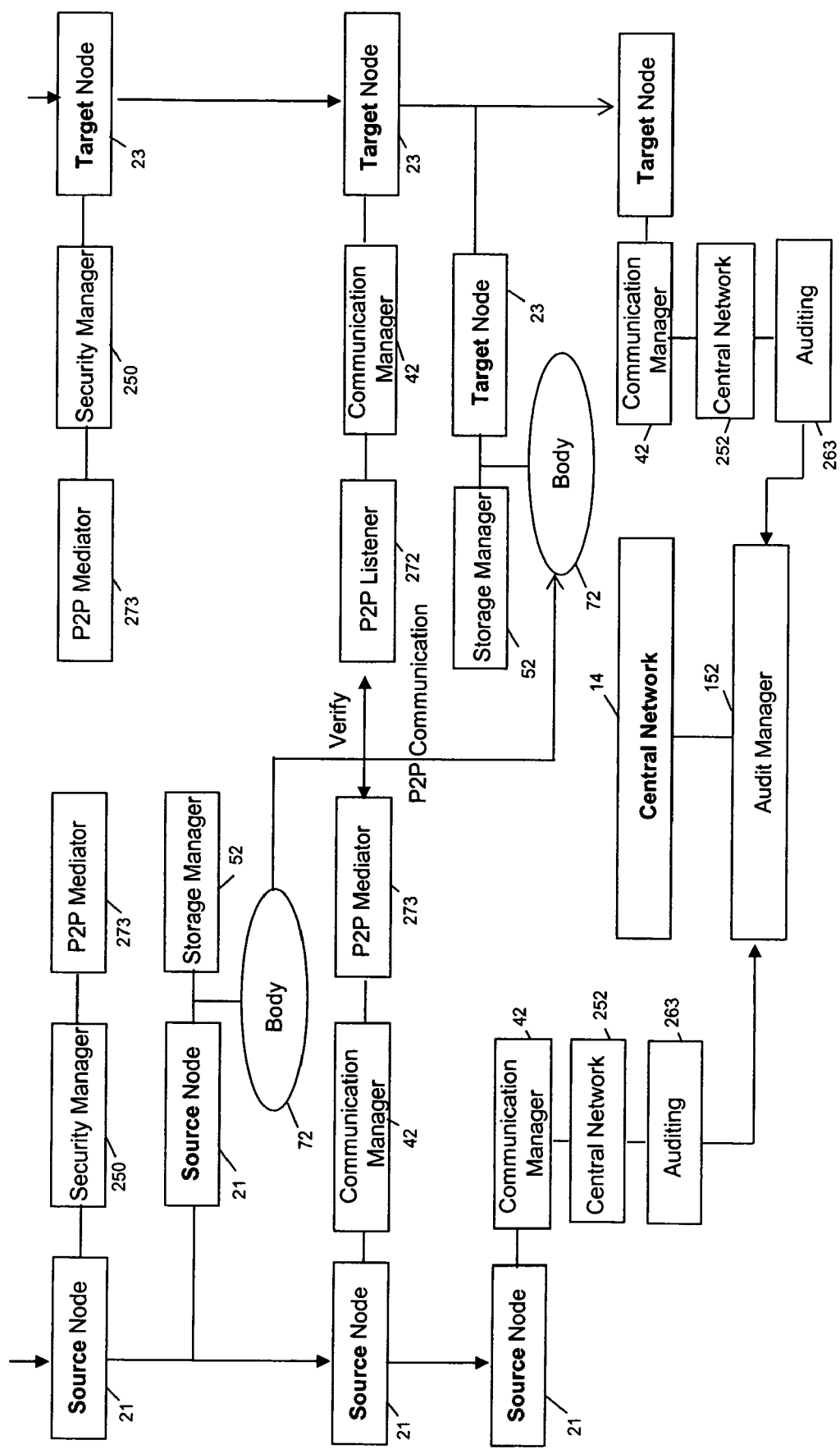

FIGS. 11 and 12A-12B illustrate alternate embodiments of the communication pathway between the central network and the nodes of the disclosed system (here, source node 21 and target node 23) and the P2P communication between nodes, including in FIG. 12B, transfer of information between the central network and the nodes and among the nodes. The following description of the components refers to all three figures in conjunction. The basis of all communication between the central network 14 and the nodes is the poll managers. The nodes have a poll manager with two aspects, central polling 254 to send communications to the central network 14's poll manager 180, and source polling 251 or target polling 253, depending on whether the node is a source node or target node, for receiving communications from the central network 14's poll manager 180.

Node manager 35 is a group of web services and socket connections that control the nodes in the network. Most functionality is managed with the node making requests to the node manager for login or configuration information. Node manager 35 relays the IP address and port number to the other nodes. Node manager 35 transfers record lists from the nodes to central network 14. Node manager 35 is responsible for determining whether there is availability to transfer a record. Node manager 35 also sends records in the queue when the recipient logs in. Transfers are queued in queue manager 182.

As shown in FIG. 12A, node manager 35 communications with the other nodes through the P2P network via the P2P mediator 186. The central network P2P mediator 186 in conjunction with the nodal P2P mediators 273, facilitate peer-to-peer network communication and manage all of the nodes that can connect to the network. The management of these nodes is what maintains the network and controls the traffic across the network. P2P mediator 186 allows node to login and authenticate to the central network using a node ID and credential key. P2P mediators 186 and 273 allow nodes to check in to let the system know that they are online and active. The central network 14 stores this information in the database.

As shown in FIG. 12B, P2P mediator 273 in conjunction with P2P listener 272 allows the transfer of a stripped record or body 72 from one node to another. The P2P mediators 186 and 273 also indicate to a source node that a record should be transferred and give the destination node ID, IP address and port. P2P mediators 186 and 273 also supply configuration information to an authenticated node and allow configuration information to be viewed from an administrative screen. Auditing function 263 tracks the transfer of these stripped records from one node to another. Also, the auditing 263 updates status based on failed attempts, successful attempts and pause/hold (retry) attempts.

Figure 13:
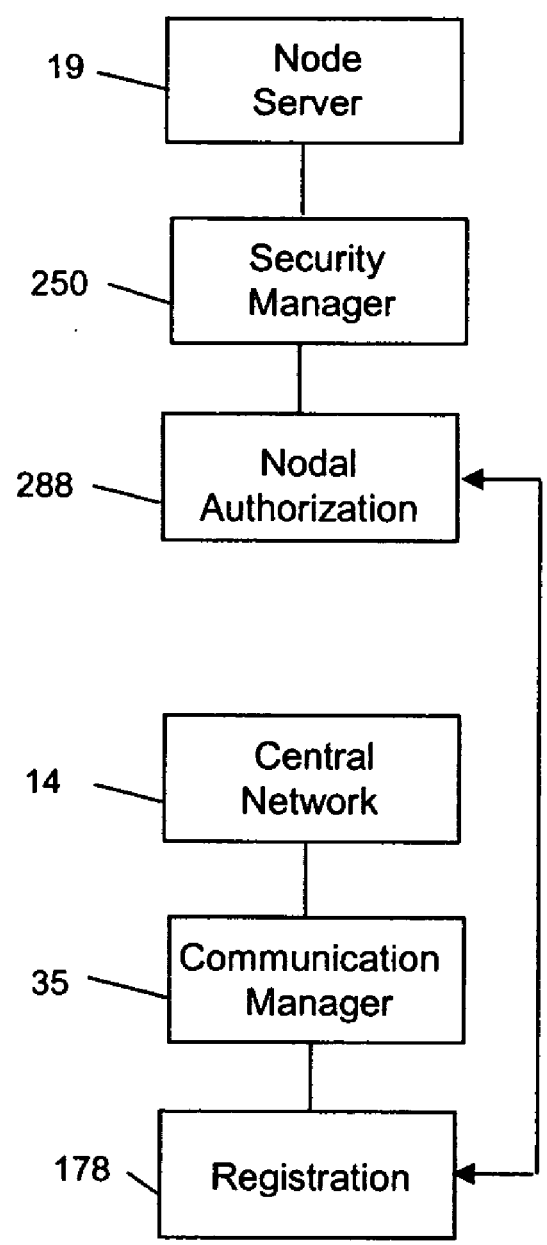
FIG. 13 illustrates nodal registration on the system, according to one embodiment of the disclosure.

FIG. 13 illustrates nodal registration and authorization on the system, according to one embodiment of the disclosure. The authorization component processes new record consumers on the system and verifies that the record consumer should be allowed access to the system. One particular embodiment of this process, described below, by way of example only, illustrates this process in greater detail.

Access to the system may be tiered. For example, three tiers may exist: (1) no access, (2) tier 1 access and (3) tier 2 access. If no access is granted, the account is not permitted to gain access to the system and does not have permission to authenticate and activate a node. If Tier 1 access is granted, the record consumer can activate a node and log in to the system. However, the record consumer is only allowed to view a record that has been pushed to him preemptively. The record consumer, in Tier 1, is not allowed to request records, forward records or create a chain of trust with any other record on the system. If Tier 2 access is granted, all functions are allowed for this record consumer. The record consumer has qualified or provided the required documentation to allow for a chain of trust to be created as well as request and forward records on the system. Either Tier 1 or Tier 2 access will allow access to download the user application and node software (see FIG. 23A).

Figure 14A:
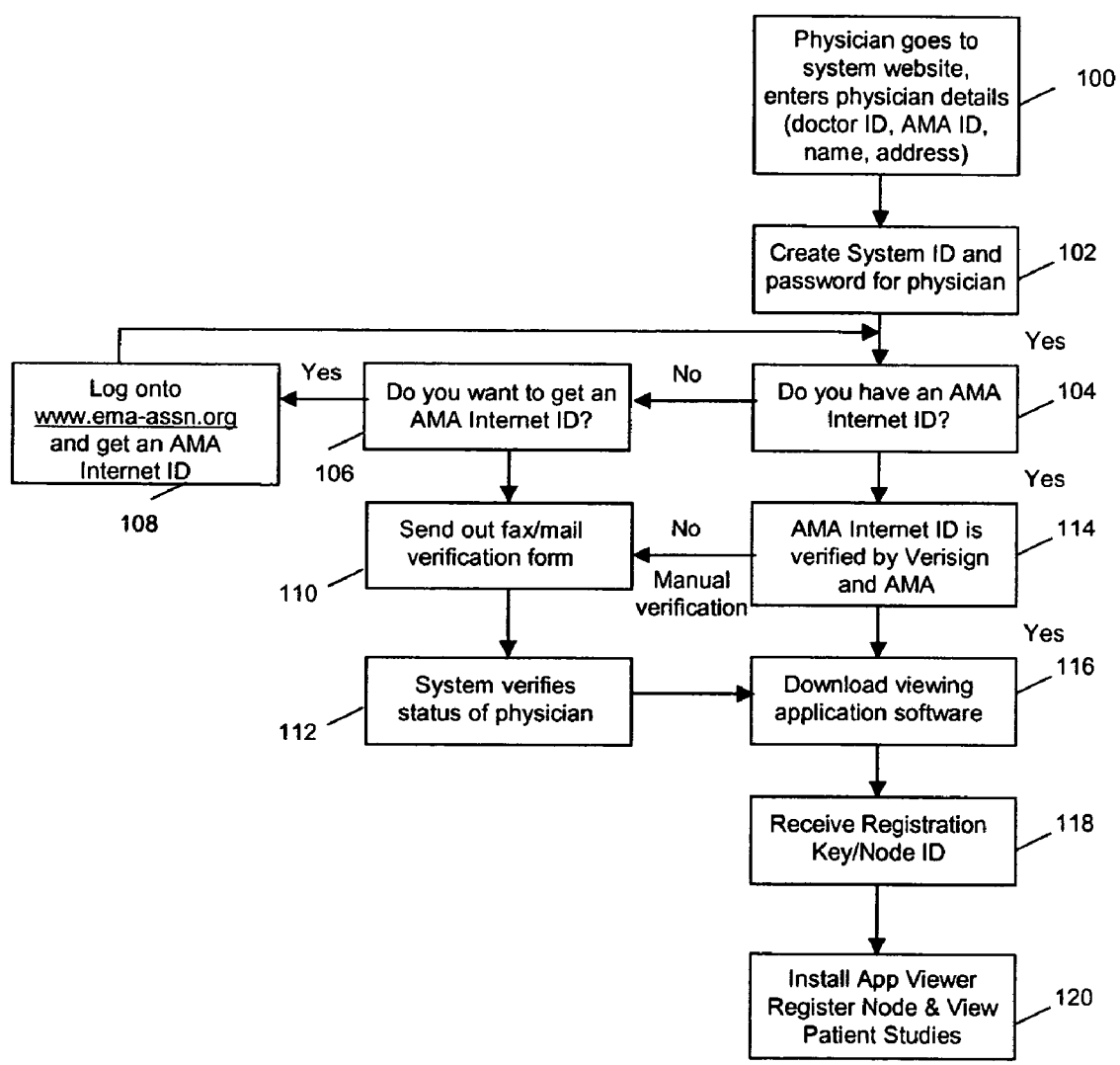
FIGS. 14A and 14B are flowcharts illustrating registration of record consumers and record producers on the system, according to one embodiment.

FIG. 14A is a flowchart illustrating record consumer registration on the system, according to one embodiment. By way of example only, record consumer registration is illustrated by physician enrollment on the system. According to the present disclosure, the terms doctor and physician are interchangeable. In step 100, the physician accesses the system's website and enters physician details, such as doctor ID, American Medical Association (AMA) ID, name and address, as well as any other information requested by the system.

The system then creates an ID and password for the physician in step 102. In one embodiment, in step 104, the system asks the physician if he has an AMA Internet ID. If not, in step 106, the system asks if the doctor would like to get an AMA Internet ID. If so, the physician, in step 108, is either redirected to www.ema-assn.org or is asked to log on to that website and acquire an AMA Internet ID.

If the physician does not want to obtain an AMA Internet ID, in step 110, a fax or mail verification form is sent to the physician, and based on the information on this form, verifies, in step 112, the status of the physician. However, if the physician in step 114, had or obtained an AMA Internet ID, the physician in step 116 is permitted to download the Client Application, also called the Viewing Application, software. In step 118, the physician receives a registration key and node ID, and then, in step 120, the Client Application, including, for example, the applications viewer, register node and view records software applications, are installed on the physician's server. This physician is now a network node on the system and can request and view records.

If an entire office or hospital is enrolling onto the system, the software can be loaded on each computer via a download or CD. Then an individual administrator must set up the list of valid physicians and other users. According to one embodiment, only physicians and patients have the initial ability to view the records. In order for non-physician and non-patient users of the system to view records, association between the physician and the user must be established as a proxy of the patient. (FIG. 28) Thus, in the disclosed system the explicit trust relationship between the physician and the proxy user must be defined and validated.

Figure 14B:
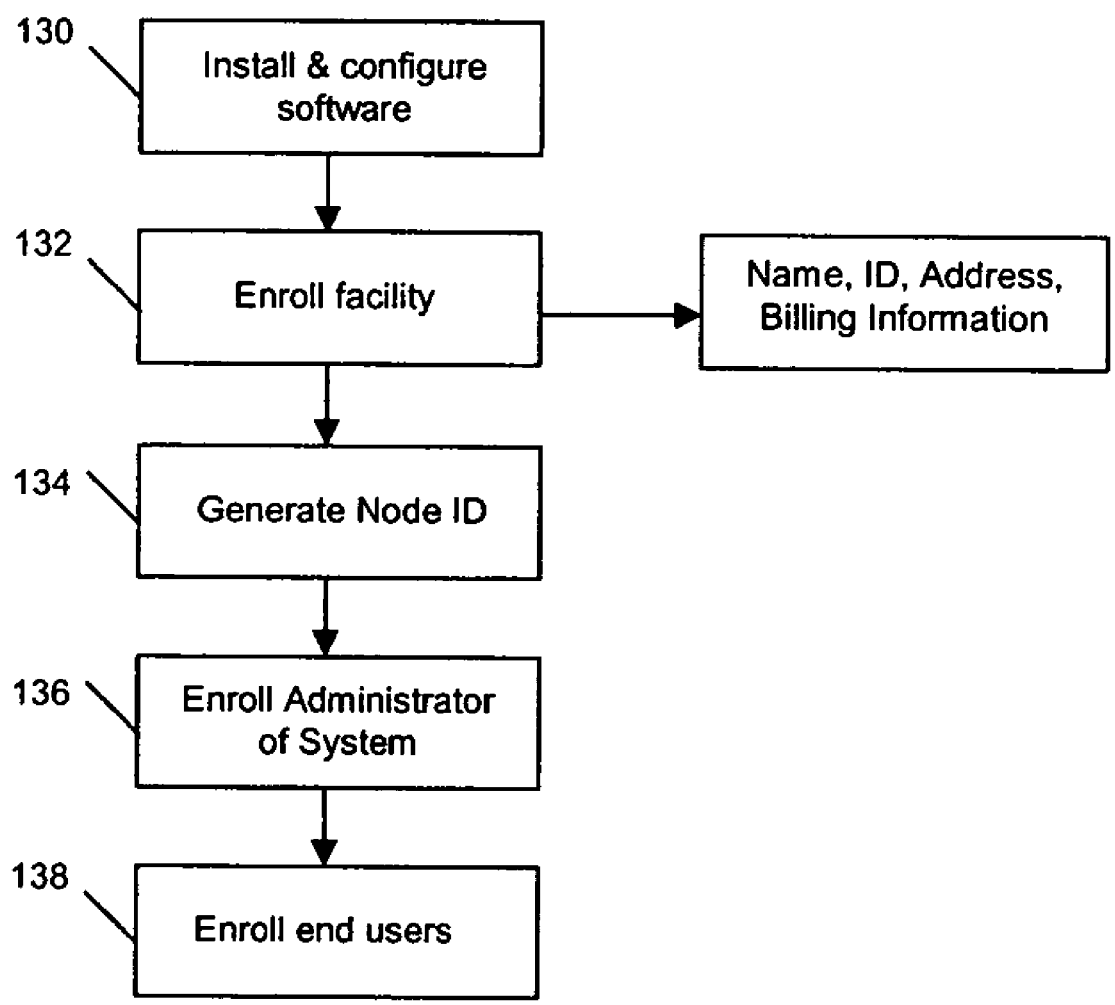

FIG. 14B is a flowchart illustrating record producer registration on the system, according to one embodiment. In order to connect as a Record Producer, the Central Server first needs to authorize upon connection and then set up security certificates for the entity. An entity or facility that serves as a Record Producer must assign an administrator and then add end users who will add or search for records. In step 130, the software is installed and configured. Then, in step 132, the facility is enrolled by providing requested information, including facility name, facility address, facility ID, billing information, and any other requested information.

Next, in step 134, the system automatically generates a Node ID for the facility. In step 136, an administrator is enrolled. The administrator is the individual or group of individuals responsible for configuring and maintaining the application at the Record Producer. Finally, in step 138, the end users are enrolled. The end users are the day-to-day users of the system. The administrator is asked to enter the username, password, the node ID and assign a role or access rights. All other parts of the Storage and Network Nodes function similarly as far as sending and receiving file from other nodes and are controlled through the Central Server.

Figure 15A:
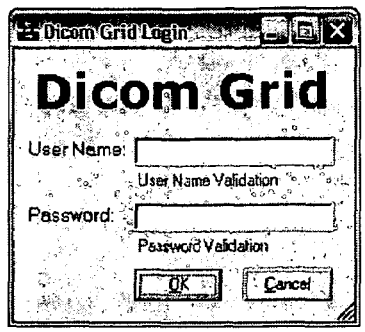

FIG. 15A is an example of the first screen the user encounters when launching the Client Application on the system from his computer. The login screen will allow a user to access the system by entering his Username and Password as shown in FIG. 15A. This login process defines the user gaining access to the system and which node or nodes he is affiliated with. Once the user is logged in, the user will have the ability to view information based upon his access rights. Once the user is logged in, the user can search for a patient to see if he is already affiliated with the system.

FIG. 16A generally illustrates the communication pathway necessary to add and search for existing record owners (e.g., patients). The user application or viewer application 40 is the component record consumers use to view the current records available to that record consumer. Viewer application 40 allows multiple records to be loaded simultaneously in the application to allow side by side and other types of comparisons.

The viewer requires a user to log in before the application can be used. Multiple viewers can be open using the same or separate login credentials. The viewer will display information of records trusted to the record consumer based on the trust hub for that record consumer as shown in FIG. 15K. Only records trusted to the record consumer that are found on the target node will be displayed in the application. Record consumers can request records that do not exist on the target, if the record is included in the consumers' trust hub (FIG. 26) or if they have received a proxy (FIG. 28). Records can also be forwarded to another record consumer as shown in FIG. 27. All records viewed are logged in the central network as described above.

FIGS. 16B and 16C are flowcharts illustrating the search and record creation or viewing process for the record producer (FIG. 16B) and the record consumer (FIG. 16C). As shown in FIG. 16B, and by way of example only using the medical imaging field, when a patient comes to a record producer facility to have a record made, in this case, a medical image, the record producer search requests the patient to complete the required HIPAA release form. Once the form is received by the record producer, the record producer searches for the patient to see if he is already affiliated with the system before adding new records. Various algorithms known in the art are used to optimize and rank search results for patients. These different search paths depend in part on the amount of information supplied to the search component.

Figure 15B:
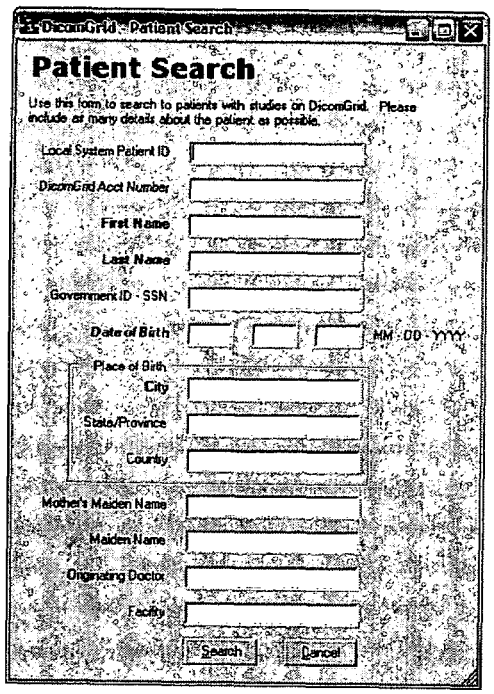

Referring now to FIGS. 16B and 16C, the search process for both the record producers and record consumers in step 200 begins by the record producer viewing a screen, such as that shown in FIG. 15B. If the patient has previously been entered into the system, the patient will have a System ID number and will already be linked to the system. Thus, only the System ID number needs to be entered into the system. If the patient has been to the facility before, the patient may have a local account number for the facility's system (Local User ID) and that is entered into the search request in step 202.

Figure 15C:
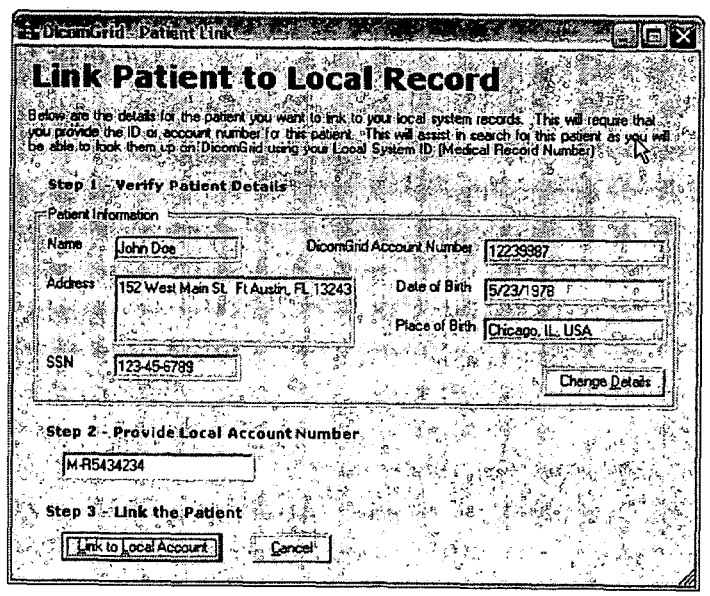

If the patient is found in step 204, then in step 206, the record consumer or record producer confirms the patient's personal information, which may include, but is not limited to, the patient's social security number, date of birth, place of birth, mother's maiden name, requesting or originating record consumer, facility name, patient's maiden name, patient's address and patient's phone number. The patient is the linked to the system in step 208. Linking of the patient to the system comprises associating a Local User ID with a System ID. An example of the screen for linking the patient to a Local User ID is shown in FIG. 15C.

Figure 15D:
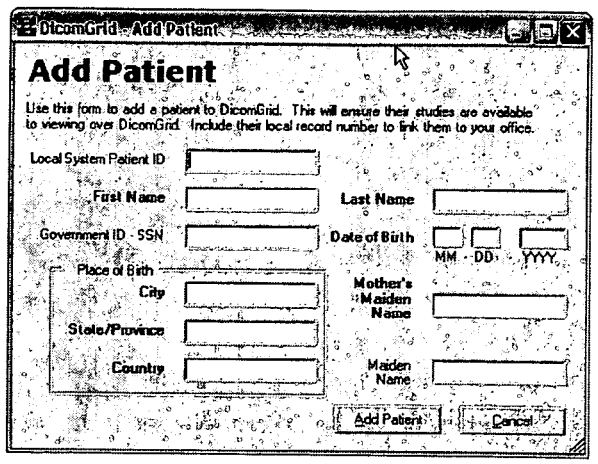
Figure 15E:
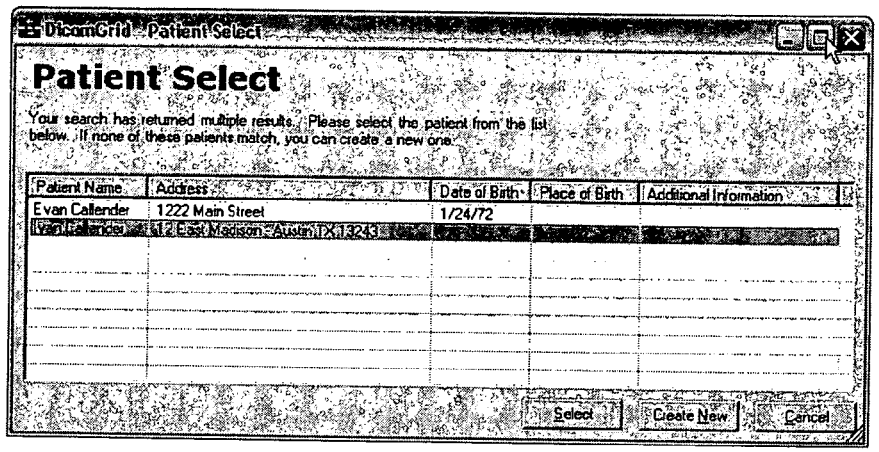

If the patient does not have a system account number or Local User ID, the system then searches for the patient's personal information, which is entered into the search form shown in FIG. 15B. If the patient is not found in step 210, the patient is then added and an account created in step 212. An example of the screen for adding a patient is shown in FIG. 15D. If the search in step 210 results in a single record match, as shown in step 214, the patient's personal information, the patient is found in the system in step 216 and the patient's personal information is confirmed in step 218. The patient is then linked to the system in step 208.

If the search in step 210 yields multiple record matches, as shown in step 220, the listing of possible matching records are displayed, and the user chooses the correct patient from the list in step 222 and the patient is linked to the system in step 208. An example of the patient select screen is shown in FIG. 15D. If in step 222, none are correct, the user creates a new account in step 212. When multiple matches are generated from a search, the result is sent to the issues queue to resolve the issue of personal information generating multiple results.

The issues queue is local to a single node and includes a list of all items that cannot be resolved programmatically and require review and intervention by a person. Examples of issues sent to the issues queue include, but are not limited to, records that have the incorrect format; records where the record consumer has been deemed invalid; records where the patient cannot be linked to the system; records where the patient personal information cannot be linked to a single System ID (multiple results); records that have been requested but are not longer on the local storage cache.

Figure 15F:
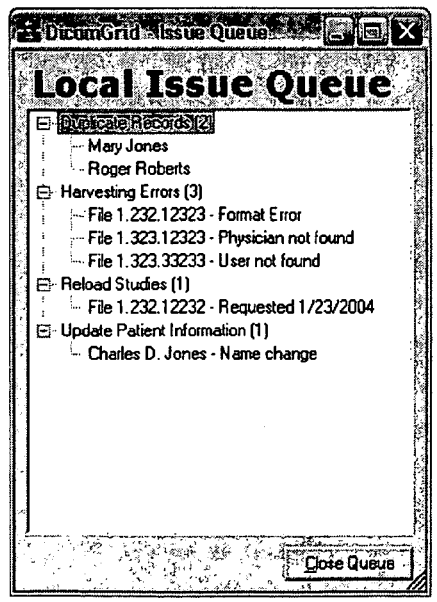
Figure 15G:
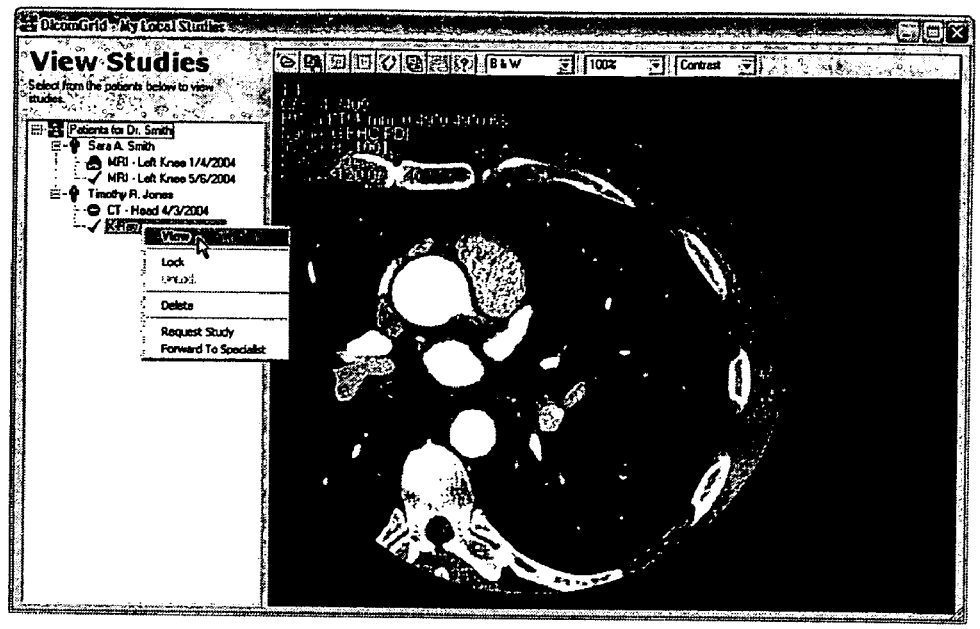

FIG. 15F is an example of the local issues queue. The functionality of the issues queue is envisioned to include one queue per node for all issues. Items are automatically pushed to the issues queue if they cannot be routed to the record consumer. There are automated "wizards" to assist the end users' walkthrough and to resolve the issues. If the item is flagged for correction, the record is routed to the record producer. If the local node cannot resolve the situation, the issue can be forwarded to the Central Server for resolution.

Referring now to FIG. 16B, once the patient has been entered, selected and linked to the facility, the patient undergoes whatever examination or test or other treatment that has been requested by one or more record consumers, as shown in step 226. Once the procedure is complete, a record is created and PHI is associated with that record in step 228.

As described above, the record consists of two parts: the personal information or PHI, and the Body. The personal information may include, but is not limited to, patient name, date of birth, sex, local user ID, record consumer's name to whom the record will be pushed, place of birth, address, phone number and social security number. The record will also contain certain information about the record producer, including, but not limited to, entity name, entity address, date and time record was created, and brief description of the record.

Once the record has been created, the record is filed in step 230 and may be loaded onto a PACS or other storage system and that system serves as the local storage system. In other embodiments, for example, for facilities that do not have a PACS or other storage capabilities or for facilities that do have storage capabilities, but find that storage on the facilities local system is not practical or desired, the records can be stored on the Central Server's storage node which will serve as the local storage node and maintain the record, as described above. In either case, the records are harvested from the PACS or other storage system in step 232. Steps 234 through 238 are described in more detail with reference to FIG. 18.

Figure 17:
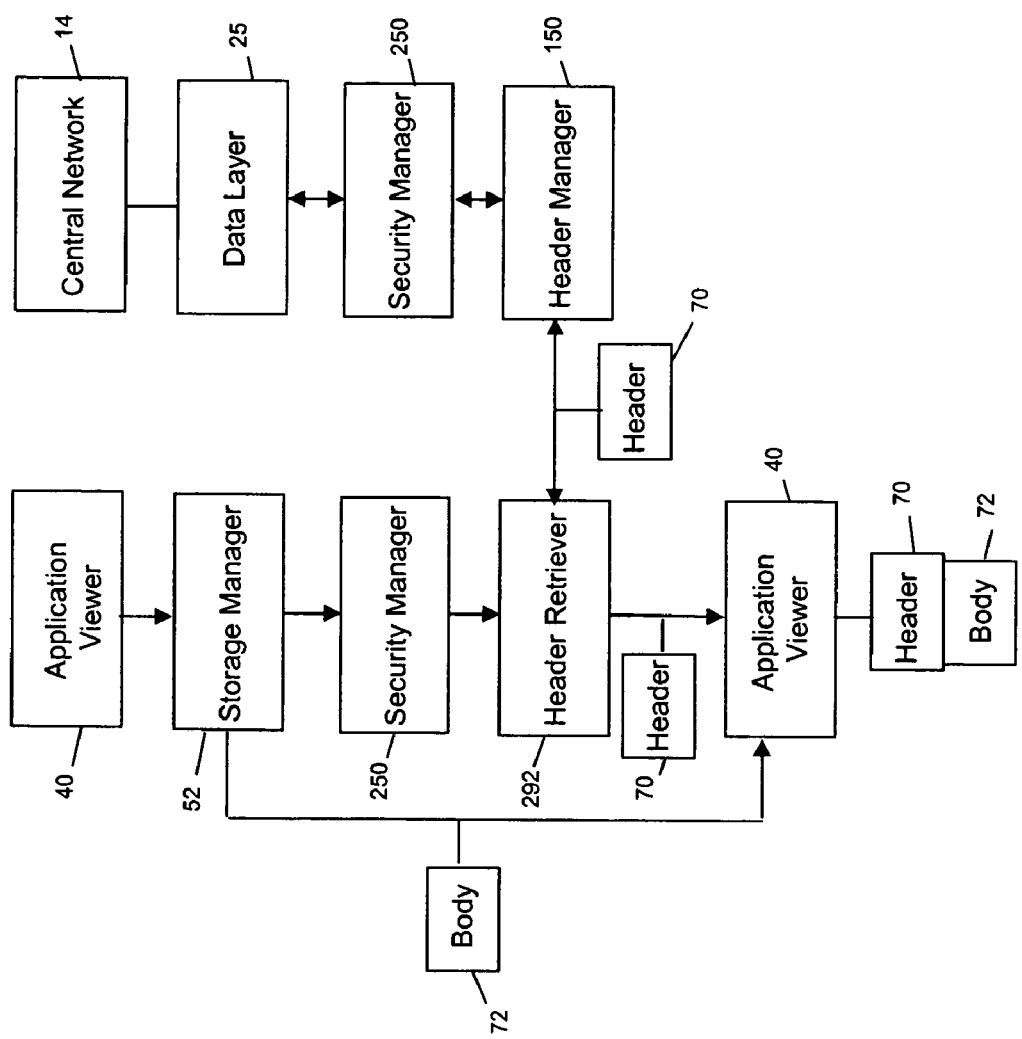
FIG. 17 is a basic illustration of how records are digitally couriered according to the present disclosure.

FIG. 17 is a basic illustration of how records are digitally couriered according to the present disclosure. As shown in FIG. 17, the body 72 of the record being stored in storage manager 52 is transmitted via P2P communication to the record consumer's application viewer 40. The PHI or header 70 is transferred from the header manager 150 in the central network 14 to the header retriever 292 in the target node and then transferred to the application viewer 40 of the record consumer, where the header 70 and body 72 are recombined to form a complete record.

Figure 18:
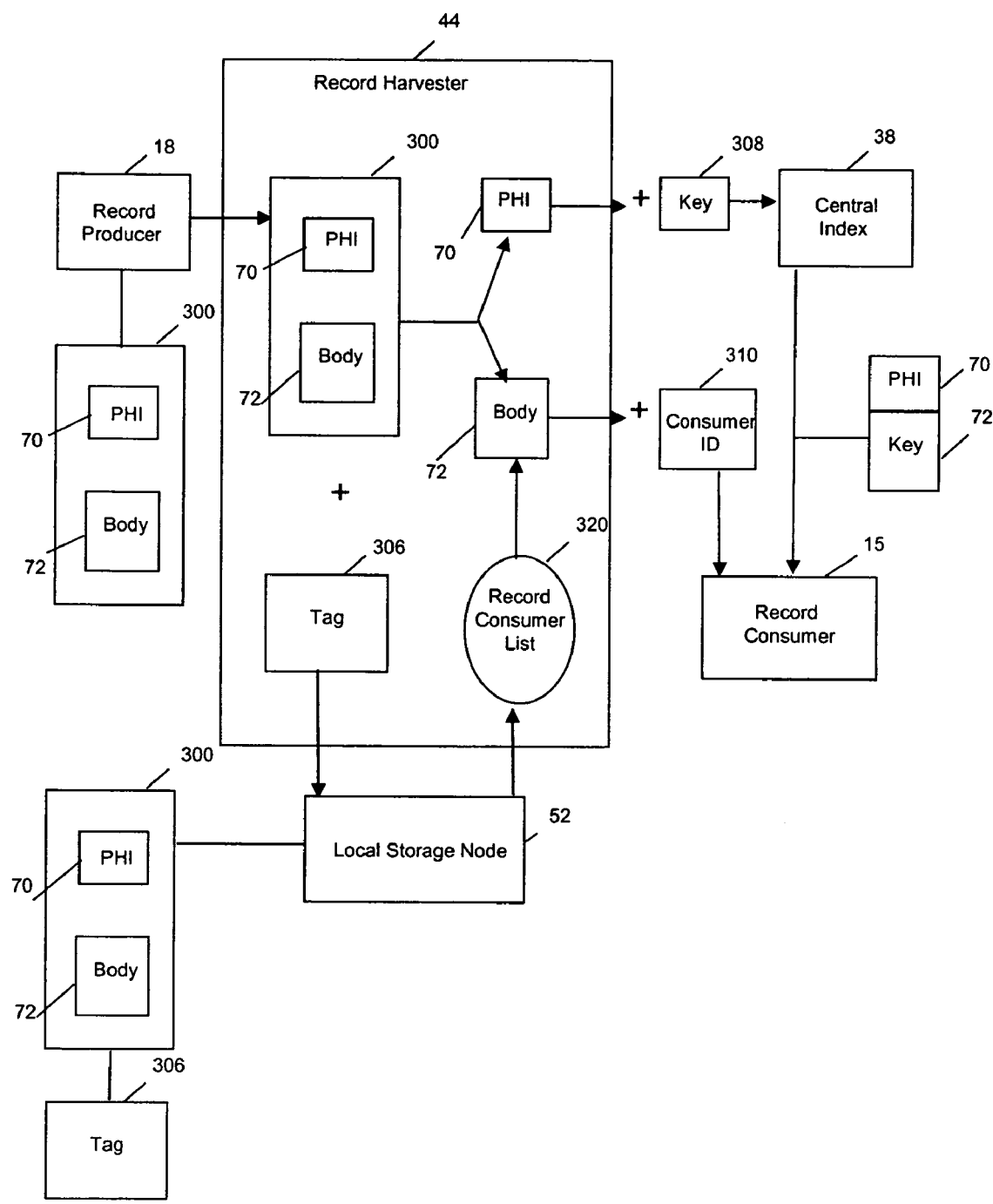
FIG. 18 is an alternate illustration of the digital couriering method of the present system, including the record producing, harvesting and uploading features of the disclosed system.

FIG. 18 is a more detailed illustration of the digital couriering method, including the harvesting process. The harvesting process is completed at the server level. During the harvesting process, new records are identified, an encryption key is associated with the study and the PHI 70 and the record are then copied to the local storage node 52. A copy of the PHI 70 is also sent to the Central Index 38. The PHI 70 and body 72 of the record are linked using a unique identifier, referred to herein as the Tag or Harvester Tag 306. This identifier or tag is not an encryption key, but only the link between the PHI 70 and the body 72 of the record. FIG. 18 illustrates the different components of a record 300 as it is harvested, including PHI 70, body 72, Harvester Tag 306, and Encryption Key 308.

As shown in FIG. 18, when the record is created at the record producer 18, the record 300 comprises PHI 70 and a body 72. The record 300 then enters the harvesting process. The record harvester 44 adds the Tag 306 to the record before sending the record to be stored on the local storage node 52 (FIG. 16B, step 236).

The loading of records from the system can occur in a few different ways. For examples, records can be pulled from record producer's computer or from PACS or other local storage systems. Loading of records can also occur when records are restored on the system, from direct loading from a file system, either single or multiple files, or CD import of records for directly uploading to the Central Server. When records are harvested, each record is verified on the system to ensure that duplicates are not created (FIG. 16B, step 234). Each file uses the Local System ID and Node ID to determine a match. Verification here occurs both when a record is uploaded and when a record is restored on the system.

In addition to being stored on the local storage node, the record is split by the record harvester into its two main parts: PHI 70 and body 72. The PHI 70 is then encrypted and a Key or Encryption Key 308 is added to the PHI 70. The PHI 70 plus Key 308 are then sent to the Central Index 38.

The Central Index 38 component is the central control point for the system. The Central Index keeps track of studies and the corresponding patient and referring record consumers for each. The Central Index keeps track of which nodes contain which records and when those records should move between the nodes. The Central Index may also comprise a set of services for different components of the system. Such services include, but are not limited to: upload PHI for a record; search for patient and associated records; search PHI for all records on a node; audit trail that shows each time PHI is touched by a user in the system; and billing information tracking.

Figure 19:
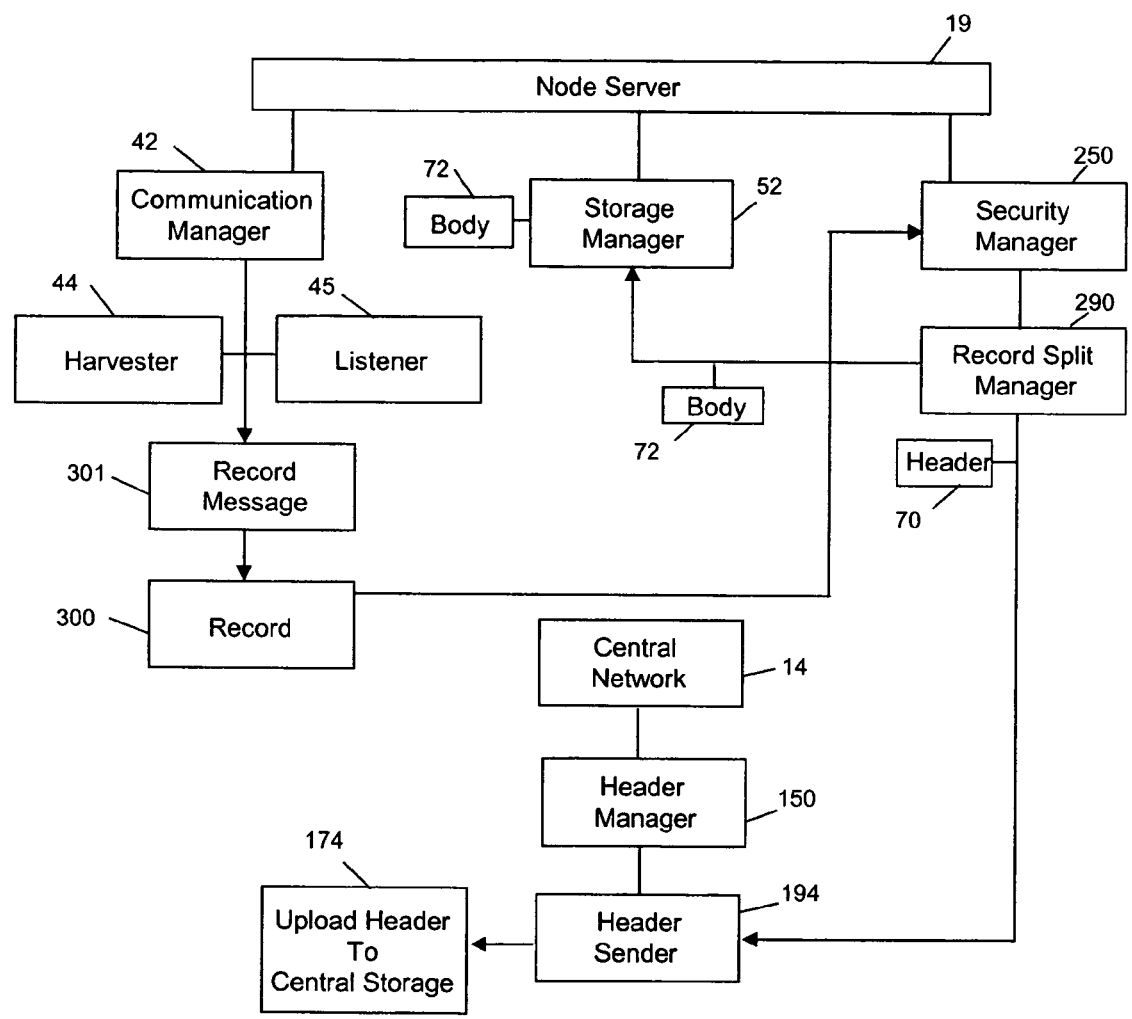
FIG. 19 illustrates the digital couriering mechanism of the disclosed system from the source node server to the central network, according to one embodiment.
Figure 20:
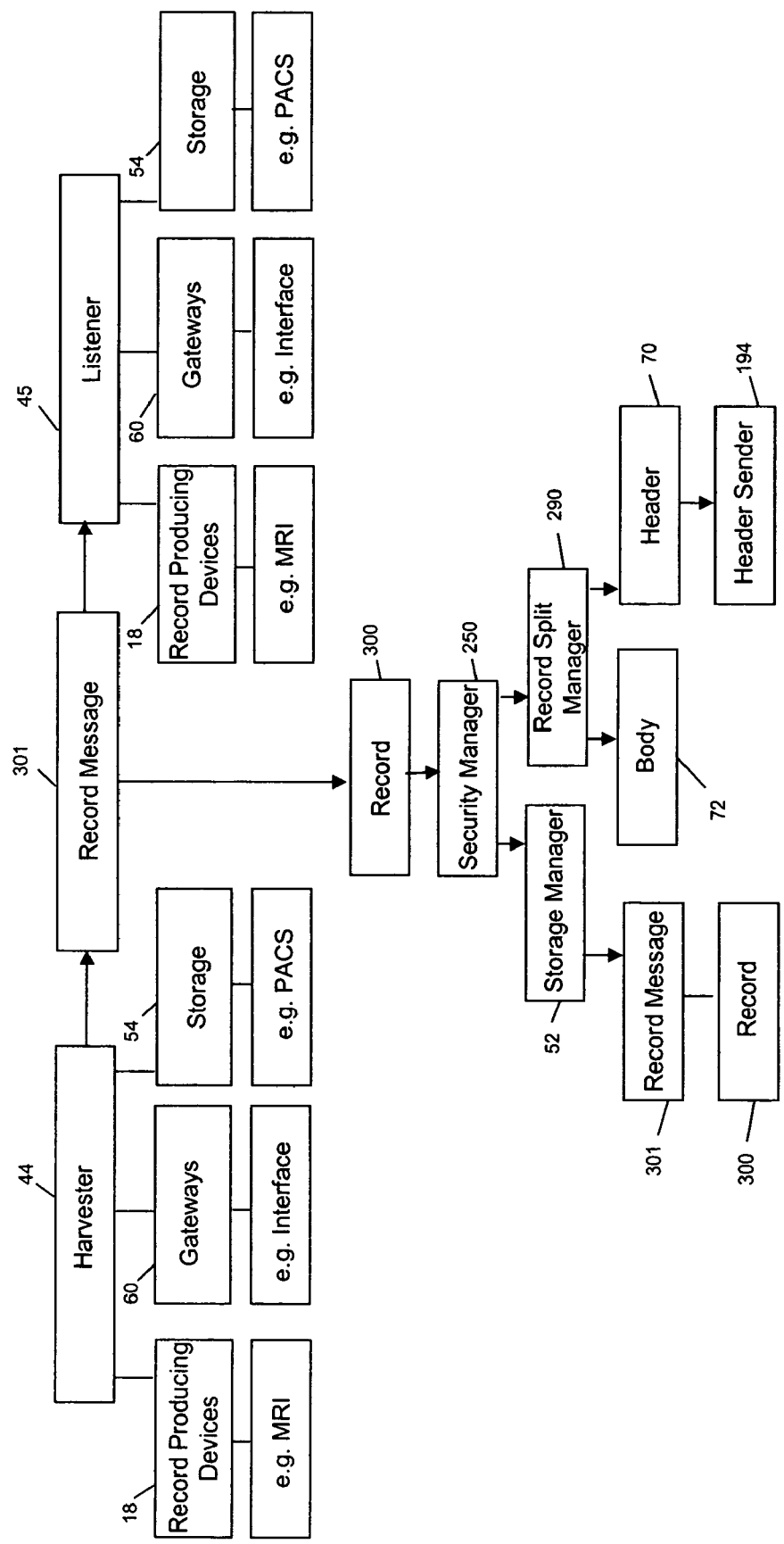
FIG. 20 illustrates one mechanism by which a source node of the present system manages records from a record producer prior to transmission.

FIGS. 19 and 20 further illustrate alternate embodiments of the record harvesting process. As shown in FIG. 19, communication manager 42 receives record message 301 and record 300 from the harvester or the listener. Communication manager 42 transmits record 300 with record 300 to security manager 250, and in particular record split manager 290. Record split manager 290 strips record 300 of its header 70 and send header 70 to header sender 194 in central network 14. Header sender 194 uploads header to central storage, namely header data 174 in database manager 36. Body 72, remaining after record split manager 290 removes header 70, send body 72 to storage manager 52 to store body 72.

As shown in FIG. 20, harvester 44 and listener 45 are both in communication with record producers 18, e.g. MRIs, gateways 60 (interfaces) and storage 54 (PACS). The configuration for harvester 44 maintains all the configuration values for the different record producing devices 18 located at the source node. These configuration values are stored permanently on the central network 14 and cached at the different nodes upon the registration of the node. Harvester 44 will still use the peer-to-peer network to pull down configuration values, but the values are not stored on the peer-to-peer network. Harvester 44 thus has the capability for an unlimited number of record producing devices to be configured and read by the harvester.

Harvester 44 further can take any file path or byte stream and send the file to storage manager 52 for processing. The primary use of this mechanism will be in loading files or records via a CD on-ramp or the reloading of records that had been previously removed from a source node.

As shown in FIG. 20, listener 45 listens for incoming transmission to the node and accepts data into the node for processing. As shown, the transmission consists of record message 301 and record 300. Also as shown in FIG. 20, listener 45 allows multiple record producing devices 18 to connect and push records to the harvester 44. Listener 45 accepts each record and deposits it to the storage manager 52.

In order to ensure HIPAA compliance with regard to protecting PHI, the audit trail of a record and the associated PHI are stored permanently by the system. In addition, certain rules exist about what information can and cannot be changed. For example, record consumer, record producer and patient data can be updated by the system upon appropriate authenticated request. Any change is this regard is captured in the audit trail and the full history of the change is saved in the system. However, the records and associated PHI are never modified by the system. The records are written to the system constitute the final version.

Within the central index, the PHI Manager is the central component that handles the collection and distribution of PHI associated with records that are on the system. The main input for the PHI Manager is the record harvester component. The main consumer of PHI is the viewing application at the remote storage nodes of the record consumer.

Also within the Central Server is the Network Node Manager. The network node manager is the central controlling point for the Peer-to-Peer Network. All nodes will authenticate or login to the system through this component. The management of record transfer, node status and node errors are handled here.

The node manager breaks down into two main sections, depending on the network transport used. Web services is used when information is being requested from the nodes and the manager needs to respond. Web services allows for easier transfers of dataset type information over a secure standard. Any communication when the manager is the initiator is done over the socket layer connection. This permits the local node to run with a thinner client and not have to host a web services and IIS to receive web service calls to it.

The record is then transferred to the record consumer. The transfer process is also referred to as Node-to-Node File Transfer as is illustrated in detail in FIG. 21. Further, FIG. 23B is a detailed data model of the components of the system according to one embodiment of the disclosed system.

Figure 21:
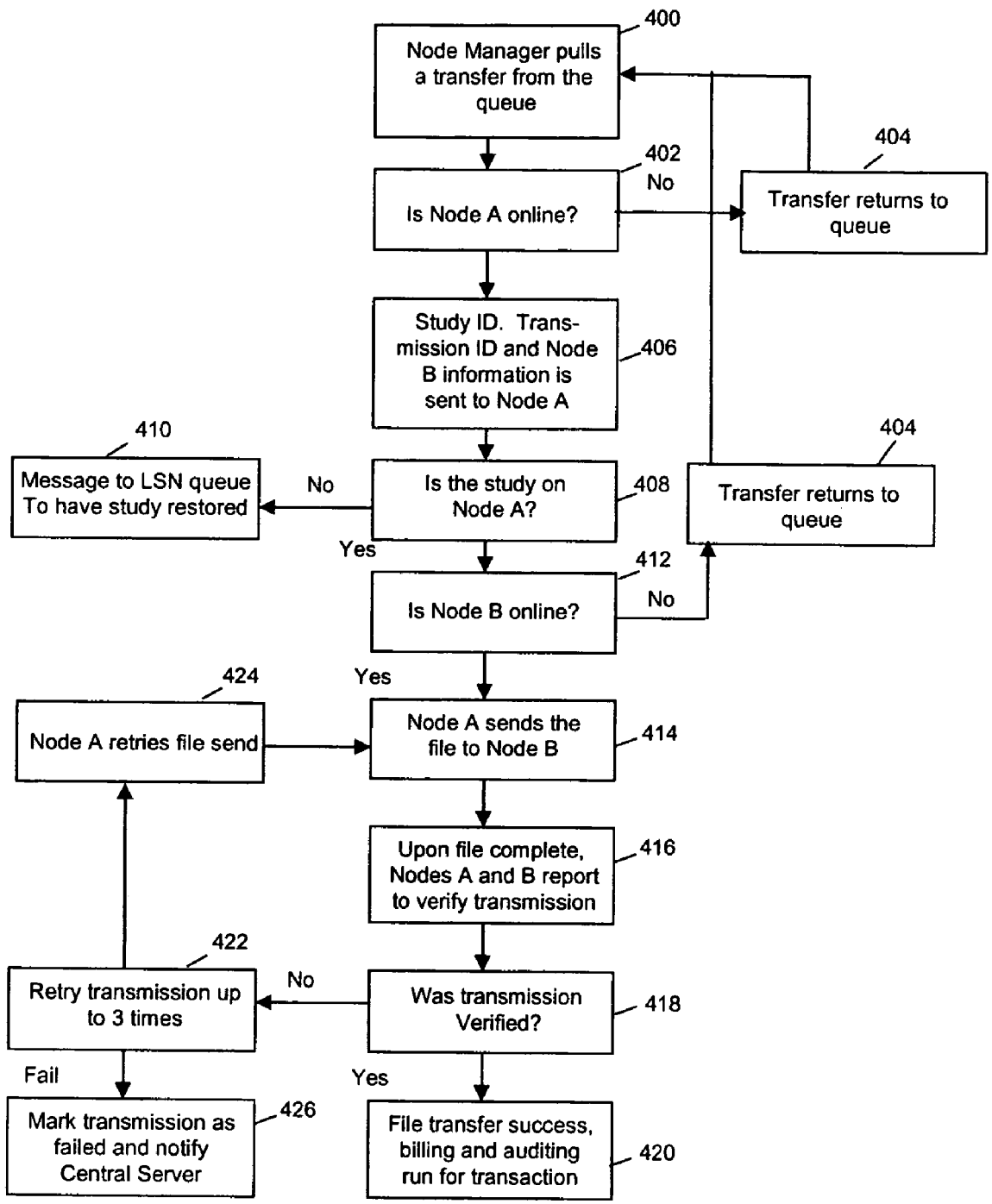
FIG. 21 illustrates one embodiment of nodal communication and verification of the disclosed system.

A transfer occurs when a record is either requested from a record consumer, or when a record has been added and all the information is available to preemptively push the record to the appropriate record consumer. The record transfer is logged into the transfer queue, with source and destination nodes given. In FIG. 21 the source node is referred to as Node A and the destination nodes as Node B.

When a record is set to be transferred from one node to another, the Node Manager is the controller of these studies' moving. In step 400, the node manager pulls a transfer from the queue and in step 402, checks to see if Node A is online. If not, in step 404, the system returns to the queue. In step 406, information regarding the transfer, including, but not limited to the Record ID, Transmission ID and Node B information, including the IP address, is sent to Node A. The system then checks, in step 408, whether the record is on Node A. If not, in step 410, a message is sent to the local storage node to have the record restored.

Once the system has verified that the record is on Node A, it is then locked so the cache will not remove it before transmission is complete. The system then checks, in step 412, to see if Node B is online. If not, the system returns to the queue in step 404. Node A sends the record to Node B in step 414. It is important to note that the record sent in step 414 is comprised of only the body of the record plus the Consumer ID directing it to Node B and to the particular record consumer for which it is destined. At the point where the transfer occurs, the PHI has already been separated from the body of the record through the record harvester described above.

Even though the traffic of the record will not travel through the node manager or central servers, all management and authorization to move records is controlled and logged at this level. Although security requirements do not call for encrypting information that transmits over the peer-to-peer network, due to the previous stripping of the PHI and because of the possible large file sizes, one embodiment envisions encrypting the initial data that transmits over the system as a safety measure to prevent hacking or DOS attacks.

In step 416, once the transfer is complete, both Nodes A and B report to verify transmission. The verification report consists of certain information, including, but not limited to, the Record ID, Transmission ID, date and time transmission was completed and checksum/hash on the nodes. Verification occurs when both nodes report success and the checksums match for the record transferred.

If it is verified in step 416, the record transfer was successful, in step 420 the billing and auditing are run for that transaction. If the transmission is not verified in step 416, in step 422, the transmission is retried multiple times, for example, three, and in step 424, Node A tries again to send the record. If transmission continues to fail, the transmission is marked as failed in step 426, and the Central Server is notified.

In at least one embodiment and based on the information connected with the record, the record consumer to whom the record needs to be transferred is selected from a record consumer list 320, and the ID of the record consumer, referred to as Consumer ID 310, is added to the body 72. The body 72 plus Consumer ID 310 is then pushed to the Record Consumer's P2P node, awaiting access by the Record Consumer (FIG. 16B, step 238). Once a record is pushed to the record consumer, a relationship, or "trust," is created between the patient and record consumer (FIG. 16B, step 239).

Thus, once the record has been created and harvested, as shown in FIGS. 18-20, the body of the record is preemptively sent from the record producer's Local Storage Node to the designated record consumer. The preemptive push constitutes a transmission for purposes of billing, described below. However, a search can also be conducted by the record consumer, record requested and the record then pulled to the record consumer depending on what records the record consumer has requested (FIG. 16C, step 240).

Figure 22:
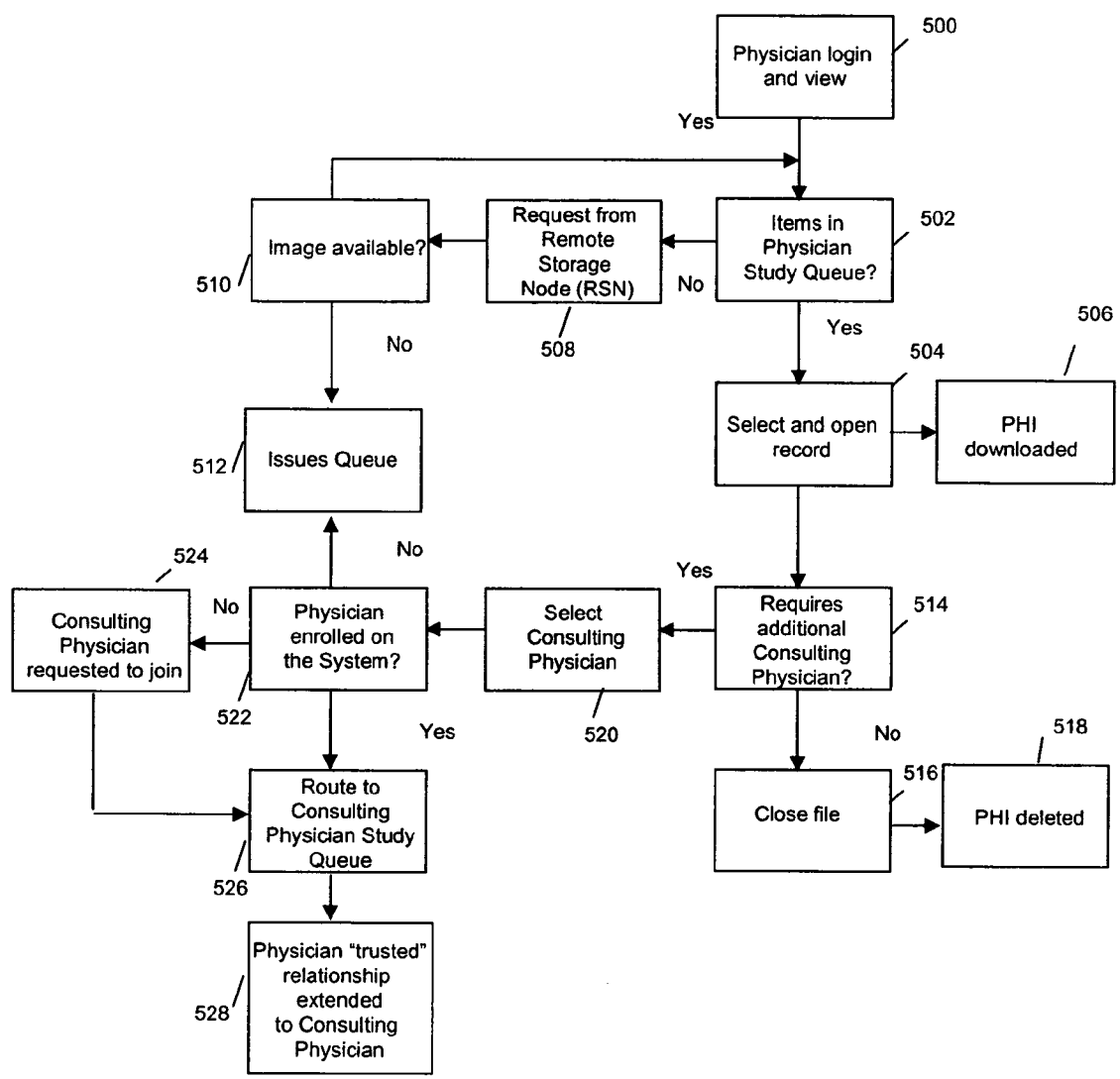
FIG. 22 illustrates one embodiment of record retrieval by record consumers.

As shown in FIG. 22, the record consumer logs in, in step 500, as shown in FIG. 15A. The record consumer is able to view any records in his queue that have been preemptively pushed to the queue. If there are records in the queue, in step 502, the record consumer selects and opens the record in step 504, comprised of the body only, and the PHI is downloaded from the Central Index in step 506.

The viewing application allows the record consumer to execute the steps in FIG. 22. Non-limiting examples of viewing applications are ones based on the .NET Smart Client. This allows for a simpler distributed install for end users as well as better updates of the software over time. The smart client architecture also allows for certain offline capabilities should internet connectivity be lost if the Central Server is offline.

This viewing application component allows the record consumer to rejoin the body of the record with the PHI onscreen. Inside the viewing application, the PHI is merged back with the body of the record to allow the record consumer to view the entire record. In order to ensure that PHI is never compromised, one embodiment envisions an overlay of the PHI on the body of the record. Such an overlay would permit simultaneous viewing of both parts without having to merge the PHI with the body of the record in the memory and then removing it again when the record is no longer being viewed.

If no records are in the queue, or if the particular records that the record consumer desires to view are not in the record consumer's queue, in step 502, then, in step 508, the record consumer can invoke his authorization and request records from one or more remote storage nodes (FIG. 16C, step 242). The system then determines if the record is available in step 510, and if it is, the record is sent to the record consumer's local storage node (FIG. 16C, step 244), and it is placed in the record consumer's queue and the record consumer can select and open the record in step 504.

In order for the image to be transferred, the record consumer must be enrolled in the system prior to the transfer, as described above in FIG. 14A. If the record consumer is not enrolled on the system, the record is routed to a queue for that record consumer. Once the record consumer joins the system, the record is waiting for viewing by the record consumer.

In one embodiment, the record producer notifies the record consumer that the record is on the system, and that the record consumer can join the system, in one embodiment, at no cost to the record consumer. If the record consumer does not want to join, the record is then manually couriered to the record consumer. In an alternate embodiment, the forward physician can add the physician from which a second opinion is sought or to which the physician is referring the patient. FIG. 15I illustrates an example of the screen for adding a physician. In this embodiment, if the physician does not enroll (FIG. 15J), the physician is likely granted only Tier 1 access.

Figure 15H:
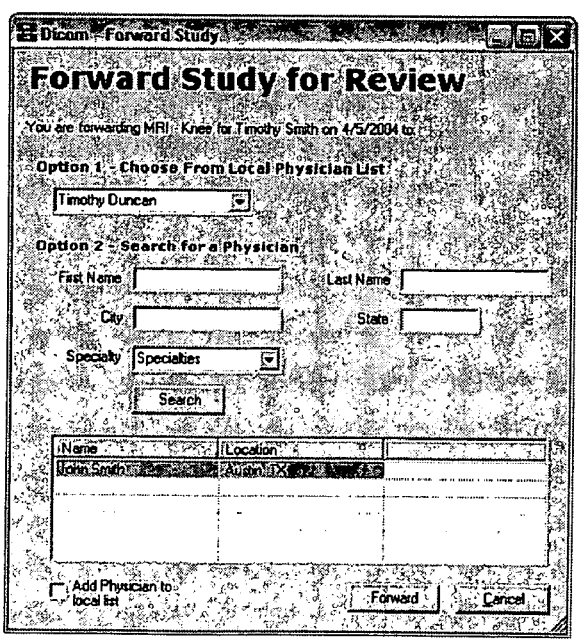
Figures 15I, 15J, 15K:
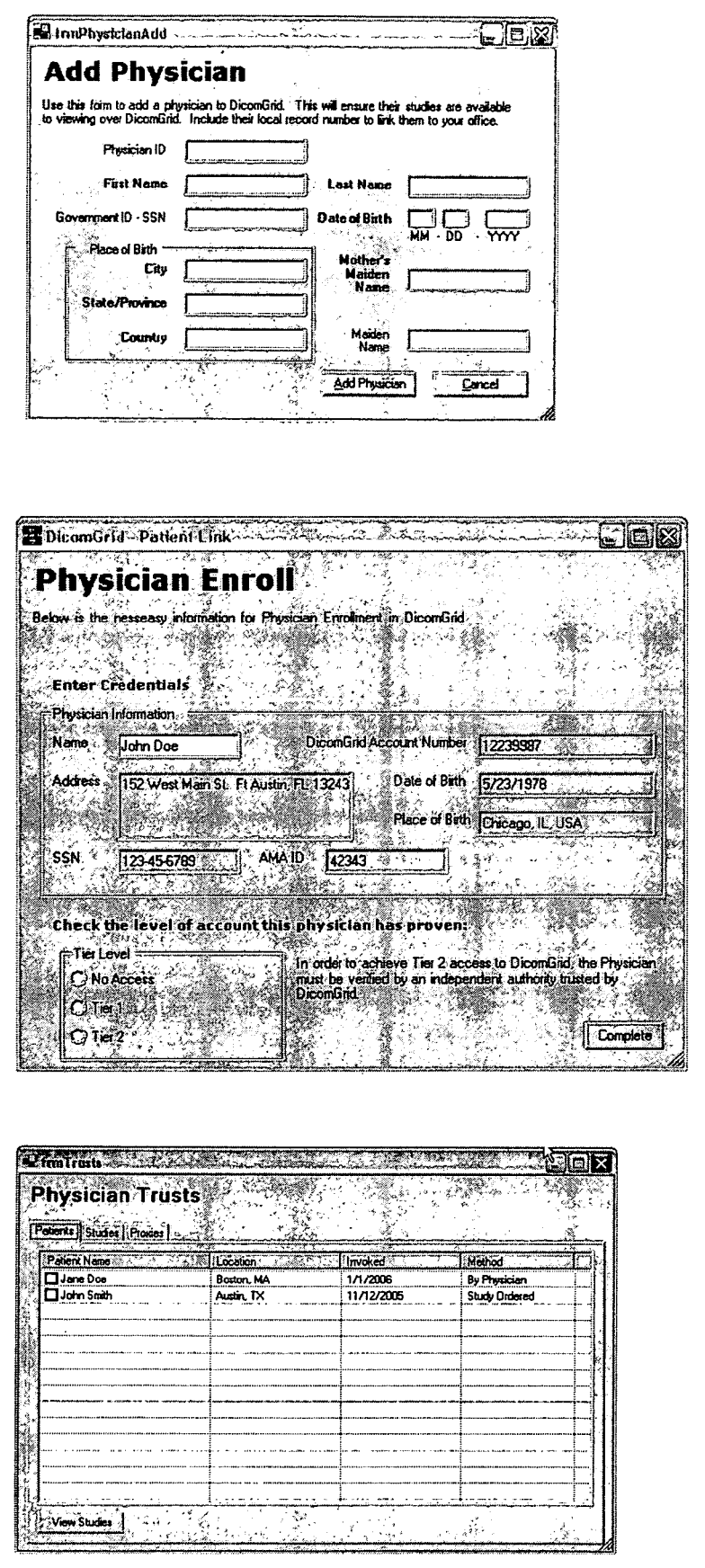

The same is applied to consulting record consumers in FIG. 22. If the record consumer requires a consult on the record in step 514, a consulting consumer is selected in step 516. FIG. 15H illustrates an example of the screen for forwarding a record to a consulting consumer or specialist.

If the consulting consumer is not enrolled in the system in step 522, the consulting consumer is requested to join in step 524. FIG. 15J illustrates an example of the screen for enrolling in the system. If the consulting consumer is already enrolled in step 522, or joins in step 524, the record is routed to the consulting consumer's queue in step 526. Then, in step 528 the record consumer's chain of trust is extended to that authorized consulting consumer. Once the record is viewed by the record consumer and/or consulting consumer, the record consumer can then visit with the patient regarding the contents of the record (FIG. 16C, step 246).

Figure 23A:
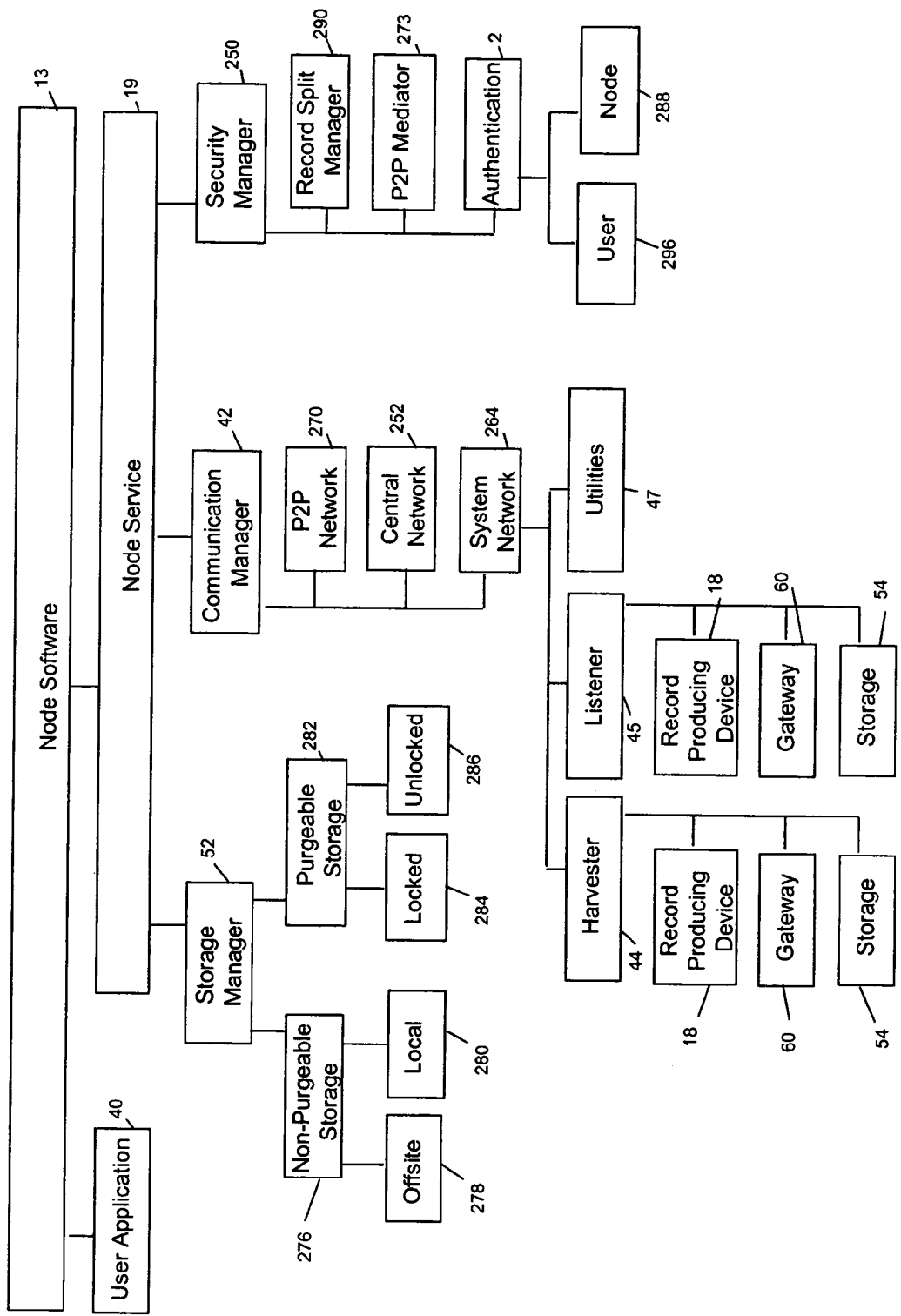
FIGS. 23A and 23B illustrate one embodiment of the node software and a detailed data model of the components of the disclosed system.
Figure 23B:
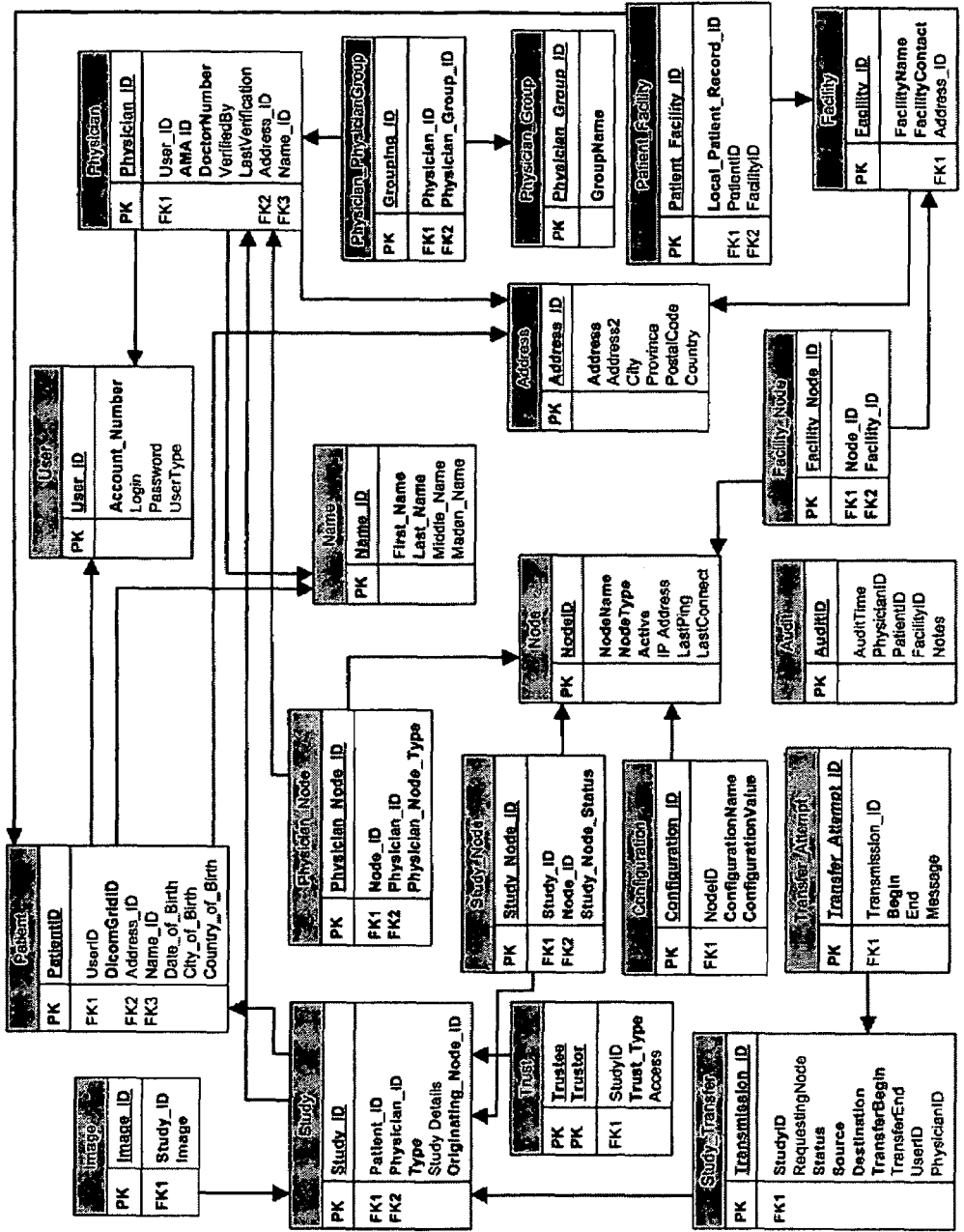

FIG. 23A particularly illustrates the elements of node software 13. As shown, the node software includes client application 40, described above, as well as source code to execute the functionality of node server or node services 19, also described above. At a higher level, and in communication with the central network, node software 13 also controls and regulates versions of the application that can be downloaded to new and existing nodes. The component alerts when new software is available to be downloaded and installed.

Node software 13 is only downloaded to authorized nodes and people. Node software 13 is only downloaded if all requirements and dependencies are met. Node software 13 generates a machine key for each computer downloading the software. As noted above, FIG. 23B is a detailed data model of the software components of the system according to one embodiment of the disclosed system.

FIG. 24 illustrates the central network 14 administrative or ID Hub 600 functions of the present disclosure. The administration component maintains the accounts, persons, facilities and the configurations of the local node. As shown in FIG. 24A, administrative ID Hub 600 can add new 601 patients, physicians and facilities (record producers and record consumers) to the database. FIG. 24B illustrates the addition of a new 601 Individual X to the system.

Figure 24A:
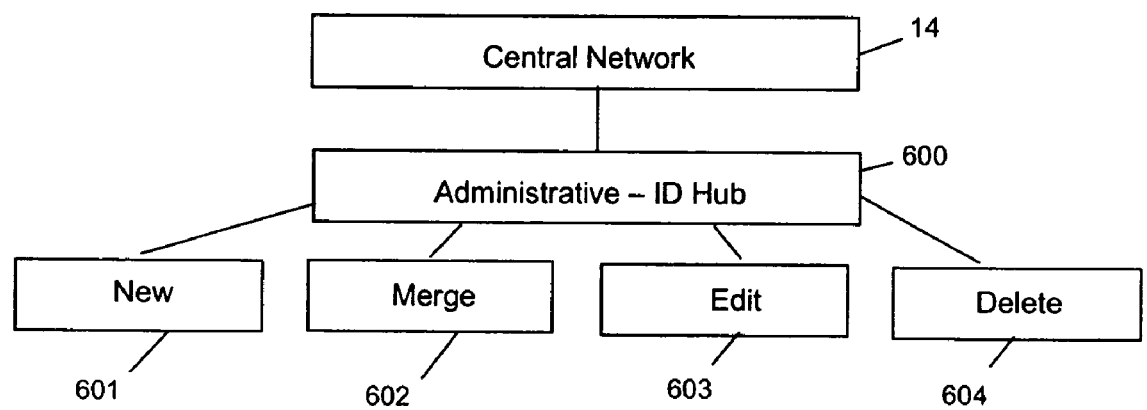
FIGS. 24A through 24G illustrate the administrative components or ID Hub features of the present system.
Figure 24B:
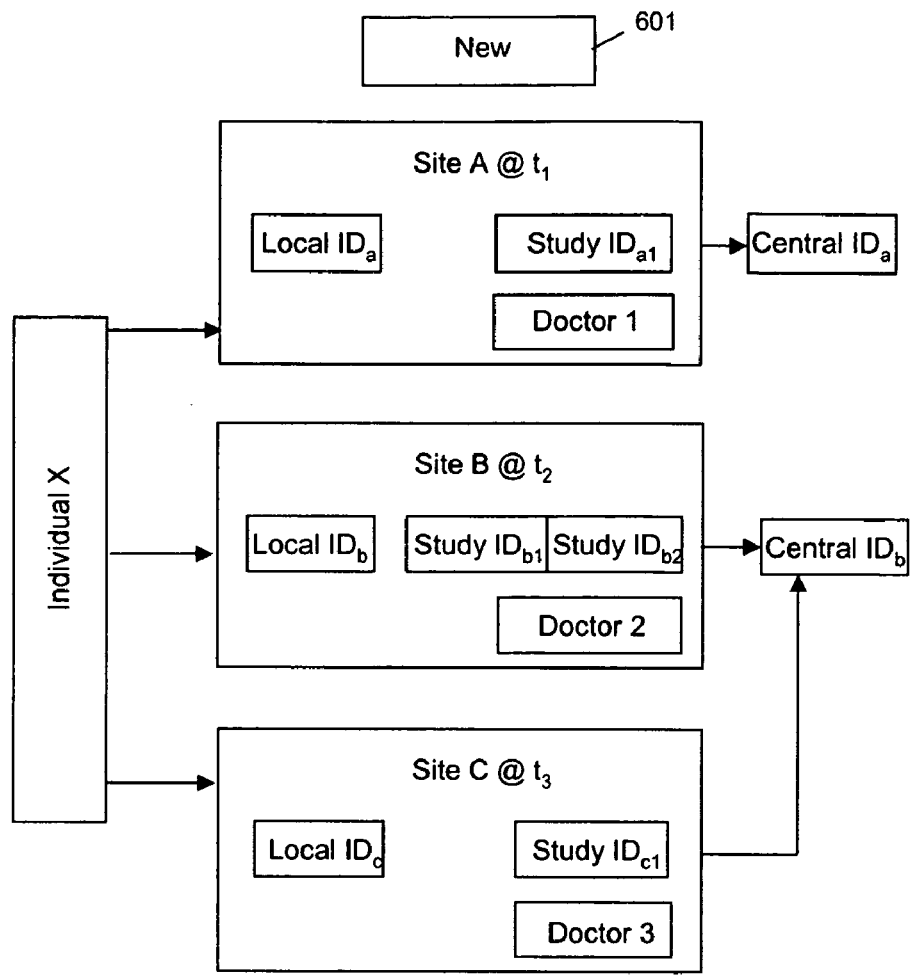

As illustrated, Individual X has four records (referred to here as Studies) at three different sites (A, B and C) that were produced at three different times (here, t3>t2>t1). FIG. 24B illustrates how each record has a site identification (Local ID), a record identification (Study ID) and a doctor identification (Doctor ID). The record at site A was provided to the system as a new patient and given Central IDa. The records at Site B were provided to the system as a new patient and given Central IDb. However, the record at Site C was added to the system after a search successfully determined Individual X existed on the system as Central IDb, and thus was added to the system for Central IDb.

Figure 24C:
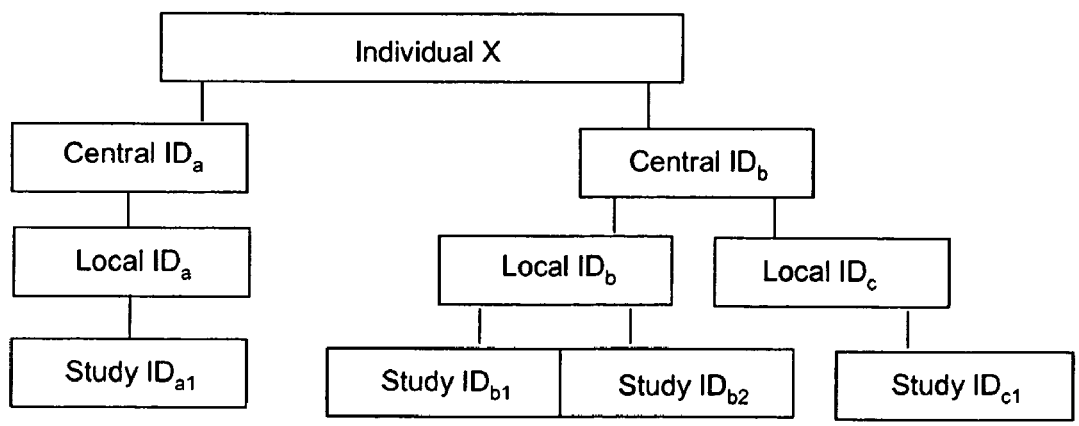
Figure 24D:
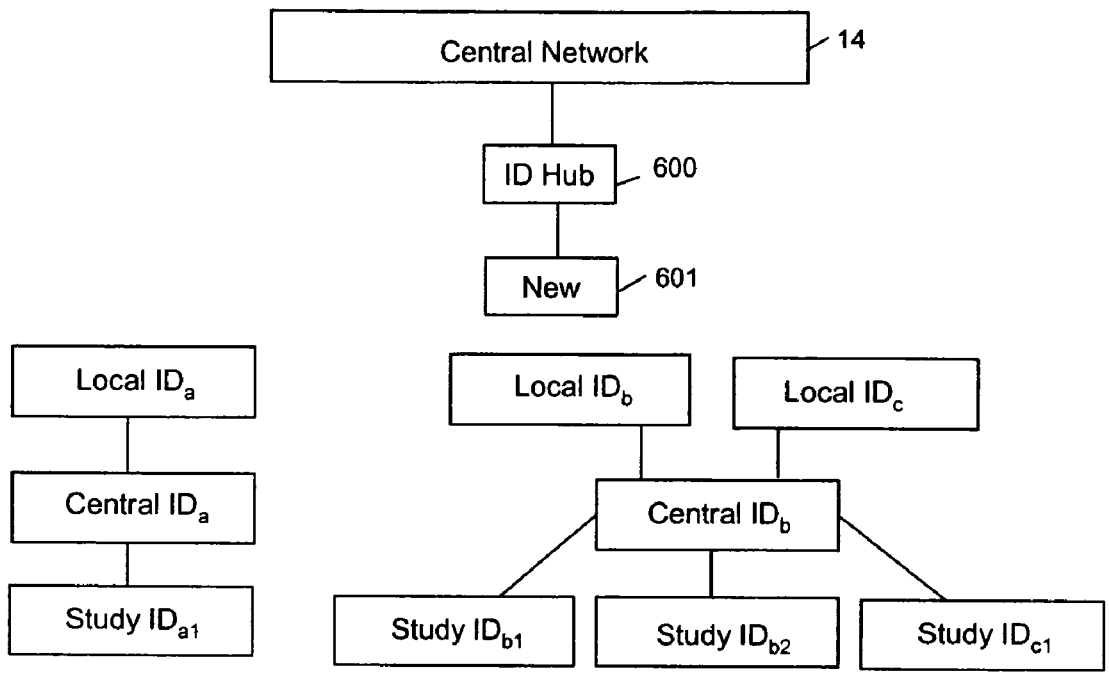

FIG. 24C shows a simplified diagram of all the information existing for Individual X that has been sent to the system. FIG. 24D illustrates how the disclosed system initially organizes the information provided on Individual X before any subsequent processing of the information occurs. As shown, Central IDa and Central IDb are not yet connected.

Figure 24E:
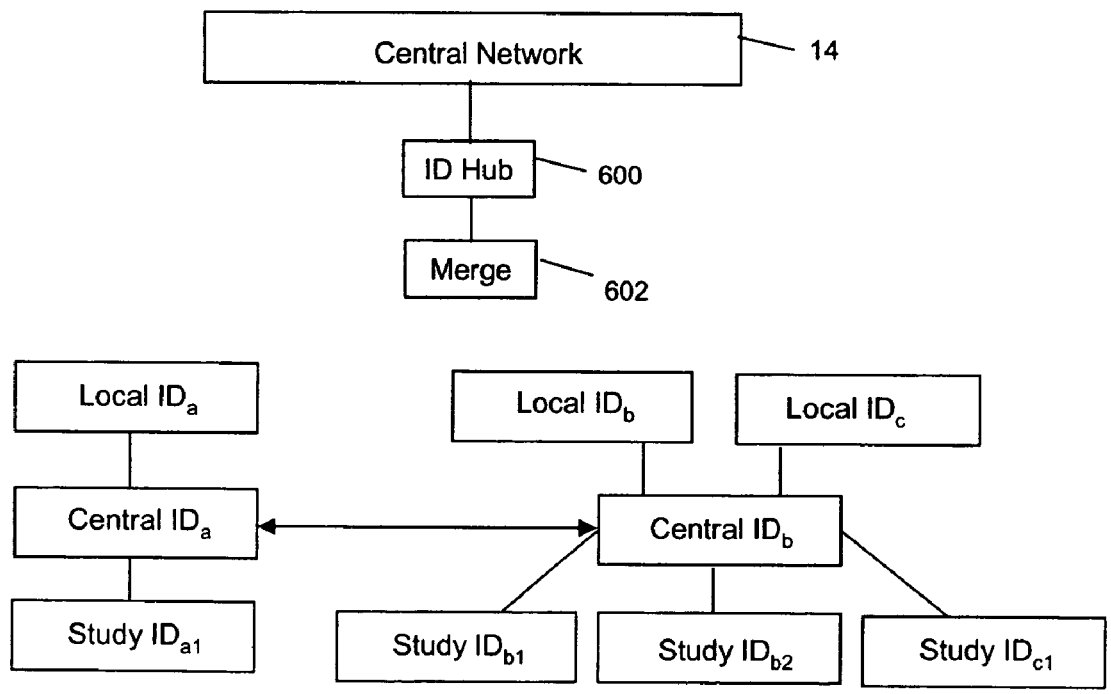
Figure 24F:
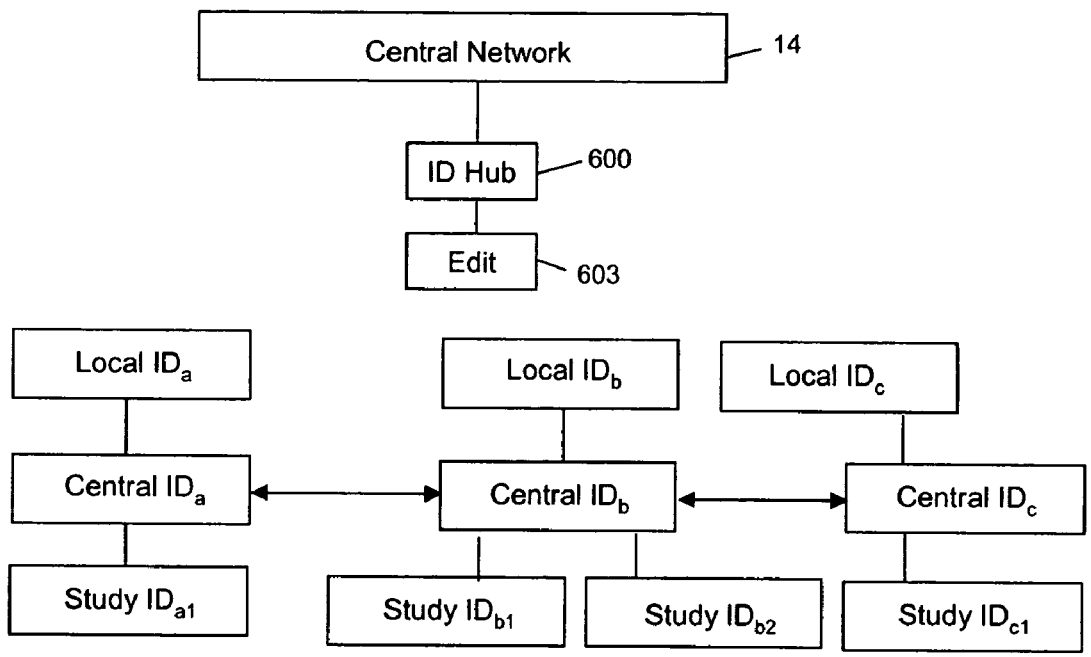
Figure 24G:
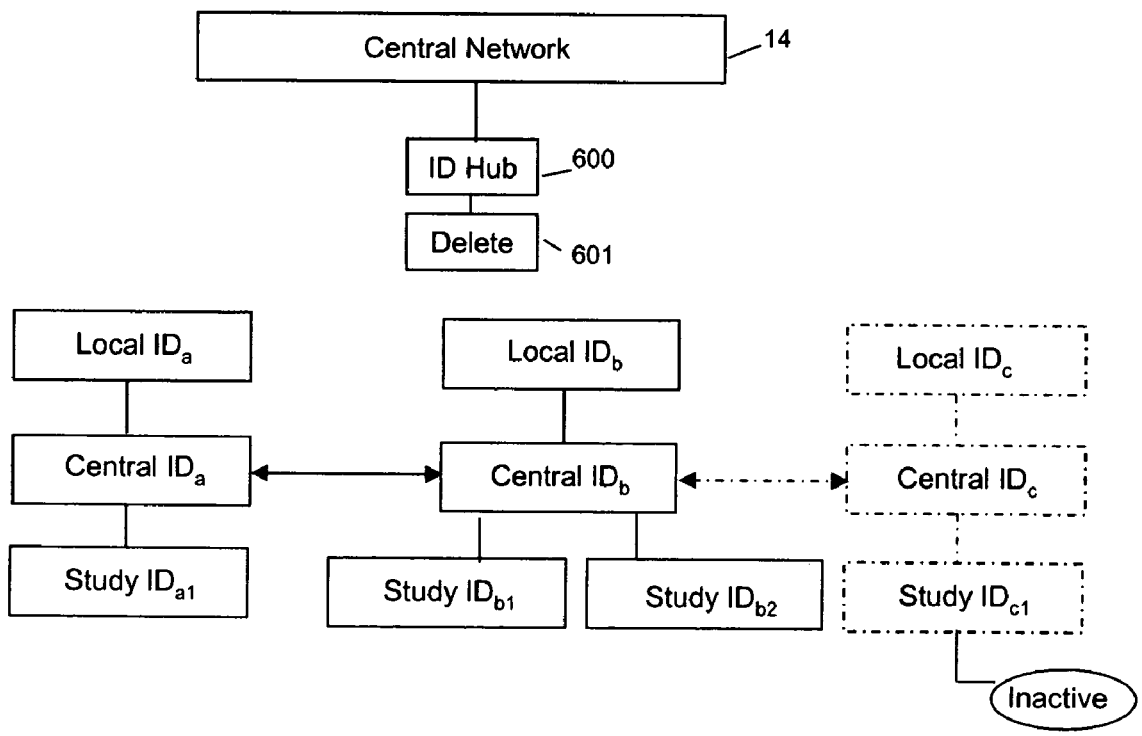

As shown in FIG. 24E, the system then uses its merge 603 function to link Individual X's Central or System IDs, and connects Central IDa and Central IDb so the system knows that both identifications reference the same Individual X. This also allows all other associated data to be connected. As shown in FIG. 24A, administrative ID Hub 600 can also edit 602 patient, physicians and facilities on the database. The particular edit 602 function shown in FIG. 24F, illustrates how the system can create a third system identification (Central IDc) in order to manage the information from Site C separately. This would be necessary if, as shown in FIG. 24G, the information from Site C was to be removed or deleted from the system using delete function 604. Once Central IDc is deleted from the system, all related information is inactive and cannot be accessed.

Figure 25:
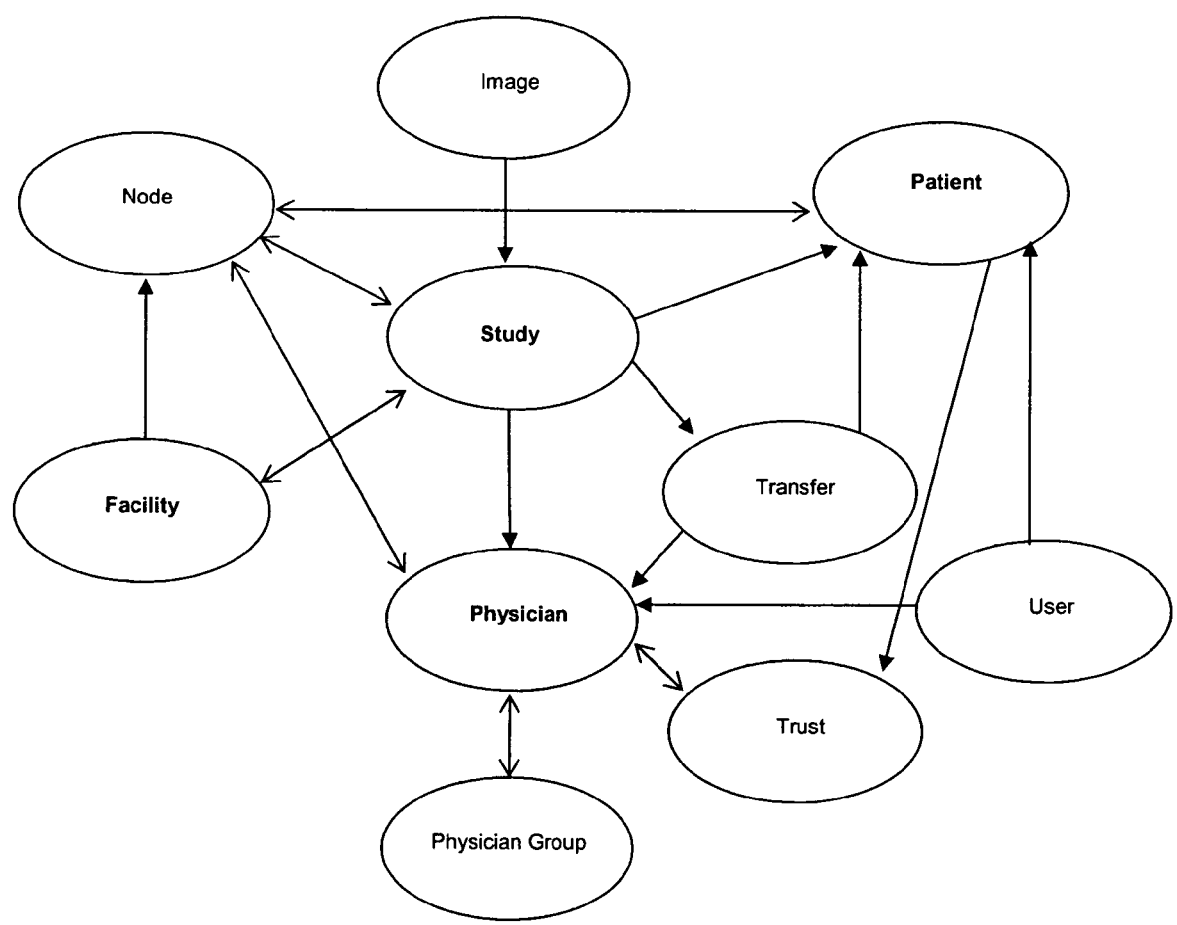
FIG. 25 is a high level diagram illustrating the transfer of information across the disclosed system in conjunction with the chain of trust relationships in the system.
Figure 26A:
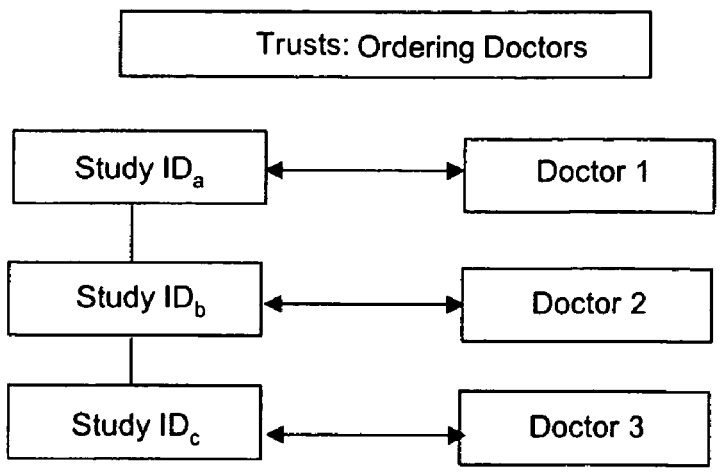
FIGS. 26A though 26D illustrate the chain of trust features of the disclosed digital couriering system.
Figure 26B:
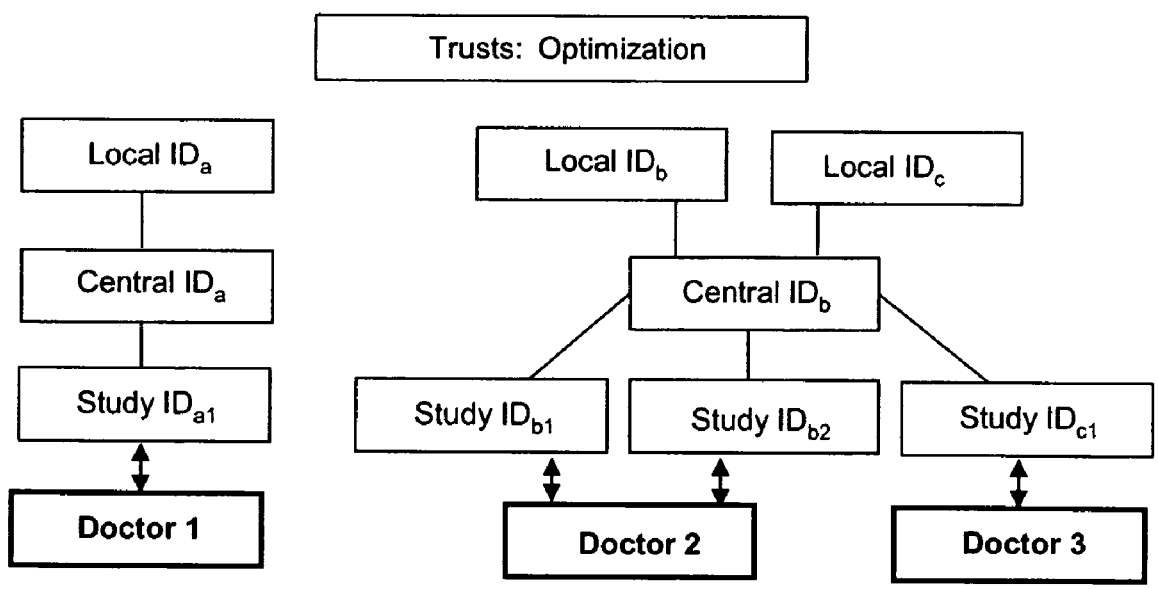
Figure 26C:
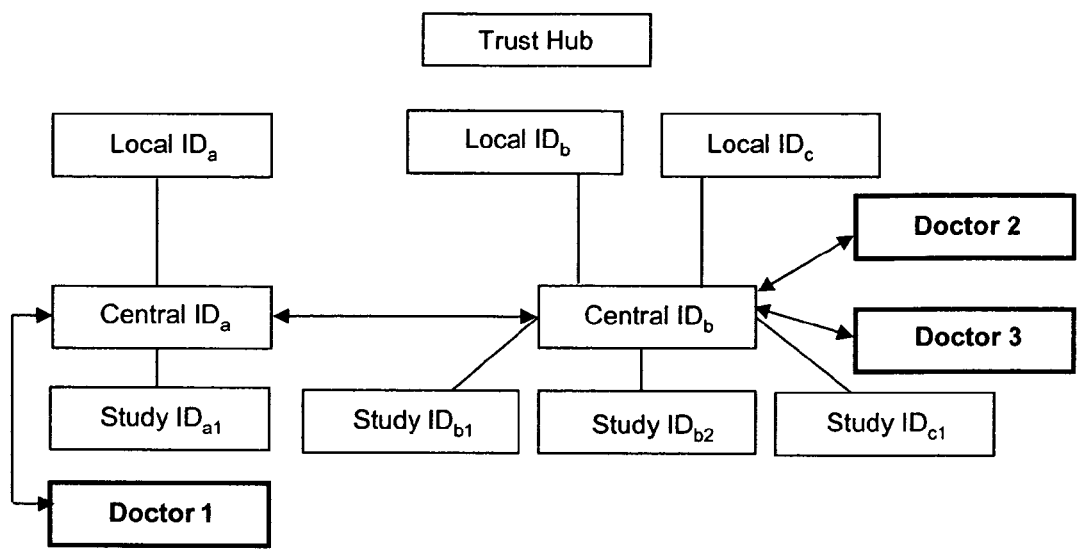
Figure 26D:
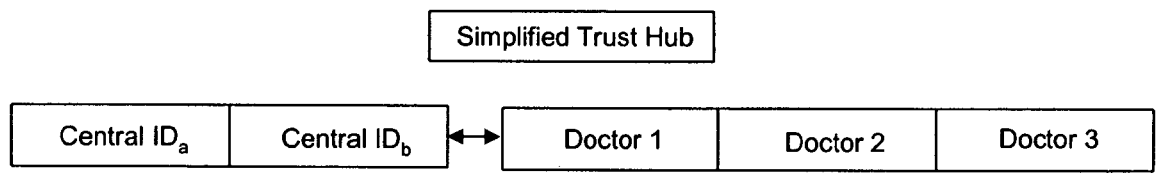

FIG. 25 gives an overview of the "chain of trust" relationships with the different entities of the system described above. FIGS. 26-29 depict how trusts are transferred across the system from patients to record consumers (physicians), first or primarily from patient to doctoring order the study as shown in FIG. 26A, and second to record producers (facilities) with associated Local IDs, as shown in FIG. 26B. Once these trusts are established, the system can optimize the chain of trust as shown in FIG. 26B and create a "trust hub" as illustrated in FIG. 26C that shows the complete chain of trust for Individual X on the disclosed system. FIG. 26D illustrates a simplified trust hub, as would be established by the system, to determine which record consumers (doctors, and here Doctors 1, 2 and 3) would be allowed to access the record.

Figure 27A:
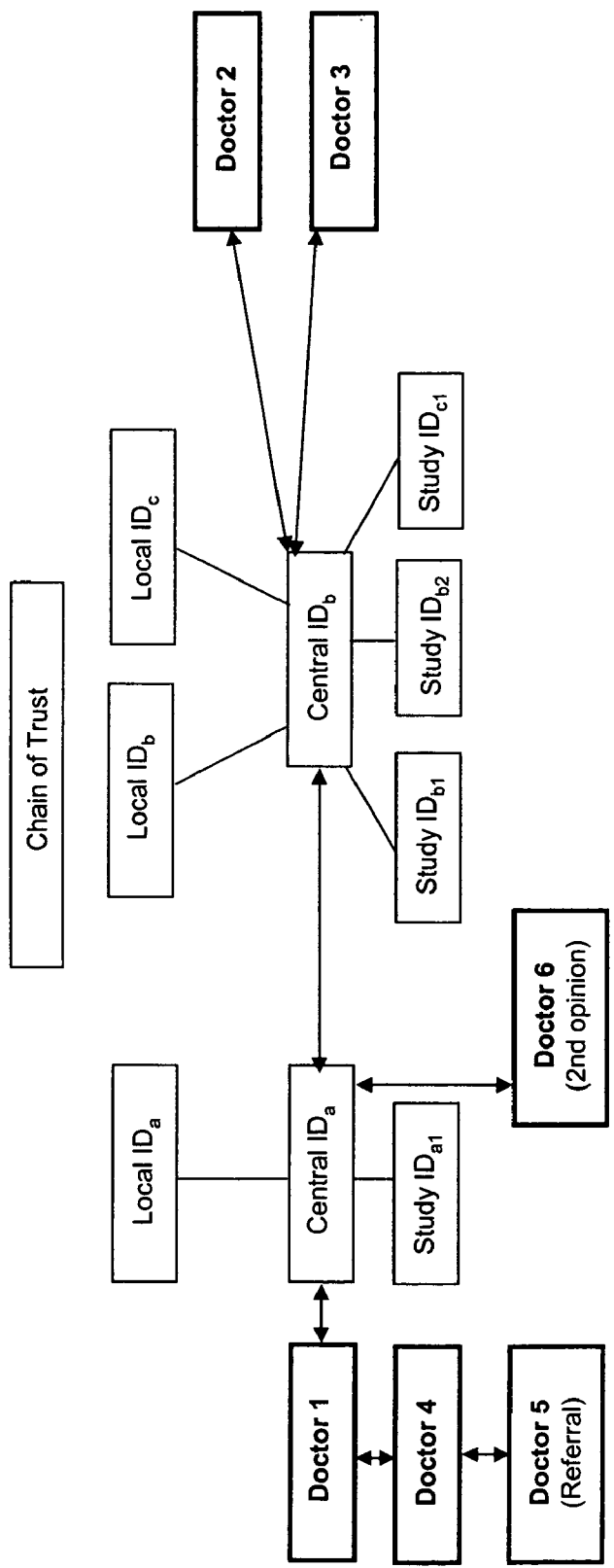
FIGS. 27A and 27B illustrate forwarding and referral chain of trust features of the disclosed system.
Figure 27B:
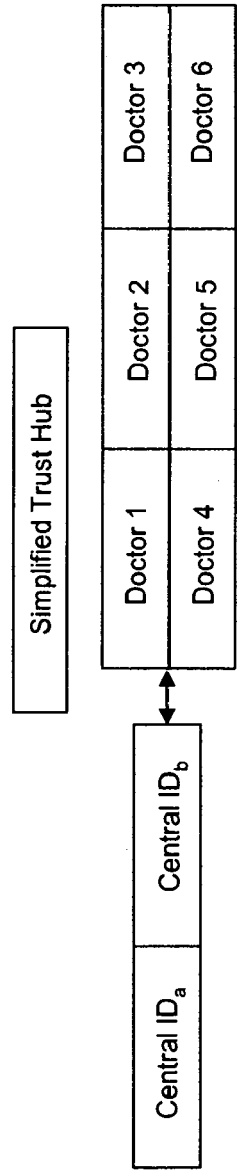

FIGS. 27A and 27B further illustrate how the chain of trust is passed to authorized record producers (facilities) or to record consumers (physicians), as the case may be. As shown in FIG. 27A, trusts can be added across the system. FIG. 27A illustrates how trusts are added by referral (to Doctor 5) or second opinion (to Doctor 6). The control of trusts can reside with the patient or patient's designee, such as one or more record consumers (doctor, hospital, etc.).

Figure 28A:
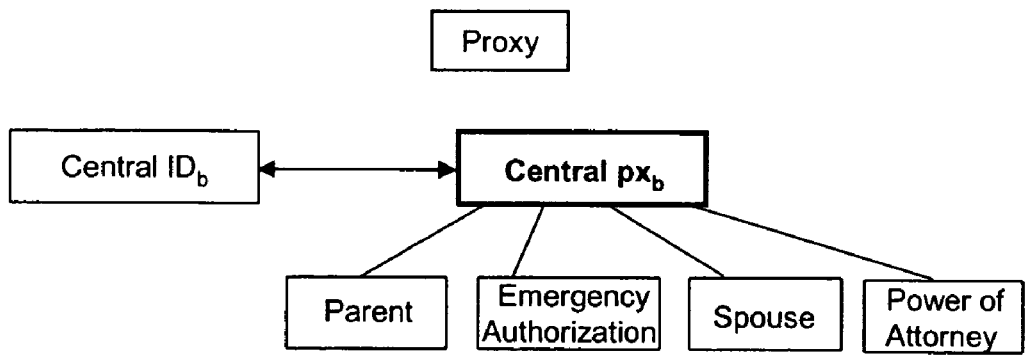
Figure 28B:
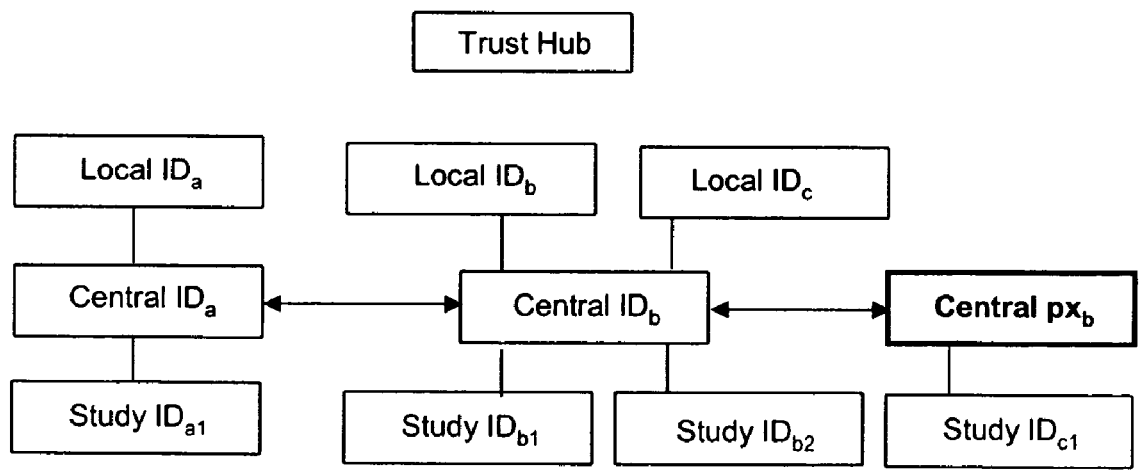

FIGS. 28A and 28B illustrate the proxy aspect of the chain of trusts feature of the disclosed system. Here, in FIG. 28A, a proxy, for example, a parent of a minor, a spouse, someone who has power of attorney, or another emergency authorization provides for a proxy, which, for example, has been designated by Individual X or provided for by law (in the case of a minor or emergency). FIGS. 28A and 28B illustrate how the proxy is given his own Central ID and how that ID is then connected with the existing Central IDs for Individual X, creating the modified trust hub shown in FIG. 28B. FIGS. 28C and 28D then illustrate how the chain of trust would appear if or when the proxy authorized another doctor (Doctor 7) to have access to the records on the system.

Figure 29A:
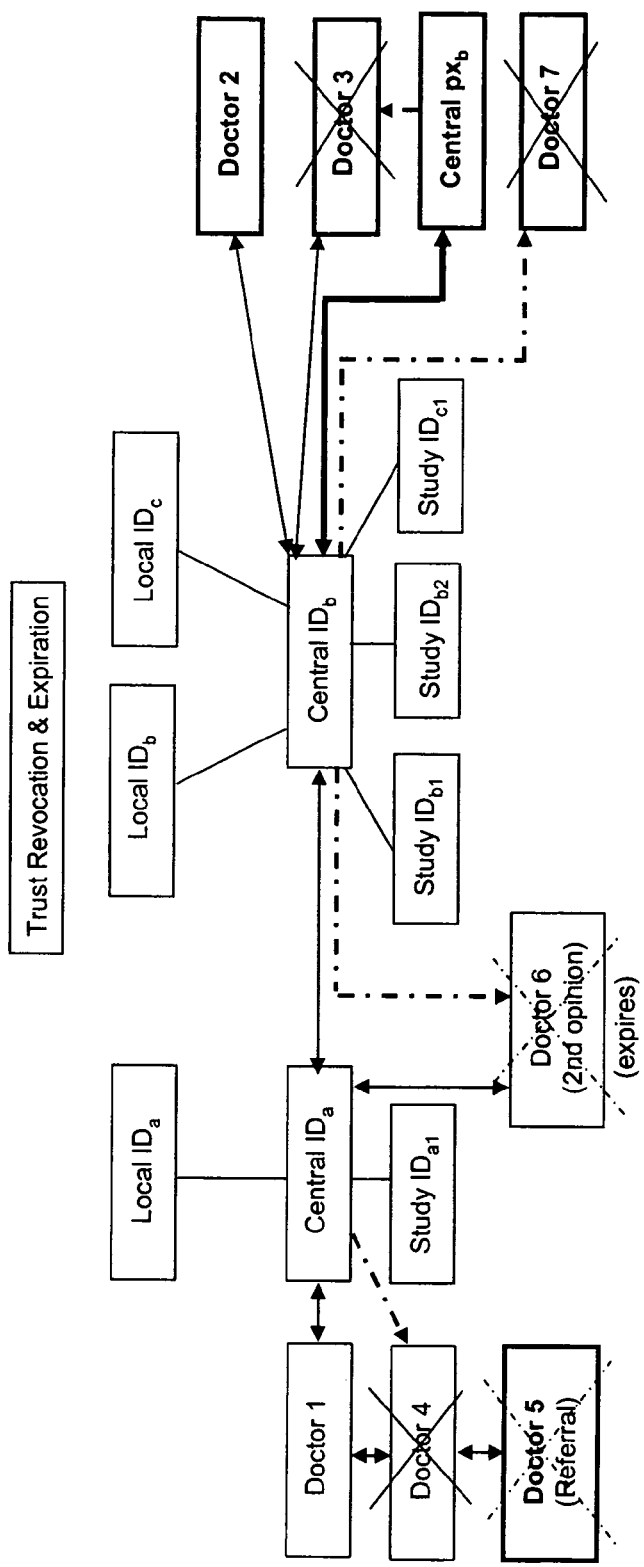
FIGS. 29A and 29B illustrate trust revocation and expiration features of the disclosed digital couriering system.
Figure 29B:
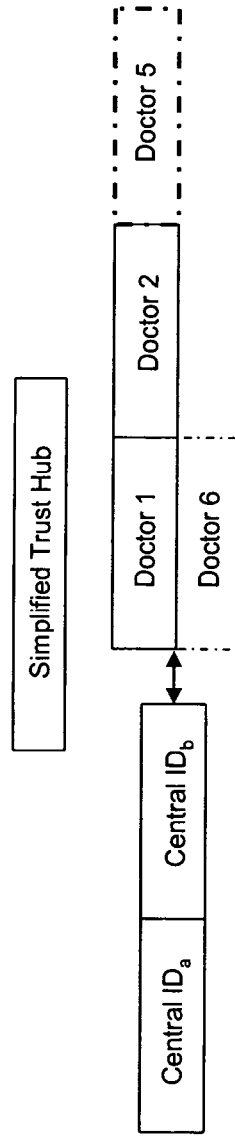

Finally, FIG. 29 illustrates the trust revocation and expiration features of the chain of trust. As illustrated in FIGS. 29A and 29B, certain trusted relationships not established by a direct doctor patient relationship (as shown in FIG. 26A), for example, doctors that have given second opinions, can expire. Also trust can be expressly revoked, either by Individual X (Doctor 3 and Doctor 4) or by the proxy (Doctor 7). Finally, when certain trusts are expressly revoked, as is the case with Doctor 3 here, certain other trusted relationship that may be dependent upon Doctor 3 (for example, possibly the referral to Doctor 5) could also be subsequently revoked, unless directed otherwise.

The Central Server has several other administrative interfaces and online reports to manage key tasks. First, the Central Server has the ability to view record consumers with records in queue but who are not enrolled in the system. This allows the system to follow up with the record consumer and enroll him. The Central Server has the ability to view a list of record consumers and record producers awaiting approval. The Central Server has the ability to assign and review credit status. The Central Server also has the ability to view node and session status and control node status. Finally, the Central Server has the ability to view issues that cannot be resolved at the record producer or record consumer level.

The client application provides basic administration and reports tools to manage the costs, resolve issues and invoice. The client application also provides an interface to administer some key information and view online reports for the record consumer.

In one embodiment, the system charges all record producers a subscription fee as well as a fee each time the record is transferred. The subscription fee is an annual or other periodic fee. The transmission or transfer fee is charged for the movement or transmission of a study from the record producer to the record consumer. The fee replaces the current courier fee paid to physically move studies. Although, the disclosure also envisions no fee, or alternate fees, for example a subscription fee, but not a transaction fee, and vice versa.

Storage fees may also be charged for storage of the records on the system. These fees will be charged for records that are stored on the system in a permanent form and become the document of legal record for the record producer. The storage fee may be a per document fee or flat fee.

In order to facilitate billing, each time a record is authorized to move across the network, it is logged as a transaction. The transmission is logged after the file has been confirmed on the destination (network) node. A report is available to view this information as well as the ability to export the information to the invoicing or billing system at the central server.

The billing system also allows support billing based on both origin and destination nodes (storage and network nodes) and takes into account any discounts or other features that have been set up for those facilities. In an alternate embodiment, patients are responsible for fees.

Security is very important to the disclosed system. Securing access to the data in the database is performed using multiple techniques to protect against unauthorized access. The techniques that are applied incorporate the functions of Resource Description Messages (RDMs) that are implemented as well as custom security developed using tables for administrative purposes and security logic on the application servers.

Direct access to the tables in the database that contain sensitive and private information is not permitted. Access to these tables is done using views and stored procedures. Using views and procedures permits data to be secured at the record level. Record level security is achieved by creating an additional column in the table to indicate the sensitivity of the date in the record. The security level column contains a numeric value to indicate the data's importance. The higher the value, the more important the data is. System users are organized into security level groups. Only users with a security level or higher of the value in the record can access the record. This is particularly useful when certain patient records are blacked out. When a user queries the table's view, the user credentials are determined and automatic filters are applied to the query to prevent any records from returning with higher security levels than the current user.

Users are also classified into groups based on their responsibilities and requirements. When a new user is created, he is assigned to a user group with a predetermined security level. As noted above, the security level determines the level of access of the data the user has. The user group will also determine the functional modules the user is allowed to perform in the system. A system administrator can override the default settings for a user group to increase or decrease the level for a specific user.

As indicated above, each area of the system is categorized into modules. The modules group organizes the functional requirements of the system into common objectives. Some of the modules in the system are administrative, reporting, record consumer, record producer and record owner (e.g., patient). User groups are assigned to the modules to which they require access.

Component level security is defined based on the functionality of a component that defines a system application. Each component has a separate database login assigned to it. The login ID is used to track the activity of the component and the permissions it has with the objects in the database.

Login access to the database is provided by login IDs. Each login ID consists of a username and a password. The password is an alphanumeric value with a minimum of eight characters. The login IDs have different object permissions and credentials. The login given to the application and component depend on its purpose and requirements. Logins only contain the necessary permissions a component or application needs. The system also supports custom user logins to identify individuals logging into the system. The user logins also consist of a username and password. The username is the email address of the user and the password is a minimum of eight characters. The username and password are stored in a table in the database. The password is encrypted by the application prior to being saved in the database to prevent database logins from viewing the passwords.

The tracking of changes of data in the database is also key to the security of the disclosed system. The auditing capabilities of the system database provides the requirements for each component and module to track data through the system. All tables will have four standard columns to track when records are created and updated. The tables will have two columns to denote the user and the time the record was created and two columns to denote the user and the time the record was last updated. Tables that track changes of its records that occur incorporate triggers to retain a copy of the record before the update occurs. The update trigger for the table inserts before a record in an audit table associated with the designated table.

All actions and events that occur between the main entities in the database are logged, as described above. An event record will contain the time the event occurred, the IDs of the entities involved in the event, the type of event and the elapsed time of the event. An example of an event is when a physician requests to view a record. The event records the physician's ID, the record ID, the time it was reviewed and the reason it was reviewed, e.g., a second opinion. User and node access to the system is logged to track overall activity of they system and to keep track of usage and growth. When a user or node is authorized on the system, a record is created containing the user ID or node ID, the IP address and the time access occurred. A second record is created when the user or node disconnects from the system.

Thus, the disclosed system and method maintain the security of private health information (PHI) in accordance with HIPAA standards while maximizing the efficiency of transmission of medical records over the Internet. As noted above, this is primarily accomplished by separating all PHI from the body of the record as they are transmitted. The PHI is only combined with the body when it is viewed by an authenticated record consumer.

Thus, the disclosed system and method provides numerous advantages over the prior art. First, the disclosed system is compliant with HIPAA privacy and security requirement, including, but not limited to, compliance requirements with downstream vendors. Second, the disclosed system and method removes the risks of human error associated with physically handling and transporting records. Third, the present system includes electronic measures to minimize the risk of lost or stolen records. Fourth, medical services providers can rely on the chain of trust that is required under HIPAA. Finally, the system and method is substantially more efficient and cost effective than any current alternatives.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventor that the words and phrases in the specification and claims be given the ordinary and accustomed meanings to those of ordinary skill in the applicable art(s).

The foregoing description of a preferred embodiment and best mode of the invention known to the applicant at this time of filing the application has been presented and is intended for the purposes of illustration and description. It is not intended to be exhaustive or limit the invention to the precise form disclosed and many modifications and variations are possible in the light of the above teachings. The embodiment was chosen and described in order to best explain the principles of the invention and its practical application and to enable others skilled in the art to best utilize the invention in various embodiments and with various modifications as are suited to the particular use contemplated. Therefore, it is intended that the invention not be limited to the particular embodiments disclosed for carrying out the invention.

We claim:

1. A method for electronically couriering records, comprising:
    splitting a record into personal information and non-personal information, the personal information and the non-personal information having an identifier to link the personal information to the non-personal information;
    encrypting the personal information and adding an encryption key;
    storing the record, including the personal information and the non-personal information, on a source node, having an electronic address;
    indexing the record on a server, wherein the server includes a database that further includes fields for storing the personal information, the encryption key and the electronic address of the source node on which the record is stored;
    transmitting the record from the source node to a target node, wherein the transmission of the record includes removing the personal information from the record prior to transmission of the stripped record, comprising non-personal information, from the source node;
    transmitting the personal information from the server to the target node, wherein the personal information is encrypted prior to transmission to the target node; and
    displaying the record on a record consumer computer, wherein the personal information is decrypted and coupled with the stripped record.

2. The method of claim 1, further including transmitting the personal information and the electronic address of the source node from the source to the server.

3. The method of claim 1, further including authorizing the record consumer computer to display the record.

4. The method of claim 3, wherein authorization includes validation by the server of an entered identification.

5. The method of claim 1, further including deleting the personal information from the record consumer computer when the record is no longer displayed on the computer.

6. The method of claim 1, further including copying the stripped record to a second record consumer.

7. The method of claim 6, wherein the copying of the stripped record includes authorization to couple the stripped record with the personal information.

8. The method of claim 1, further including authenticating the source node and the target node by the server.

9. The method of claim 1, wherein the coupling of the personal information and the stripped record is accomplished through association of the identifier.

10. The method of claim 1, wherein the record is in HL7 format.

11. A computer-readable storage medium containing computer executable code for instructing a central computer to perform the steps of:
    receiving personal information and an electronic address of a source node, wherein the source node include a record comprised on personal information and non-personal information, the personal information and the non-personal information having an identifier to link the personal information to the non-personal information;
    mediating the transmission of the record from the source node to a target node, wherein the transmission of the record includes removing the personal information from the record prior to transmission of the stripped record from the source node; and transmitting the personal information to the target node, wherein the personal information is encrypted prior to transmission to the target node.

12. The computer-readable storage medium of claim 11, further containing computer executable code for instructing a central computer to perform the step of authorizing a node computer to couple the personal information and the stripped record.

13. The computer-readable storage medium of claim 12, further containing computer executable code for instructing a central computer to perform the step of validating a record consumer computer, wherein validation allows the record consumer computer to display the record.

14. A computer-readable storage medium containing computer executable code for instructing a node computer to perform the steps of:

decrypting personal information received from a central computer, wherein the personal information is encrypted when received; and coupling the decrypted personal information with a stripped record received from a source computer, wherein the stripped record comprises non-personal information;

wherein the personal information and the stripped record are tagged with complimentary identifiers.

15. The computer-readable storage medium of claim 14, further containing computer executable code for instructing a node computer to display the coupled record on a record consumer computer.

16. The computer-readable storage medium of claim 15, further containing computer executable code for instructing a node computer to validate the record consumer computer prior to displaying the coupled record on the record consumer computer.

17. The computer computer-readable storage medium of claim 15, further containing computer executable code for instructing a node computer to delete the personal information from the record consumer computer when the coupled record is no longer displayed.

18. The computer-readable storage medium of claim 13, wherein further containing computer executable code for authenticating the source computer and the node computer by the central computer.

19. The method of claim 14, wherein the coupling of the personal information and the stripped record is accomplished through association of the complimentary identifiers.

20. The method of claim 19, wherein the complimentary identifiers are selected from a group consisting of: complimentary keys, complimentary watermarks, and complimentary hashes.

21. A system for electronically couriering records, comprising:

a central computer, in communication with a source node computer and a target node computer, capable of executing the steps of receiving personal information and an electronic address of a source node computer where a record, including personal information and non-personal information, the personal information and the non-personal information having complimentary identifiers to link the personal information to the non-personal information;

receiving a request from a target node computer to receive a copy of the record;

directing the source node computer to transmit a stripped record, consisting of the non-personal information, from the source node computer to the target node computer; and transmitting the personal information to the target node, wherein the personal information is encrypted prior to transmission to the target node.

22. The system of claim 21, further including a source node computer.

23. The system of claim 22, wherein the source node computer is capable of receiving the record from a record producer.

24. The system of claim 22, wherein the source node computer is capable of stripping the record of the personal information.

25. The system of claim 24, wherein the source node computer is further capable of storing the stripped record.

26. The system of claim 22, wherein the source node computer is capable of transmitting the personal information to the central computer.

27. The system of claim 22, wherein the source node computer is capable of transmitting its electronic address to the central computer.

28. The system of claim 22, wherein the source node computer is capable of tagging the stripped record and the personal information with complimentary identifiers.

29. The system of claim 21, further including a target node computer.

30. The system of claim 29, wherein the target node computer is capable of receiving the stripped record from the source node computer.

31. The system of claim 30, wherein the target node computer is capable of receiving the encrypted personal information from the central computer.

32. The system of claim 31, wherein the target node computer is capable of decrypting the personal information.

33. The system of claim 32, wherein the target node computer is capable of coupling the personal information with the stripped record.

34. The system of claim 28, further including a target node computer, wherein the target node computer is capable of coupling of the personal information and the stripped record by associating the complimentary identifiers.

35. The method of claim 34, wherein the complimentary identifiers are selected from a group consisting of: complimentary keys, complimentary watermarks, and complimentary hashes.

36. The system of claim 21, wherein the central computer includes a database that further includes fields for storing the personal information and the electronic address of the source node.

37. A method for providing secure transmission of images from an image producer to an image consumer, comprising:

storing an image, including a header, comprising personal information, and a body, comprising non-personal information, on a source node, having an electronic address, the personal information and the non-personal information having complimentary identifiers to link the personal information to the non-personal information;

storing the header on a server, wherein the server includes a database that further includes fields for storing the header and the electronic address of the source node on which the image is stored;

transmitting the body from the source node to a target node, wherein the transmission of the image includes removing the header from the image prior to transmission of the body from the source node;

transmitting the header from the server to the target node, wherein the header is encrypted prior to transmission to the target node; and displaying the image on an image consumer computer, wherein the header is decrypted and coupled with the body.

38. The method of claim 37, further including ordering generation of the image by the image consumer.

39. The method of claim 37, further including generating of the image by the image producer.

40. The method of claim 37, further including uploading the image to the source node.

41. The method of claim 37, further including transmitting the header and the electronic address to the server.

42. The method of claim 41, wherein harvesting the image further includes tagging the header and the body with complimentary identifiers.

43. The method of claim 37, wherein the body is transmitted to the image consumer computer following a request by the image consumer computer.

44. The method of claim 38, wherein the body is transmitted to the image consumer computer of the image consumer ordering the image prior to the image consumer computer requesting the transmission.

45. The method of claim 42, wherein the decrypted header and body are coupled by associating the complimentary identifiers.

46. The method of claim 37, wherein the image is in DICOM format.

47. The method of claim 37, further including copying the body and transmitting the body to a second image consumer, wherein the transmission includes authorization for the second image consumer to decrypt the header, couple the decrypted header and the body, and display the image on the second image consumer computer.

* * * * *